(12) United States Patent
Hickle

(10) Patent No.: US 7,201,734 B2
(45) Date of Patent: Apr. 10, 2007

(54) APPARATUS FOR DRUG DELIVERY IN ASSOCIATION WITH MEDICAL OR SURGICAL PROCEDURES

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 0 days.

(21) Appl. No.: 10/909,435

(22) Filed: Aug. 3, 2004

(65) Prior Publication Data
US 2005/0010166 A1 Jan. 13, 2005

Related U.S. Application Data

(63) Continuation of application No. 09/324,759, filed on Jun. 3, 1999, now Pat. No. 6,807,965.

(60) Provisional application No. 60/087,841, filed on Jun. 3, 1998.

(51) Int. Cl.
A61M 31/00 (2006.01)

(52) U.S. Cl. .................................................. 604/67

(58) Field of Classification Search ................ 600/300, 600/301; 604/65, 66, 67, 131; 128/204.23, 128/206.25
See application file for complete search history.

(56) References Cited

U.S. PATENT DOCUMENTS

| 1,176,146 | A | 3/1916 | Jones |
| 2,185,068 | A | 12/1939 | Sholes et al. |
| 2,225,201 | A | 12/1940 | Anderson |
| 2,690,178 | A | 9/1954 | Bickford |
| 2,798,438 | A | 4/1957 | Talpin et al. |
| 2,888,922 | A | 6/1959 | Bellville |
| 3,143,111 | A | 8/1964 | Green |
| 3,651,806 | A | 3/1972 | Hirshberg |
| 3,762,398 | A | 10/1973 | Schefke et al. |
| 3,898,983 | A | 8/1975 | Elam |

(Continued)

FOREIGN PATENT DOCUMENTS

JP 04-309362 10/1992

(Continued)

OTHER PUBLICATIONS

Michel B. M. R. F. Struys M.D., Ph.D. et al., Comparison of Closed-Loop Controlled Administration of Propofol Using Bispectral Index as the Controlled Variable Versus "Standard Practice" Controlled Administration, *Anesthesiology*, 2001, pp. 6-17.

(Continued)

Primary Examiner—Manuel Mendez
(74) Attorney, Agent, or Firm—Hogan & Hartson LLP

(57) ABSTRACT

Disclosed are devices for facilitating medical and/or procedures that are performed without "general anesthesia," which is also described in the specification as the state of patient "unconsciousness" resulting from a drug administered by an anesthetist or anesthesiologist. The devices safely and effectively provide and maintain drug infusions that do not push the patient into unconsciousness and/or general anesthesia. Devices according to embodiments of the invention include the use of stored parameters and/or values that correlate to drug delivery during a procedure, and a patient health monitor to measure and send signals regarding a patient health condition to a processor.

74 Claims, 30 Drawing Sheets

U.S. PATENT DOCUMENTS

| | | |
|---|---|---|
| 4,078,562 A | 3/1978 | Friedman |
| 4,080,966 A | 3/1978 | McNally et al. |
| 4,148,312 A | 4/1979 | Bird |
| 4,275,727 A | 6/1981 | Keeri-Szanto |
| 4,280,494 A | 7/1981 | Cosgrove, Jr. et al. |
| 4,308,866 A | 1/1982 | Jelliffe et al. |
| 4,392,849 A | 7/1983 | Petre et al. |
| 4,533,346 A | 8/1985 | Cosgrove, Jr. et al. |
| 4,550,726 A | 11/1985 | McEwen |
| 4,551,133 A | 11/1985 | Zegers De Beyl et al. |
| 4,610,254 A | 9/1986 | Morgan et al. |
| 4,634,426 A | 1/1987 | Kamen |
| 4,681,121 A | 7/1987 | Kobal |
| 4,688,577 A | 8/1987 | Bro |
| 4,718,891 A | 1/1988 | Lipps |
| 4,731,051 A | 3/1988 | Fischell |
| 4,756,706 A | 7/1988 | Kerns et al. |
| 4,871,351 A | 10/1989 | Feingold |
| 4,942,544 A | 7/1990 | McIntosh et al. |
| 5,046,491 A | 9/1991 | Derrick |
| 5,065,315 A | 11/1991 | Garcia |
| 5,088,981 A | 2/1992 | Howson et al. |
| 5,094,235 A | 3/1992 | Westenskow et al. |
| 5,183,038 A | 2/1993 | Hoffman et al. |
| 5,231,981 A | 8/1993 | Schreiber et al. |
| 5,258,906 A | 11/1993 | Kroll et al. |
| 5,262,944 A | 11/1993 | Weisner et al. |
| 5,286,252 A | 2/1994 | Tuttle et al. |
| 5,309,908 A | 5/1994 | Friedman et al. |
| 5,352,195 A | 10/1994 | McEwen |
| 5,432,698 A | 7/1995 | Fujita |
| 5,445,621 A | 8/1995 | Poli et al. |
| 5,507,277 A | 4/1996 | Rubsamen et al. |
| 5,522,798 A | 6/1996 | Johnson et al. |
| 5,555,891 A | 9/1996 | Eisenfeld |
| 5,558,638 A | 9/1996 | Evers et al. |
| 5,614,887 A | 3/1997 | Buchbinder |
| 5,630,710 A | 5/1997 | Tune et al. |
| 5,653,739 A | 8/1997 | Maurer et al. |
| 5,676,133 A | 10/1997 | Hickle et al. |
| 5,677,290 A | 10/1997 | Fukunaga |
| 5,713,856 A | 2/1998 | Eggers et al. |
| 5,730,140 A | 3/1998 | Fitch |
| 5,733,259 A | 3/1998 | Valcke et al. |
| 5,795,327 A | 8/1998 | Wilson et al. |
| 5,873,369 A | 2/1999 | Laniado et al. |
| 5,882,338 A | 3/1999 | Gray |
| 5,954,050 A | 9/1999 | Christopher |
| 5,957,885 A | 9/1999 | Bollish et al. |
| 5,980,501 A | 11/1999 | Gray |
| 6,062,216 A | 5/2000 | Corn |
| 6,152,130 A | 11/2000 | Abrams et al. |
| 6,158,430 A | 12/2000 | Pfeiffer et al. |
| 6,159,832 A | 12/2000 | Cheng et al. |
| 6,165,151 A | 12/2000 | Weiner |
| 6,165,154 A | 12/2000 | Gray et al. |
| 6,182,667 B1 | 2/2001 | Hanks et al. |
| 6,186,977 B1 | 2/2001 | Andrews et al. |
| 6,289,238 B1 | 9/2001 | Besson et al. |
| 6,302,844 B1 | 10/2001 | Walker et al. |
| 6,305,372 B1 | 10/2001 | Servidio |
| 6,305,373 B1 | 10/2001 | Wallace et al. |

FOREIGN PATENT DOCUMENTS

| | | |
|---|---|---|
| WO | 97/00092 | 1/1992 |
| WO | 97/07838 | 3/1997 |
| WO | 97/34648 | 9/1997 |
| WO | 98/10701 | 3/1998 |
| WO | 99/62403 | 12/1999 |

OTHER PUBLICATIONS

E. Mortier et al., Closed-Loop Controled Administration of Propofol Using Bispectral Analysis, *Anesthesia*, 1998 53, pp. 749-754.

J. Glen et al., The Development of 'Diprifusor': a TCI System for Propofol; *Anesthesia*, 1998, 53, Supplement 1, pp. 13-21.

J. Gray et al., Development of the Technology for 'Diprifusor' TCI Systems; *Anesthesia*, 1998, 53, Supplement 1, pp. 22-27.

G. N. C. Kenny et al., Closed-loop Control of Propofol Anesthesia; *British Journal of Anesthesia*, 83(s), 1999, pp. 223-228.

A New Level of Control for Faster, Mor Predictable Recovery, *Bis. Your Guide to the Hypnotic State During Anesthesia and Sedation*; p. 21.

P. Glass et al., Intravenous Drug Delivery Systems; *Anesthesia*, pp. 389-416.

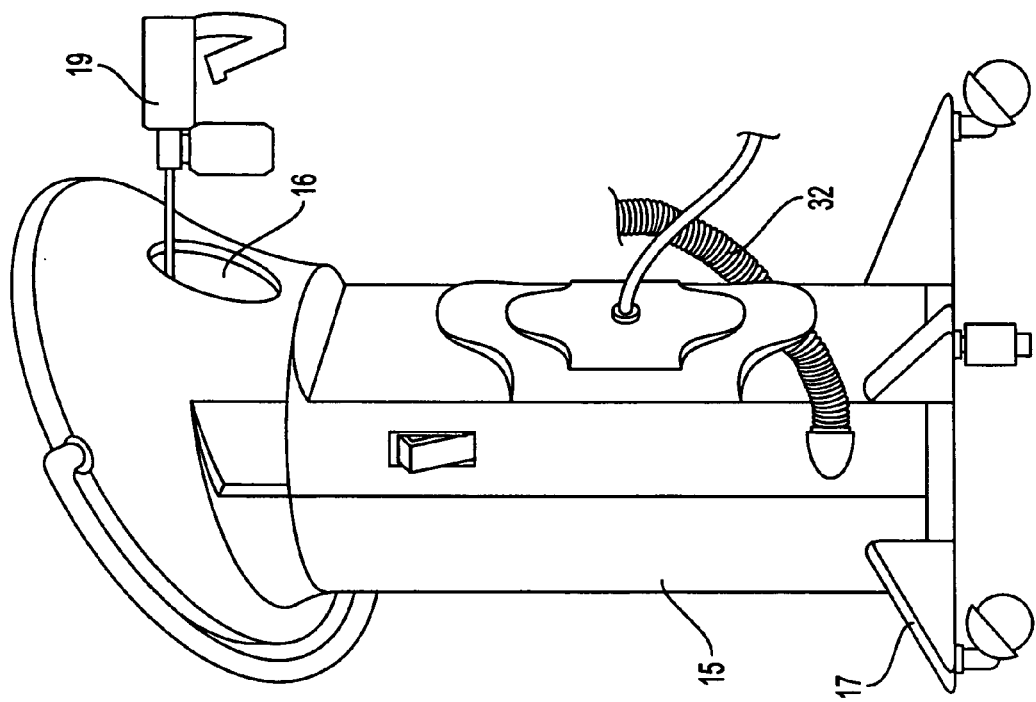
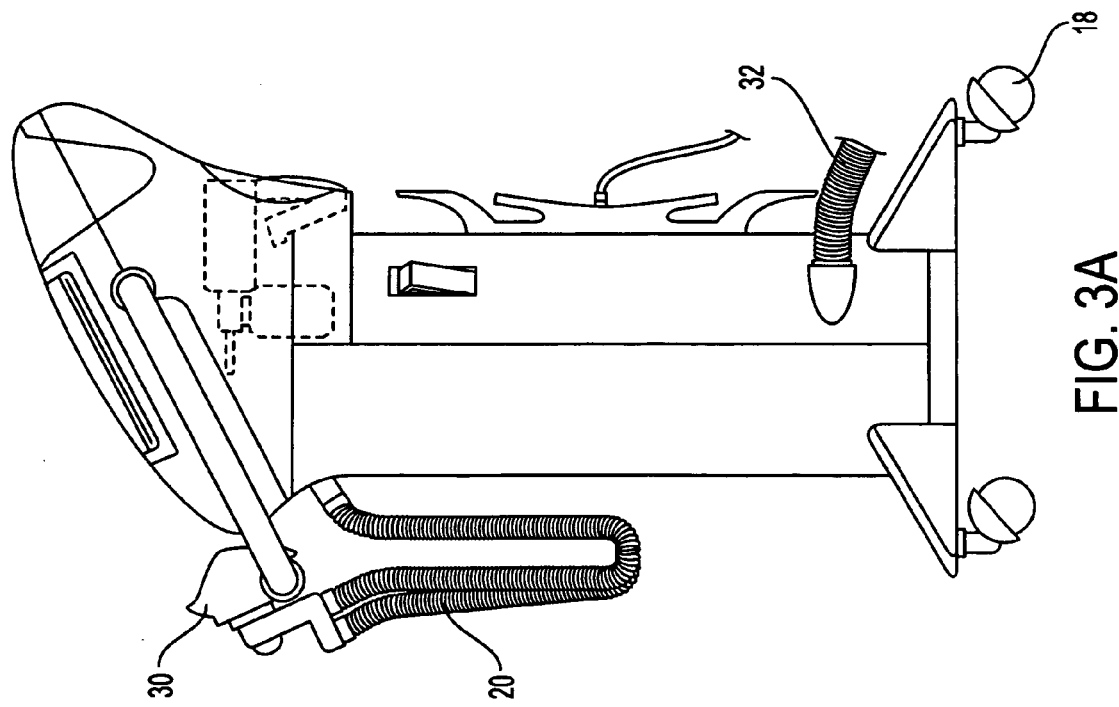
FIG. 3B
FIG. 3A

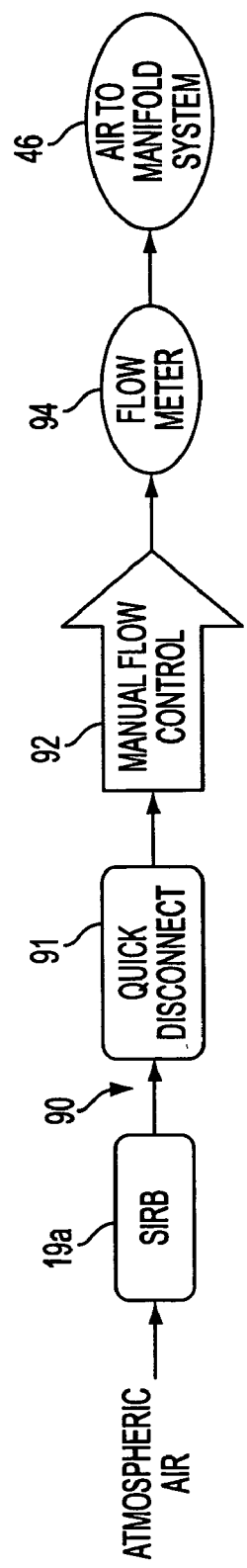
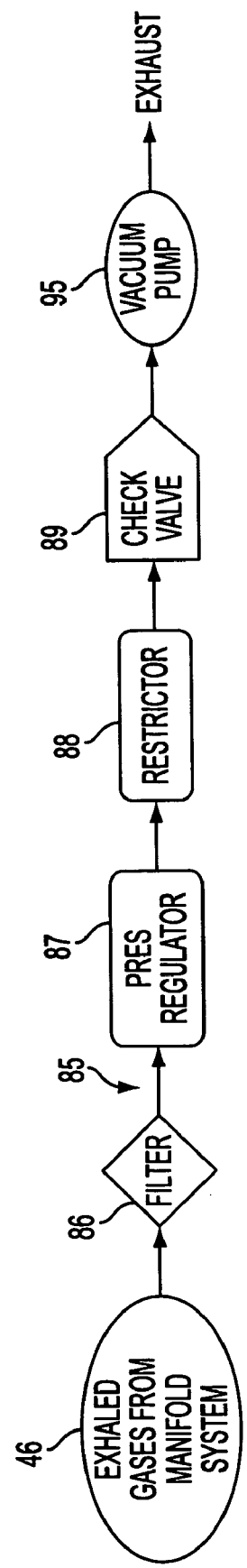
FIG. 10A
FIG. 10B

| PATIENT MONITOR | MONITOR READING | ACTION |
|---|---|---|
| $O_2$ SATURATION | ≥ 90% | NONE |
| | < 90%, ≥ 85% | ALARM 1 SOUNDS FOR 15 S. IF SILENCED MANUALLY, NO FURTHER ACTION IF NOT SILENCED, $N_2O$ IS REDUCED TO THE LESSER CONCENTRATION OF 45% OR CURRENT CONCENTRATION - 10%. SIMILAR ALGORITHMS FOR SEVOFLURANE AND IV INFUSIONS TO BE SPECIFIED. |
| | < 85%, ≥ 80% | ALARM 2 SOUNDS, $N_2O$ REDUCED TO THE LESSER CONCENTRATION OF 45% OR CURRENT CONCENTRATION - 10% IMMEDIATELY |
| | < 80% | ALARM 3 SOUNDS, $N_2O$ REDUCED TO 0% |
| PULSE RATE | ≥ 45/min. | NONE |
| | < 45/min., ≥ 35/min, | ALARM 1 SOUNDS FOR 15 S. IF SILENCED MANUALLY, NO FURTHER ACTION. IF NOT SILENCED, $N_2O$ IS REDUCED TO THE LESSER CONCENTRATION OF 45% OR CURRENT CONCENTRATION - 10% |
| | < 35/min. | ALARM 3 SOUNDS, $N_2O$ REDUCED TO 0% |
| $CO_2$ MAXIMUM | ≤ 50 mm Hg | NONE |
| | > 50 mm Hg, ≤ 55 mm Hg | ALARM 1 SOUNDS FOR 15 S. IF SILENCED MANUALLY, NO FURTHER ACTION. IF NOT SILENCED, $N_2O$ IS REDUCED TO THE LESSER CONCENTRATION OF 45% OR CURRENT CONCENTRATION - 10% |
| | > 55 mm Hg, ≤ 60 mm Hg | ALARM 2 SOUNDS, $N_2O$ REDUCED TO THE LESSER CONCENTRATION OF 45% OR CURRENT CONCENTRATION - 10% IMMEDIATELY |
| | < 60 mm Hg | ALARM 3 SOUNDS, $N_2O$ REDUCED TO 0% |
| RESPIRATION RATE | APNEA < 1 min. | NONE |
| | APNEA ≥ 1 min. | ALARM 2 SOUNDS, $N_2O$ REDUCED TO THE LESSER CONCENTRATION OF 45% OR CURRENT CONCENTRATION - 10% IMMEDIATELY |
| | ALARM 2 AND APNEA ≥ 30 s. | ALARM 3 SOUNDS, $N_2O$ REDUCED TO 0% |
| SYSTOLIC BP | > 70 mm Hg | NONE |
| | ≤ 70 mm Hg, > 65 mm Hg | ALARM 1 SOUNDS FOR 15 S. IF SILENCED MANUALLY, NO FURTHER ACTION. IF NOT SILENCED, $N_2O$ IS REDUCED TO THE LESSER CONCENTRATION OF 45% OR CURRENT CONCENTRATION - 10% |
| | ≤ 65 mm Hg, > 60 mm Hg | ALARM 2 SOUNDS, $N_2O$ REDUCED TO THE LESSER CONCENTRATION OF 45% OR CURRENT CONCENTRATION - 10% IMMEDIATELY |
| | ≤ 60 mm Hg | ALARM 3 SOUNDS, $N_2O$ REDUCED TO 0% |
| CONSCIOUSNESS MONITOR | PATIENT RESPONDS | NONE |
| | PATIENT DOES NOT RESPOND | ALARM 1 SOUNDS FOR 15 S. IF SILENCED MANUALLY, NO FURTHER ACTION. IF NOT SILENCED, $N_2O$ IS REDUCED TO THE LESSER CONCENTRATION OF 45% OR CURRENT CONCENTRATION - 10% |
| | ALARM 1 AND PATIENT DOES NOT RESPOND TO STIMULUS 30 s LATER | ALARM 2 SOUNDS, $N_2O$ REDUCED TO THE LESSER CONCENTRATION OF 45% OR CURRENT CONCENTRATION - 10% IMMEDIATELY |
| | ALARM 2 AND PATIENT DOES NOT RESPOND TO STIMULUS 30 s LATER | ALARM 3 SOUNDS, $N_2O$ REDUCED TO 0% |

| MONITOR | UNIT | TRANSITION REQUIREMENT | VALUE | | |
|---|---|---|---|---|---|
| O2 TANK PRESSURE | PSI | LOW TANK PRESSURE | > SETPOINT | < SETPOINT | N/A |
| O2 INTERRUPTION FAIL-SAFE | LOGICAL | O2 INTERRUPTED | FALSE | N/A | TRUE |
| TOTAL GAS FLOW | LITERS / MIN | LOW GAS FLOW | > SETPOINT | < SETPOINT | N/A |
| N2O TANK PRESSURE | PSI | LOW TANK PRESSURE | > SETPOINT | < SETPOINT | N/A |
| FiO2 | % | LOW FiO2 | >= 30 | N/A | < 30 |
| VACUUM PUMP | LOGICAL | INSUFFICIENT VACUUM PUMP | OK | FAIL | N/A |
| POWER | LOGICAL | INTERRUPTION IN POWER | OK | N/A | FAIL |
| NORMAL | | | NO CHANGE | START ALARM 1 | START ALARM 2 REDUCE N2O TO 0% |
| ALARM 1 | | | NORMAL STOP ALARM 1 | ALARM 1 IF DURATION > 15 SEC AND NOT SILENCED THEN REDUCE N2O TO 45% OR CURRENT - 10% | ALARM 2 START ALARM 2 REDUCE N2O TO 0% |
| | | | NORMAL | ALARM 1 | ALARM 2 |
| ALARM 2 | | | STOP ALARM 2 | GO TO ALARM 1 | NO CHANGE |
| | | | NORMAL | ALARM 1 | ALARM 2 |

APPARATUS FOR DRUG DELIVERY IN ASSOCIATION WITH MEDICAL OR SURGICAL PROCEDURES

CROSS REFERENCE TO RELATED APPLICATIONS

This application is a continuation of U.S. patent application Ser. No. 09/324,759, filed Jun. 3, 1999, now U.S. Pat. No. 6,807,965, issued Oct. 26, 2004, which application claims priority to U.S. Provisional Patent Application Ser. No. 60/087,841, filed Jun. 3, 1998.

BACKGROUND OF THE INVENTION

Field of the Invention

This invention relates generally to an apparatus and method for relieving patient pain and/or anxiety. More particularly, this invention relates to a system and method for providing sedation, analgesia and/or amnesia to a conscious patient undergoing a painful or anxiety-producing medical or surgical procedure, or suffering from post-procedural or other pain or discomfort. The invention electronically integrates through conservative software management the delivery of one or more sedative, analgesic or amnestic drugs with the electronic monitoring of one or more patient physiological conditions. In one form, the invention includes the use of one or more sets of stored data-defining parameters reflecting patient and system states, the parameters being accessed through software to conservatively manage and correlate drug delivery to safe, cost effective, optimized values related to the conscious patient's vital signs and other physiological conditions.

BACKGROUND OF THE INVENTION

This invention is directed to providing a conscious patient who is undergoing a painful, uncomfortable or otherwise frightening (anxiety-inspiring) medical or surgical procedure, or who is suffering from post-procedural or other pain or discomfort, with safe, effective and cost-effective relief from such pain and/or anxiety. Focuses of the invention include, but are not limited to, enabling the provision of sedation (inducement of a state of calm), analgesia (insensitivity to pain) and/or amnesia to a conscious patient (sometimes referred to collectively as "conscious sedation") by a nonanesthetist practitioner, i.e., a physician or other clinician who is not an anesthesiologist (M.D.A.) or certified nurse anesthetist (C.R.N.A.), in a manner that is safe, effective and cost-effective; the provision of same to patients in ambulatory settings such as hospital laboratories, ambulatory surgical centers, and physician's offices; and the provision of patient post-operative or other pain relief in remote medical care locations or in home care environments. To those ends, the invention mechanically integrates through physical proximity and incorporation into an overall structural system and electronically integrates through conservative, decision-making software management, the delivery of one or more sedative, analgesic or amnestic drugs to the patient with the electronic monitoring of one or more patient physiological conditions.

In traditional operating rooms, anesthesiologists provide patients relief from pain, fear and physiological stress by providing general anesthesia. "Anesthesia" is typically used (and is so used herein) interchangeably with the state of "unconsciousness." Over a billion painful and anxiety-inspiring medical and surgical procedures, however, are performed worldwide each year without anesthesia. Thus, outside the practice of anesthesiology there are currently a large number of patients who, while conscious, undergo medical or surgical procedures that produce considerable pain, profound anxiety, and/or physiological stress. Such medical or surgical procedures are often performed by procedural physicians (nonanesthetists) in hospital laboratories, in physicians' offices, and in ambulatory surgical centers. For example, physician specialists perform painful procedures on conscious patients such as pacemaker placement, colonoscopies, various radiological procedures, microlaparoscopy, fracture reduction, wound dressing changes in burn units, and central and arterial catheter insertion in pediatric patients, in hospital laboratory settings. Primary care physicians perform such procedures as flexible sigmoidoscopies, laceration repairs, bone marrow biopsies and other procedures in physicians' offices. Many surgical specialists perform painful procedures such as anterior segment repairs by ophthalmologists, plastic procedures by cosmetic surgeons, foreign body removal, transurethral procedures, incisions of neck and axilla nodes, and breast biopsies in their offices or in ambulatory surgical centers. The needs of patients for safe and effective pain and anxiety relief during and after such procedures are currently unmet.

Conscious sedation techniques currently available for use by procedural physicians (nonanesthetists) during medical or surgical procedures such as those described above include sedatives and opioids given orally, rectally or intra-muscularly; sedatives and analgesics administered intravenously; and local anesthetics. Often, however, such techniques are less than satisfactory.

In the case of oral, rectal or intramuscular administration of sedatives and opioids by procedural physicians during the provision of conscious sedation, there are currently no effective means available to assure that the effects of those drugs can be readily controlled to meet patient need. This is due in part to the variable interval between administration and the onset and dissipation of drug effect. Unreliable sedation and analgesia can result because of mismatches between the dosage administered and the patient's needs which can vary depending on the condition of the patient and the type of procedure performed. Such administration of sedation can also produce an unconscious patient at risk for developing airway obstruction, emesis with pulmonary aspiration or cardiovascular instability. To attempt to avoid these complications, procedural physicians often administer sedatives and analgesics sparingly. This may reduce the risk of major complications, but may also mean that few patients receive adequate relief from pain and/or anxiety during medical and surgical procedures outside the practice of anesthesiology.

The use of intravenous administration of sedatives and analgesics to conscious patients by procedural physicians in settings such as hospital laboratories, physicians' offices and other ambulatory settings is also less than satisfactory. With respect to intravenous bolus administration, plasma concentrations vary considerably when drugs are injected directly into the blood stream. This can result in initially excessive (potentially toxic) levels followed by sub-therapeutic concentrations. Although intravenously administered drugs can be titrated to the patient's need, doing so safely and effectively usually requires the full-time attention of a trained care giver, e.g., an anesthesiologist. Costs and scheduling difficulties among other things typically preclude this option.

Due to the difficulties described above involving administration of sedatives and opioids, many procedural physicians rely on local anesthetics for pain relief. However, local anesthetics alone usually provide inadequate analgesia (insensitivity to pain) for most medical and surgical procedures and the injections themselves are often relatively painful.

In short, current methods commonly available to procedural physicians for providing effective pain relief to conscious patients outside the practice of anesthesiology typically fall short of the objective. Moreover, there are currently no clear standards of practice for nonanesthetists to guide the relief of pain and anxiety for conscious patients. There is not adequate training for such practitioners in the diagnosis and treatment of complications that may arise or result from the provision of sedation and analgesia to conscious patients. Procedures or mechanisms for ongoing quality management of the care of conscious patients undergoing painful and anxiety-inspiring medical or surgical procedures and the devices and methods employed in that care are inadequate.

An additional focus of this invention is the electronic monitoring of a conscious patient's physiological condition during drug delivery, and the electronic management of drug delivery by conservative decision-making software that integrates and correlates drug delivery with electronic feedback values representing the patient's physiological condition, thereby ensuring safe, cost-effective, optimized care. Significantly, in many cases involving conscious sedation, the patient's physiological condition is inadequately monitored or not electronically monitored at all during drug delivery and recovery therefrom. That is, there is often no electronic monitoring of basic patient vital signs such as blood pressure, blood oxygen saturation (oximetry) nor of carbon dioxide levels in a patient's inhaled and exhaled gases (capnometry). For example, patients undergoing painful procedures in dentists' offices may receive nitrous oxide ($N_2O$) gas to relieve pain, but that drug delivery is often not accompanied by electronic monitoring of a patient's physiological condition, and currently there are no devices available to nonanesthetists which safely and effectively integrate electronic patient monitoring with such drug delivery mechanisms.

In other circumstances involving the provision of conscious sedation and analgesia by the procedural physician, such as a cardiologist's performing a catheterization procedure in a hospital laboratory, electronic patient monitors are sometimes used, but again, there are no devices currently available to the nonanesthetist which safely and effectively integrate both mechanically (through close, physical proximity and incorporation into a structural system), and electronically (through conservative software management), electronic patient monitors with mechanisms for drug delivery.

One aspect of the invention of this application is directed to the simplification of drug delivery machines for relieving patient pain and anxiety by eliminating features of those machines that complicate the provision of patient pain and anxiety relief, and by including those features that enable nonanesthetists to provide safe, cost-effective, optimized conscious sedation and analgesia. More specifically, current anesthesia machines used by anesthesiologists to provide general anesthesia and a form of conscious sedation administered by the anesthesiologist known as "monitored anesthesia care" (MAC) include various complex features such as oxygen ($O_2$) flush valves which are capable of providing large amounts of oxygen to the patient at excessive pressures, and carbon dioxide ($CO_2$) absorbent material which absorbs $CO_2$ from a patient's exhaled gases. In addition, anesthesia machines typically deliver halogenated anesthetic gases which can trigger malignant hyperthermia. Malignant hyperthermia is a rare, but highly critical condition requiring the advanced training and skills of an anesthesiologist for rapid diagnosis and therapy. The airway circuit in current anesthesia machines is circular in nature and self-contained in that the patient inhales an oxygen/anesthetic gas mixture, exhales that mixture which is then passed through $CO_2$ absorbent material, re-inhales the filtered gas mixture (supplemented by additional anesthetic and oxygen), and repeats the process.

These aspects of anesthesia machines, among others, carry attendant risks for the patient such that anesthesia machines require operation by a professional trained through a multi-year apprenticeship (e.g., an anesthesiologist or C.R.N.A.) in detecting and correcting failure modes in the technology. For example, an oxygen flush valve can cause oxygen to enter a patient's stomach thereby causing vomiting; and carbon dioxide absorbent material can fail in which case the patient could receive too much carbon dioxide if the failure was not promptly detected and corrected. Moreover, the use of the self-contained, circular airway circuit could result in a circumstance whereby if the supply of $O_2$ suddenly ceased, a patient would only be breathing the finite supply of oxygen with no provision for administration of additional requirements for $O_2$ or atmospheric air. Such features, among others, make anesthesia machines unusable by nonanesthetists. Therefore, a focal point of this aspect of the invention is the simplification of a drug delivery apparatus by selecting and incorporating the appropriate features to facilitate the rendition of safe and effective conscious sedation by nonanesthetists.

Certain aspects of this invention also focus on ensuring maintenance of patient consciousness to prevent airway difficulties, including monitoring the level of patient consciousness during the delivery of one or more sedative, analgesic and/or amnestic drugs to a conscious, non-intubated, spontaneously-ventilating patient to prevent airway difficulties. For patients not intubated on a ventilator, monitoring the level of patient consciousness is important to provide information about the likelihood of depressed airway reflexes and respiratory drive to breathe, the ability to maintain a patent airway, and the likelihood of cardiovascular instability. Despite the importance of monitoring and maintaining adequate levels of consciousness in certain medical settings, there is no currently available device for ensuring maintenance of patient consciousness by integrating mechanically and electronically such monitoring of a patient's level of consciousness with a drug delivery system. The invention of this application is directed to this unmet need, as well.

This invention is also directed to providing conscious patients relief from pain and/or anxiety in a manner that is cost-effective and time efficient. Current solutions for relieving patient pain and anxiety by drug delivery and electronic monitoring of a patient's physiological condition are expensive and require a great deal of time to set-up and take down. Also, the current requirement or desire for the presence of an anesthesiologist during some medical or surgical procedures increases costs, especially if that desire requires in-patient care as opposed to care in an ambulatory setting. To the extent medical procedures are performed on conscious patients without adequate sedation and analgesia due to the current unavailability of appropriate methods and devices for providing such care (e.g., wound dressing changes in burn wards), such procedures may need to be conducted on numerous occasions, but over short periods of time (due to a patient's inability to tolerate the level of pain), as opposed to conducting a fewer number of more definitive procedures. The requirement of multiple sessions of care also typically involves increased costs. This invention addresses such cost-effectiveness concerns and provides solutions to problems such as those described.

The invention is further directed to the provision of relief from post-operative or other post-procedural pain and discomfort in remote medical care locations and home care type settings. Current devices may permit certain patients in, for example, a home care type setting, to provide themselves with an increased dosage of analgesic through the use of a patient-controlled drug delivery device, e.g., a device that permits a patient to press a button or toggle a switch and receive more analgesic (often intravenously or transdermally). This practice is sometimes called "PCA" or patient-controlled analgesia. Known commercially available PCA-type devices do not electronically integrate and conservatively manage delivery of analgesics in accord with the electronic monitoring of a patient's physiological condition. This invention focuses on this unmet need, as well.

An additional aspect of this invention is directed to the integration of a billing/information system for use with an apparatus providing sedation, analgesia and/or amnesia to conscious patients in physician's offices, hospital laboratory or other ambulatory settings or remote medical care locations. Current techniques for automated billing and invoice generating provide inadequate and inefficient methods for tracking recurring revenues derived from repeated use of medical devices such as the apparatus of this invention.

Other focuses of the invention are apparent from the below detailed description of preferred embodiments.

DESCRIPTION OF RELATED ART

Known machines or methods administered by the nonanesthetist for providing conscious, non-intubated, spontaneously-ventilating patients with sedation and analgesia are unreliable, not cost-effective or are otherwise unsatisfactory. No commercially available devices reliably provide such patients with safe and cost-effective sedation, analgesia and amnesia to conscious patients by integrating and correlating the delivery of sedative, analgesic and/or amnestic drugs with electronic monitoring of a patient's physiological condition. Available drug delivery systems do not incorporate a safety set of defined data parameters so as to permit drug delivery to be conservatively managed electronically in correlation with the patient's physiological conditions, including vital signs, to effectuate safe, cost-effective and optimized drug delivery to a patient. Available drug delivery systems do not incorporate alarm alerts that safely and reliably free the nonanesthetist practitioner from continued concern of drug delivery effects and dangers to permit the nonanesthetist to focus on the intended medical examination and procedure. Moreover, there are no known patient-controlled analgesia devices that mechanically and electronically integrate and correlate (through conservative software management) patient requests for adjustments to drug dosage and electronic monitoring of patient physiological conditions.

Known techniques have focused on the delivery of sedation and analgesia to conscious patients with inadequate or no electronic monitoring of patient physiological conditions, including vital signs, and no electronic integration or correlation of such patient monitoring with drug delivery. Other techniques have focused on the provision of anesthesia to unconscious patients with the requirement of an anesthesiologist to operate a complicated, failure-intensive anesthesia machine.

Presently known nitrous oxide delivery systems such as those manufactured by Matrx Medical, Inc., Accutron, Inc., and others are used primarily in dental offices for providing conscious sedation only. Such devices contain sources of nitrous oxide and oxygen, a gas mixing device and system monitors, but no mechanical or electrical integration of patient physiological condition monitors with drug delivery mechanisms. Similarly, other known drug delivery systems (e.g., intravenous infusion or intramuscular delivery mechanisms) for providing sedatives and analgesics to conscious patients used, for example, in hospital laboratories, do not include mechanical or electronic integration of patient physiological condition monitors with drug delivery mechanisms.

Anesthesia machines used by anesthesiologists to provide general anesthesia or MAC, such as, by way of example, the NARKOMED line of machines manufactured by North American Drager and EXCEL SE ANESTHESIA SYSTEMS manufactured by Ohmeda Inc., mechanically integrate electronic patient monitors in physical proximity to drug delivery mechanisms. These machines, however, employ features such as $O_2$ flush valves, malignant hyperthermia triggering agents, $CO_2$ absorbent material, as well as circular airway circuits, among others, thereby requiring operation by an M.D.A. (or C.R.N.A.), to avoid the occurrence of life-threatening incidents. These devices do not provide for the electronic integration or management of drug delivery in correlation with the monitoring of a patient's physiological condition, much less such electronic management through conservative, decision-making software or logic incorporating established safe data-defining parameters.

U.S. Pat. No. 2,888,922 (Bellville) discloses a servo-controlled drug delivery device for automatic and continuous maintenance of the level of unconsciousness in a patient based on voltages representative of the patient's cortical activity obtained by means of an electroencephalograph (EEG). The device continuously and automatically increases or decreases in robotic fashion the flow of anesthetic gas (or I.V. infusion) in response to selected frequencies of brain potential to maintain a constant level of unconsciousness.

U.S. Pat. No. 4,681,121 (Kobal) discloses a device for measuring a patient's sensitivity to pain during the provision of anesthesia, by applying a continuous, painful stimulus to the nasal mucosa and regulating the level of anesthesia in response to EEG signals indicating the patient's response to the nasal pain stimulus, with the goal of maintaining a sufficient level of unconsciousness.

Among other things, none of the above-described known devices manages drug delivery to conscious patients employing conservative decision-making software or logic which correlates the drug delivery to electronic patient feedback signals and an established set of safety data parameters.

SUMMARY OF THE INVENTION

The invention provides apparatuses and methods to safely and effectively deliver a sedative, analgesic, amnestic or other pharmaceutical agent (drug) to a conscious, non-intubated, spontaneously-ventilating patient. The invention is directed to apparatuses and methods for alleviating a patient's pain and anxiety before and/or during a medical or surgical procedure and for alleviating a patient's post-operative or other post-procedural pain or discomfort while simultaneously enabling a physician to safely control or manage such pain and/or anxiety. The costs and time loss often associated with traditional operating room settings or other requirements or desires for the presence of anesthetists may thus be avoided.

A care system in accordance with the invention includes at least one patient health monitor which monitors a patient's physiological condition integrated with a drug delivery controller supplying an analgesic or other drug to the patient. A programmable, microprocessor-based electronic controller compares the electronic feedback signals generated from the patient health monitor and representing the patient's actual physiological condition with a stored safety data set reflecting safe and undesirable parameters of at least one patient physiological condition and manages the application or delivery of the drug to the patient in accord with that comparison. In a preferred embodiment, the management of drug delivery is effected by the electronic controller via conservative, decision-making software accessing the stored safety data set.

In another aspect the invention also includes at least one system state monitor which monitors at least one operating condition of the care system, the system state monitor being integrated with a drug delivery controller supplying drugs to the patient. In this aspect, an electronic controller receives instruction signals generated from the system monitor and conservatively controls (i.e., curtails or ceases) drug delivery in response thereto. In a preferred embodiment, this is accomplished through software control of the electronic controller whereby the software accesses a stored data set reflecting safe and undesirable parameters of at least one operating condition of the care system, effects a comparison of the signal generated by the system state monitor with the stored data set of parameters and controls drug delivery in accord with same, curtailing or ceasing drug delivery if the monitored system state is outside of a safe range. The electronic controller may also activate attention-commanding devices such as visual or audible alarms in response to the signal generated by the system state monitor to alert the physician to any abnormal or unsafe operating state of the care system apparatus.

The invention is further directed to an apparatus which includes a drug delivery controller, which delivers drugs to the patient, electronically integrated with an automated consciousness monitoring system which ensures the consciousness of the patient and generates signal values reflecting patient consciousness. An electronic controller is also included which is interconnected to the drug delivery controller and the automated consciousness monitor and manages the delivery of the drugs in accord with the signal values reflecting patient consciousness.

In another aspect, the invention includes one or more patient health monitors such as a pulse oximeter or capnometer and an automated consciousness monitoring system, wherein the patient health monitors and consciousness monitoring system are integrated with a drug delivery controller supplying an analgesic or other drug to the patient. A microprocessor-based electronic controller compares electronic feedback signals representing the patient's actual physiological condition including level of consciousness, with a stored safety data set of parameters reflecting patient physiological conditions (including consciousness level), and manages the delivery of the drug in accord with that comparison while ensuring the patient's consciousness. In additional aspects of the invention the automated consciousness monitoring system includes a patient stimulus or query device and a patient initiate response device.

The invention also provides apparatuses and methods for alleviating post-operative or other post-procedural pain or discomfort in a home care-type setting or remote medical care location. Here the care system includes at least one patient health monitor integrated with patient-controlled drug delivery. An electronic controller manages the patient-controlled drug delivery in accord with electronic feedback signals from the patient health monitors. In a preferred embodiment the electronic controller is responsive to software effecting conservative management of drug delivery in accord with a stored safety data set.

DESCRIPTION OF THE DRAWINGS

Other objects and many of the intended advantages of the invention will be readily appreciated as they become better understood by reference to the following detailed description of preferred embodiments of the invention considered in connection with the accompanying drawings, wherein:

FIGS. 3A and 3B are side-elevational views of a preferred embodiment of an apparatus constructed in accordance with this invention.

FIG. 10A depicts a preferred embodiment of a manual bypass system in accordance with the invention.

FIG. 10B depicts a preferred embodiment of a scavenger system in accordance with the invention.

FIG. 21A depicts examples of drug delivery management protocols for 3-stage alarm states reflecting monitored patient parameters in accordance with the invention.

FIG. 21B depicts examples of drug delivery management protocols for 2-stage alarm states reflecting monitored system state parameters in accordance with the invention.

DETAILED DESCRIPTION OF PREFERRED EMBODIMENTS

The embodiments illustrated below are not intended to be exhaustive or to limit the invention to the precise forms disclosed. The embodiments are chosen and described in order to explain the principles of the invention and its applications and uses, and thereby enable others skilled in the art to make and utilize the invention.

Figure 1:
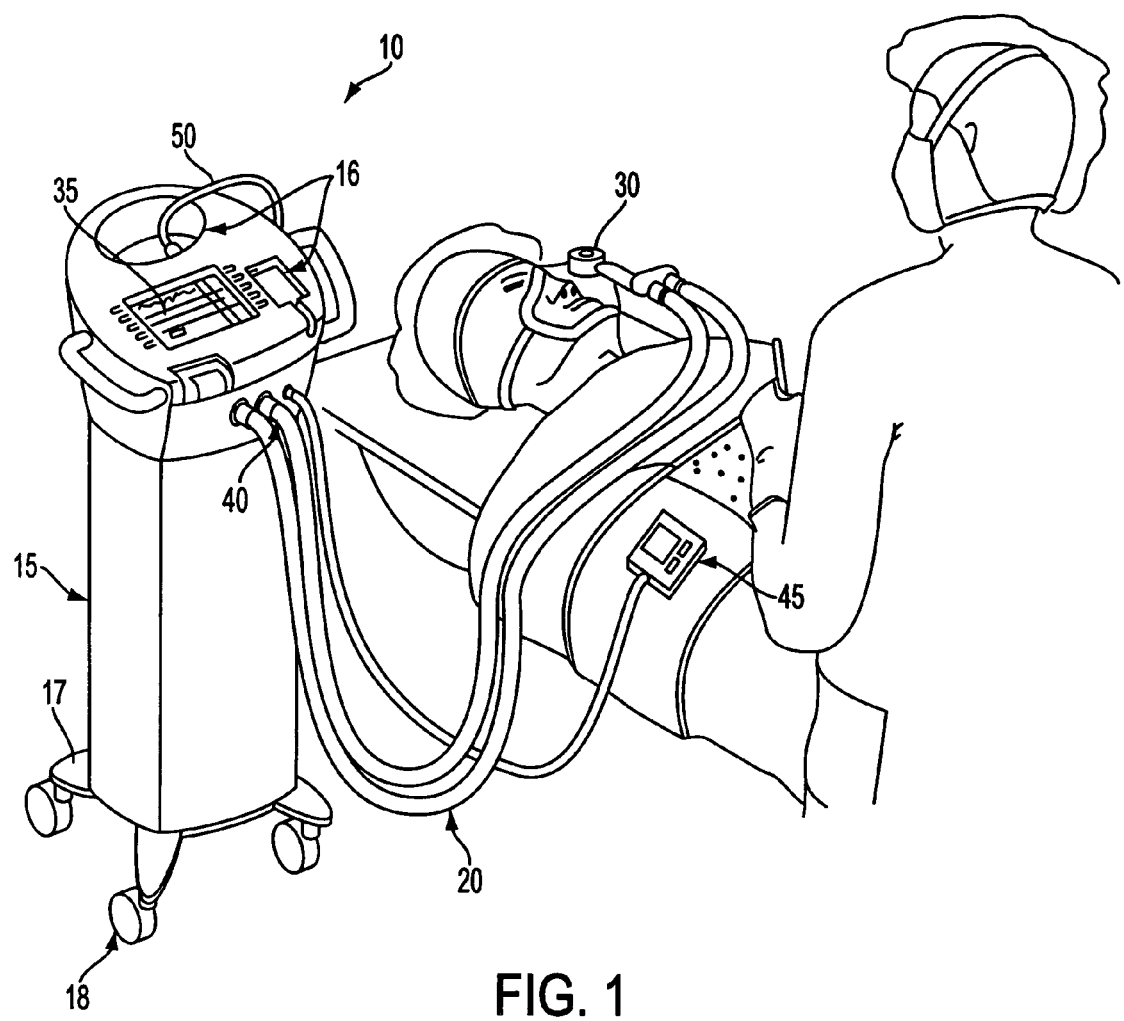
FIG. 1 is a perspective view of a preferred embodiment of a care system apparatus constructed in accordance with this invention, depicting the provision of sedation, analgesia and/or amnesia to a conscious patient by a nonanesthetist.

FIG. 1 shows a care system 10 constructed in accordance with this invention, providing sedative, analgesic and/or amnestic drugs to a conscious, non-intubated, spontaneously-ventilating patient undergoing a medical or surgical procedure by a procedural physician. The system 10 has a generally columnar housing 15 with various storage compartments 16 therein for storage of user and patient interface devices, and a base 17 supported on castor wheels 18. A drug delivery system 40 delivers a mixture of one or more gaseous sedative, analgesic or amnestic drugs in combination with oxygen ($O_2$) gas to a patient, and includes a one-way airway circuit 20 connected at one end to a face mask 30 and at the other end to a manifold valving system contained within housing 15. FIGS. 3A and 3B show from a side-elevation perspective, airway circuit 20, face mask 30, and exhaust hose 32 through which scavenged patient exhaled gases are exhausted to a safe location.

Figure 2:
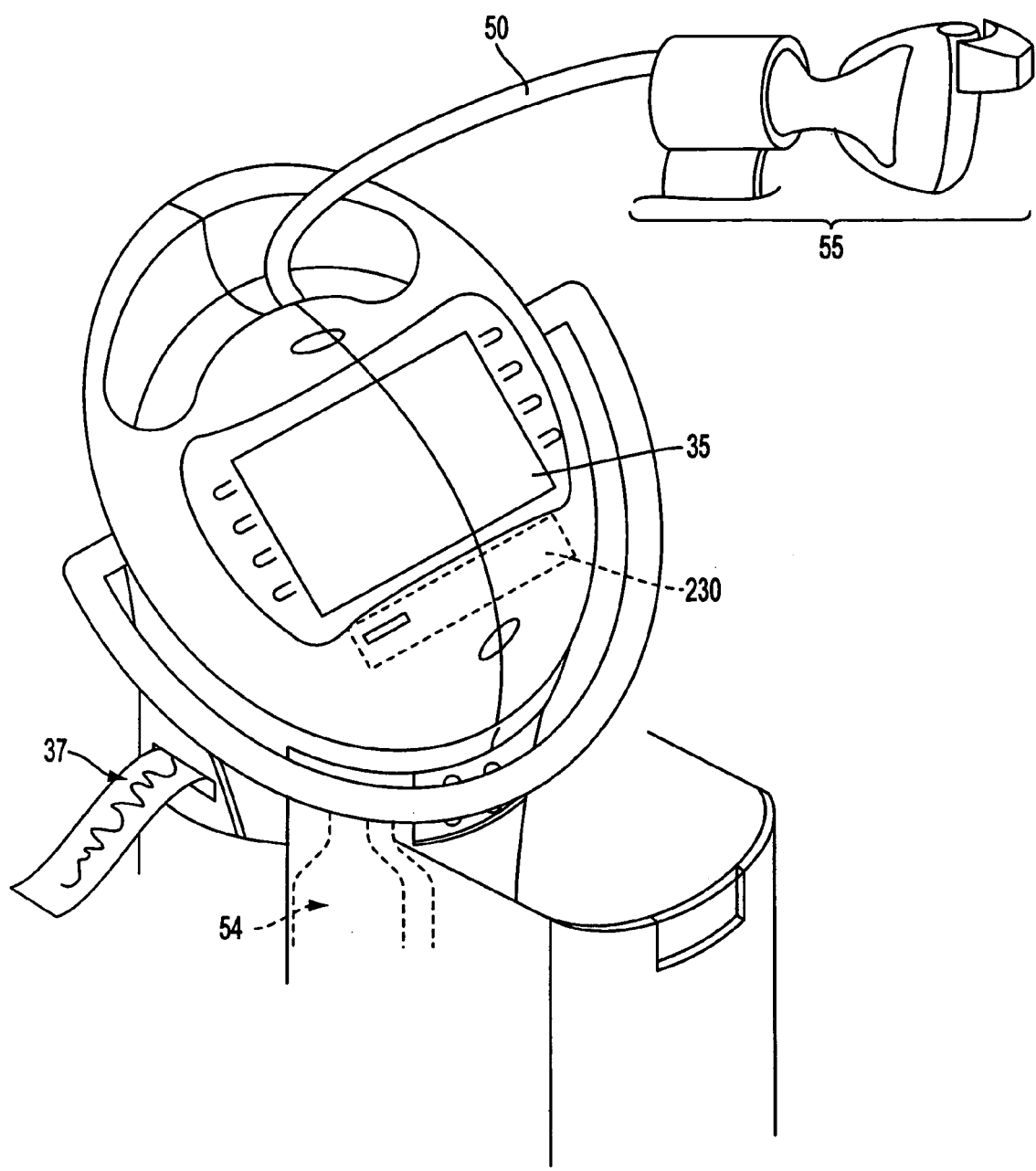
FIG. 2 is a perspective view of a preferred embodiment of a care system apparatus constructed in accordance with this invention depicting user interface and patient interface devices.

Referring to FIG. 2, lead 50 connects one or more patient interface devices (e.g., 55) to a microprocessor-based electronic controller or computer (sometimes also referred to herein as main logic board, MLB) located within housing 15. The electronic controller or main logic board may be comprised of combinations of available programmable-type microprocessors and other "chips," memory devices and logic devices on various board(s) such as those manufactured by Texas Instruments (e.g., XK21E) and National Semiconductor (e.g., HKL 72, among others. Patient interface devices 55 can include one or more patient health monitors that monitor a patient's physiological condition, such as known pulse oximeter, capnometer (not shown), non-invasive blood pressure monitors; EKG, EEG, acoustical monitors (not shown), and others; an automated consciousness monitoring system, including query initiate and response devices in accordance with the invention (described below); and patient drug dosage request devices (also described below). The main logic board electronically manages operation of the apparatus 10 by means of conservative, decision-making software that integrates and correlates patient feedback signals received from the one or more patient health monitors with drug delivery.

Also shown in FIGS. 1 and 2 are various user interface devices, including a display device 35 integrated into the top surface of apparatus 10 which displays patient and system parameters and operation status of the apparatus, a printer 37 which prints, for example, a hard copy of patient parameters indicating the patient's physiological condition and the status of various system alarms with time stamps, and a remote control device 45 which permits a physician to interact with apparatus 10. The various patient and user interface devices are described in more detail below.

It should be recognized that although certain embodiments of the invention show the analgesic delivery system 40 in a form for delivering one or more sedative, analgesic or amnestic drugs in gaseous form, the invention also specifically includes embodiments where such drugs are delivered intravenously, in nebulized, vaporized or other inhaled form, and/or transdermally such as by using known ion-transfer principles. Drugs that may be delivered by the care system include, but are not limited to, nitrous oxide, propofol, remifentanil, dexmedetamidine, epibatadine and sevoflurane. Alternative embodiments are described in more detail herein.

Figure 4A:
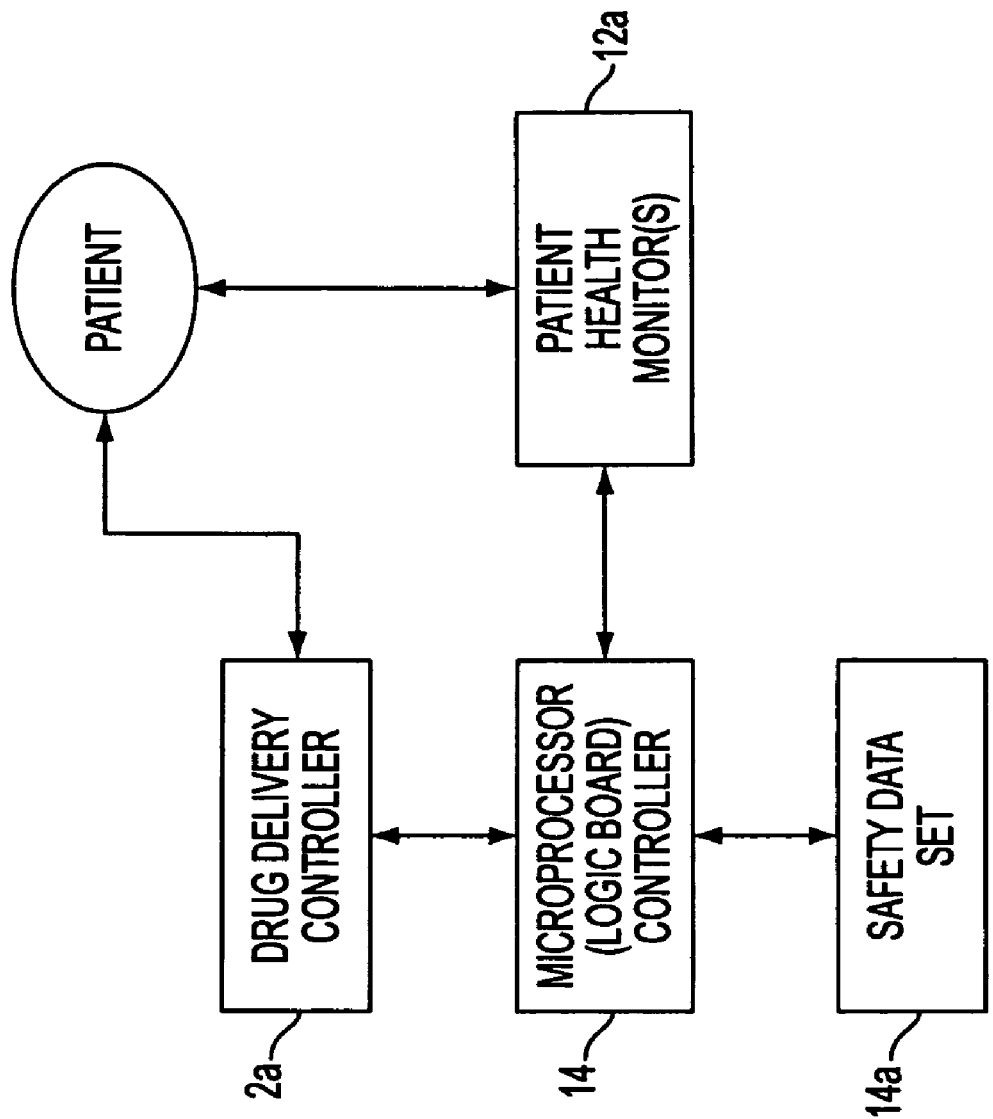
FIG. 4A is a block diagram overview of the invention.
Figure 4B:
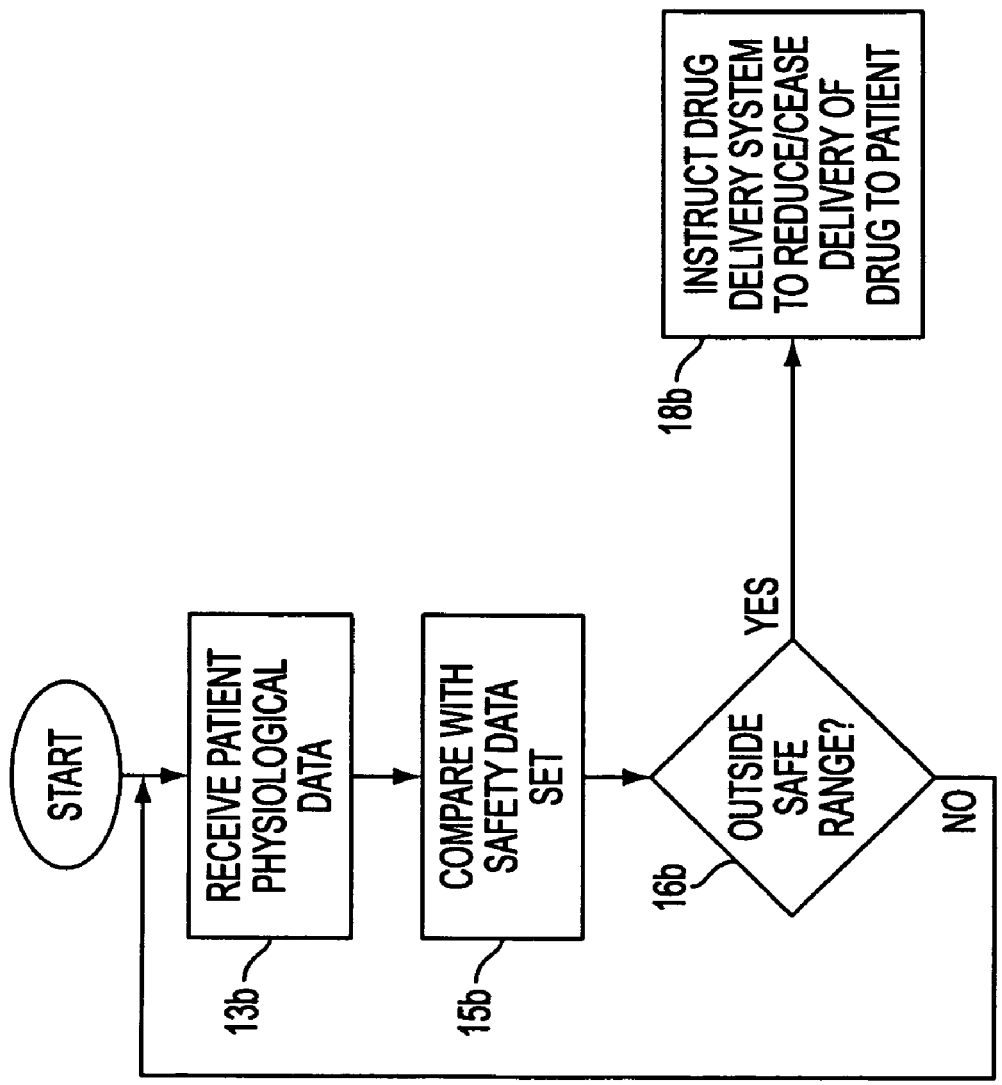
FIG. 4B is an overview data-flow diagram depicting the drug delivery management aspect of the invention.

FIG. 4A is a block diagram overview of a preferred embodiment of the invention. FIG. 4B is an overview data flow diagram depicting the drug delivery management steps performed by the software/logic control of microprocessor controller 14 in a preferred embodiment of the invention. In FIG. 4A, one or more patient health monitors 12a (which may include one or more known patient physiological condition monitors such as pulse oximeters, capnometers, other ventilatory monitors, non-invasive blood pressure monitors, EKG, EEG and others, as well as a patient consciousness monitoring system) are electronically coupled, through suitable A-D converters where appropriate, to electronic controller 14, described above. Patient health monitors 12a generate electronic feedback signals representing actual patient physiological data which are converted to electronic signals and then provided to controller 14. Now referring to FIG. 4B, electronic controller 14, e.g., through appropriate software and/or logic, compares the received electronic patient feedback signals 13b with the safety data set 15b stored in a memory device (such as an EPROM device).

The stored safety data set 14a (FIG. 4A) contains at least one set of data parameters representing safe and undesirable patient physiological conditions. Based on the comparison of the actual monitored patient physiological data 13b with the safety data set 14a, controller 14 determines whether the monitored patient physiological data is outside of a safe range (FIG. 4B, 16b). If the monitored patient data is outside of a safe range, electronic controller 14 sends instruction commands (signals) to drug delivery controller 2a (FIG. 4A) instructing drug delivery controller 2a to conservatively manage (e.g., reduce or cease) drug delivery (FIG. 4B, 18b). Drug delivery controller 2a may be a standard solenoid valve-type electronic flow controller known to those skilled in the art.

As is described below, additional embodiments of the invention also contemplate provision of electronic feedback signals representing patient-controlled drug dosage increase or decrease requests to controller 14 and electronic management of drug delivery in consideration of such patient requests vis-a-vis the patient's physiological parameters and/or the state of the care system.

Figure 5:
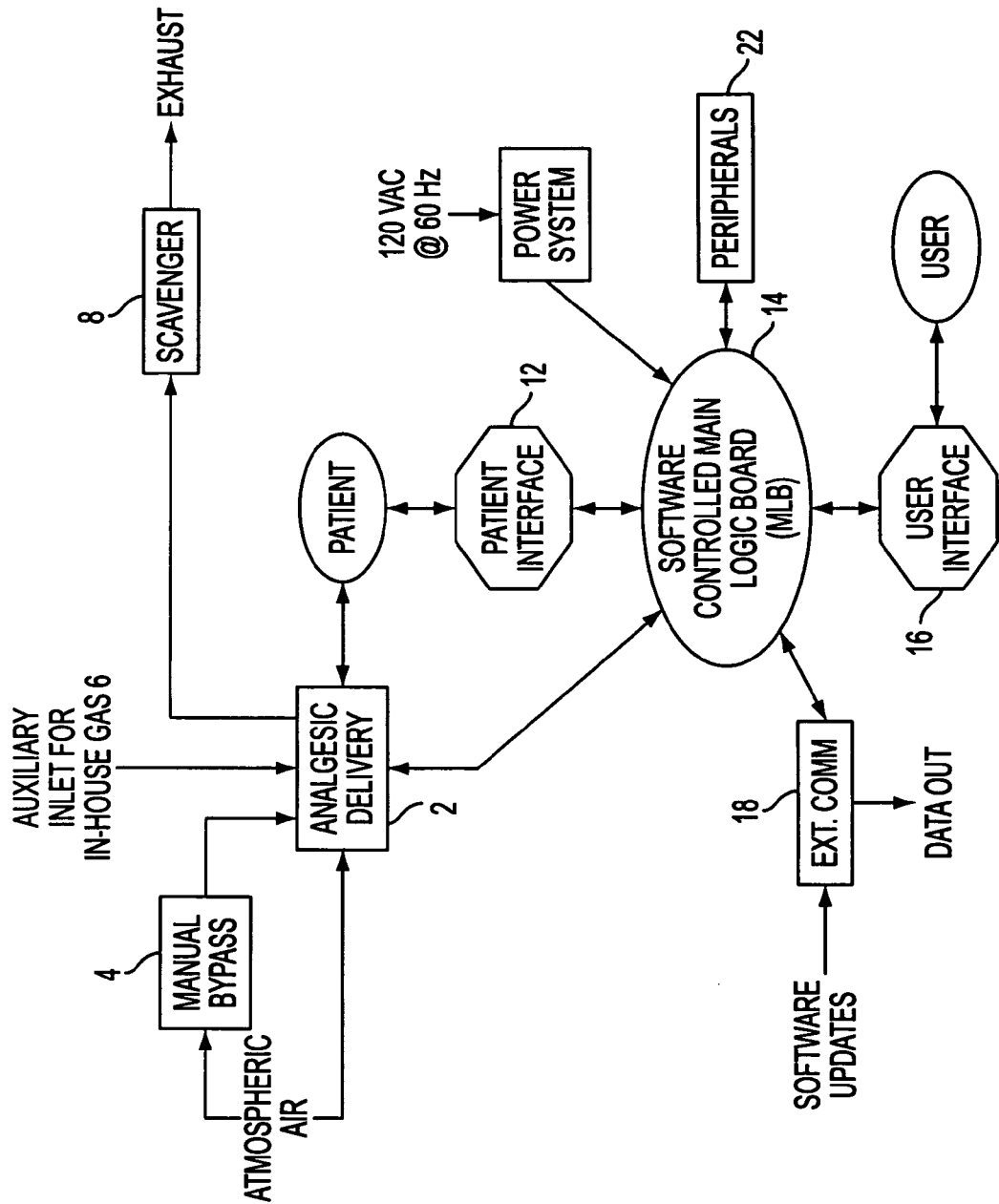
FIG. 5 depicts a preferred embodiment of the invention.

A block diagram of a preferred embodiment of a care system in accordance with the invention is depicted in FIG. 5. Analgesic delivery system 2 of FIG. 5 delivers a mixture of gaseous sedative, analgesic and/or amnestic drugs (such as nitrous oxide, sevoflurane or nebulized narcotics) and oxygen gas to the patient. Manual bypass circuit 4 (shown in further detail in FIG. 6 and FIG. 10A) is coupled to the manifold system portion of analgesic delivery system 2 and bypasses the source of analgesia enabling the manual control of delivery of atmospheric air to the patient. An auxiliary inlet 6 is provided to analgesic delivery system 2 and enables the provision of in-house supply of gaseous drug or oxygen to the delivery system 2. Scavenger system 8 (shown in detail in FIG. 10B) is coupled to analgesic delivery system 2 and collects exhaled gases from the patient and exhausts them to a safe location through exhaust hose 32 (FIG. 3B).

Patient interface system 12 includes one or more patient health monitors (these can be known vital sign monitors, such as non-invasive blood pressure monitors, or known pulse oximeters, capnometers, EKGs, etc.); means for monitoring the level of a patient's consciousness; and/or means for the patient to communicate with system 10 (FIG. 1), such as by requesting an increase or decrease in the dosage of drugs. One or more of these patient monitoring and request devices are electronically coupled to and, through A-D converters, provide feedback signals representing the patient's actual physiological condition and drug dosage requests to electronic controller 14. Controller 14 compares this electronic feedback received with data stored in a memory device, said data representing sets of one or more safe and undesirable patient physiological condition parameters (e.g., safe and undesirable $O_2$ saturation conditions, end tidal $CO_2$ levels and/or levels of patient consciousness). These sets of parameters are collectively referred to as a safety data set. Based on the comparison, controller 14 commands conservative application of drug delivery in accord with said parameters at safe, cost-effective optimized values.

Still referring to FIG. 5, user interface system 16 (described in more detail in FIGS. 18 and 22) displays electronic signal values stored in or provided to electronic controller 14, such values reflecting the status of one or more of the patient's physiological state, the patient's level of consciousness, and/or the status of various care system parameters. User interface system 16 includes devices that permit the nonanesthetist to interact with the care system via controller 14 (e.g., input patient information, pre-set drug dosages, silence alarms) such as keyboard 230 (FIG. 2) and/or remote control unit 45 (FIG. 1). Patient and care system information is displayed by means of graphical and numeric display devices, e.g., 35 (FIG. 1), LEDs incorporated into housing 15 (FIG. 1) and/or on remote control unit 45.

External communication devices 18 (also described in FIGS. 19A and 19B) enable the sending and/or receiving of electronic information signals to and from electronic controller 14 and external computers at remote locations or on local networks. Peripheral devices 22 such as door and temperature sensors, among others, communicate electronically with controller 14 to ensure the proper, safe and secure operation of care system 10.

The above systems overviewed in FIG. 5 are now described in more detail.

Figure 6:
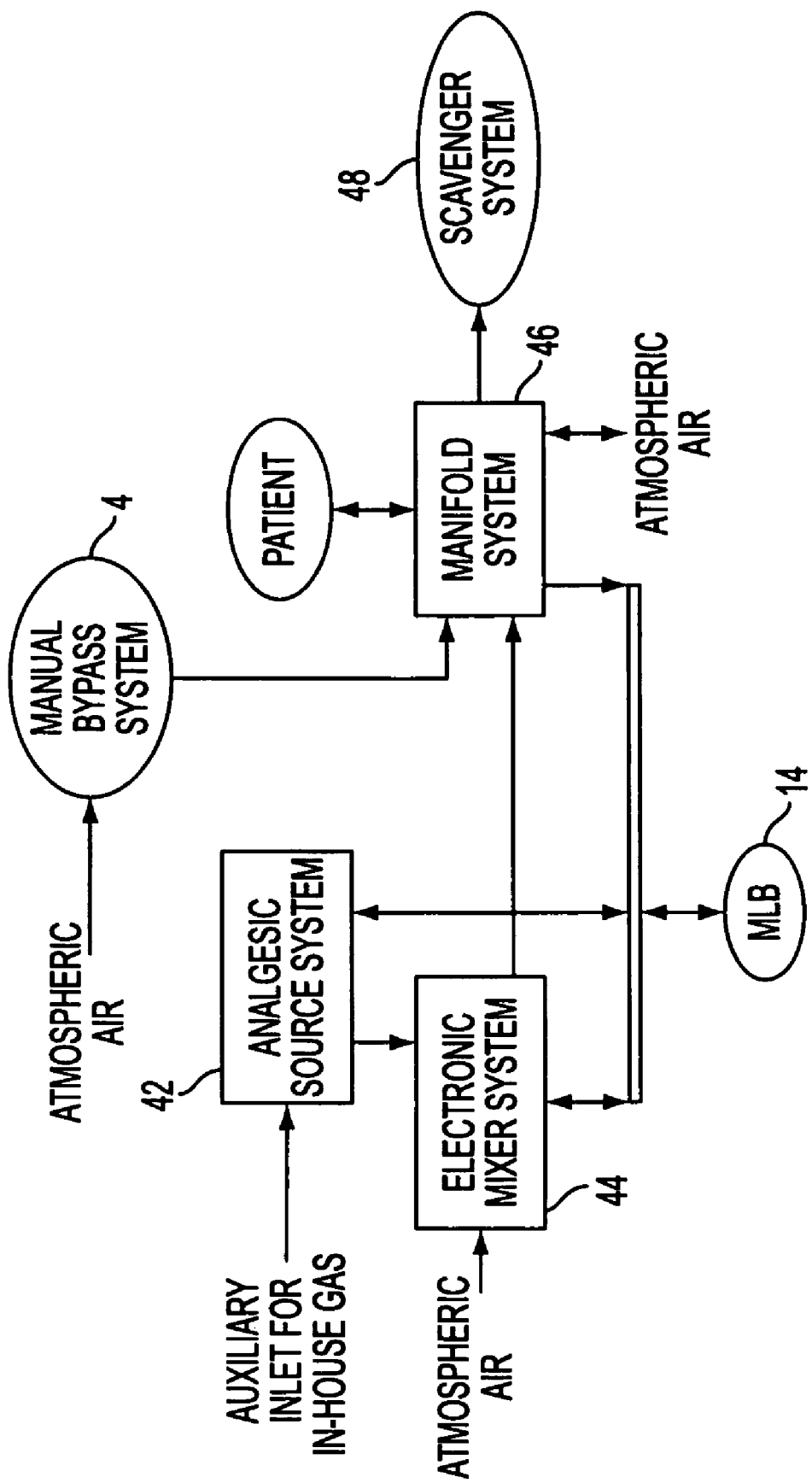
FIG. 6 depicts a preferred embodiment of a drug delivery system in accordance with the invention.

FIG. 6 shows in further detail an overview of a preferred drug delivery system 2 (FIG. 5) which provides a mixture of one or more sedative, analgesic and/or amnestic drugs in gaseous form; oxygen; and atmospheric air to a patient, the provision of each being independently adjustable (manually and via electronic controller 14) by the physician. The drug delivery system is comprised of a drug source system 42, an electronic mixer system 44 and a manifold system 46.

Drug source system 42 contains sources of one or more gaseous drugs and oxygen and is coupled through pneumatic lines to electronic mixer system 44. Drug source system 42 is also electronically coupled to electronic controller 14, and as is described below, contains sensors monitoring one or more operating states of drug source system 42 (e.g., whether the drug is flowing). Such monitored system information is converted to appropriate electronic signals and fed back to electronic controller 14 via the electronic coupling.

Electronic mixer 44 receives the one or more gaseous drugs, $O_2$ and atmospheric air through the pneumatic lines and electronically mixes same. Electronic mixer 44 is also electronically coupled to electronic controller 14 and also contains sensors that provide electronic feedback signals reflecting system operation parameters of mixer 44 to electronic controller 14. Mixer 44 includes electronic flow controllers with solenoid valves which receive flow control instruction signals from controller 14.

Manifold system 46 is coupled through pneumatic lines to and receives the one or more gaseous drugs, $O_2$ and air mixture from electronic mixer 44 and delivers the mixture to the patient via airway circuit 20 (FIG. 1) and face mask 30 (FIG. 1). Manifold system 46 is also electronically coupled to electronic controller 14 and includes sensors that provide electronic feedback signals reflecting manifold system 46 operation parameters to controller 14. Manifold 46 delivers patient exhaled gases to a scavenging system 48 for exhaust to a safe location via exhaust hose 32 (FIG. 3B).

Figure 7A:
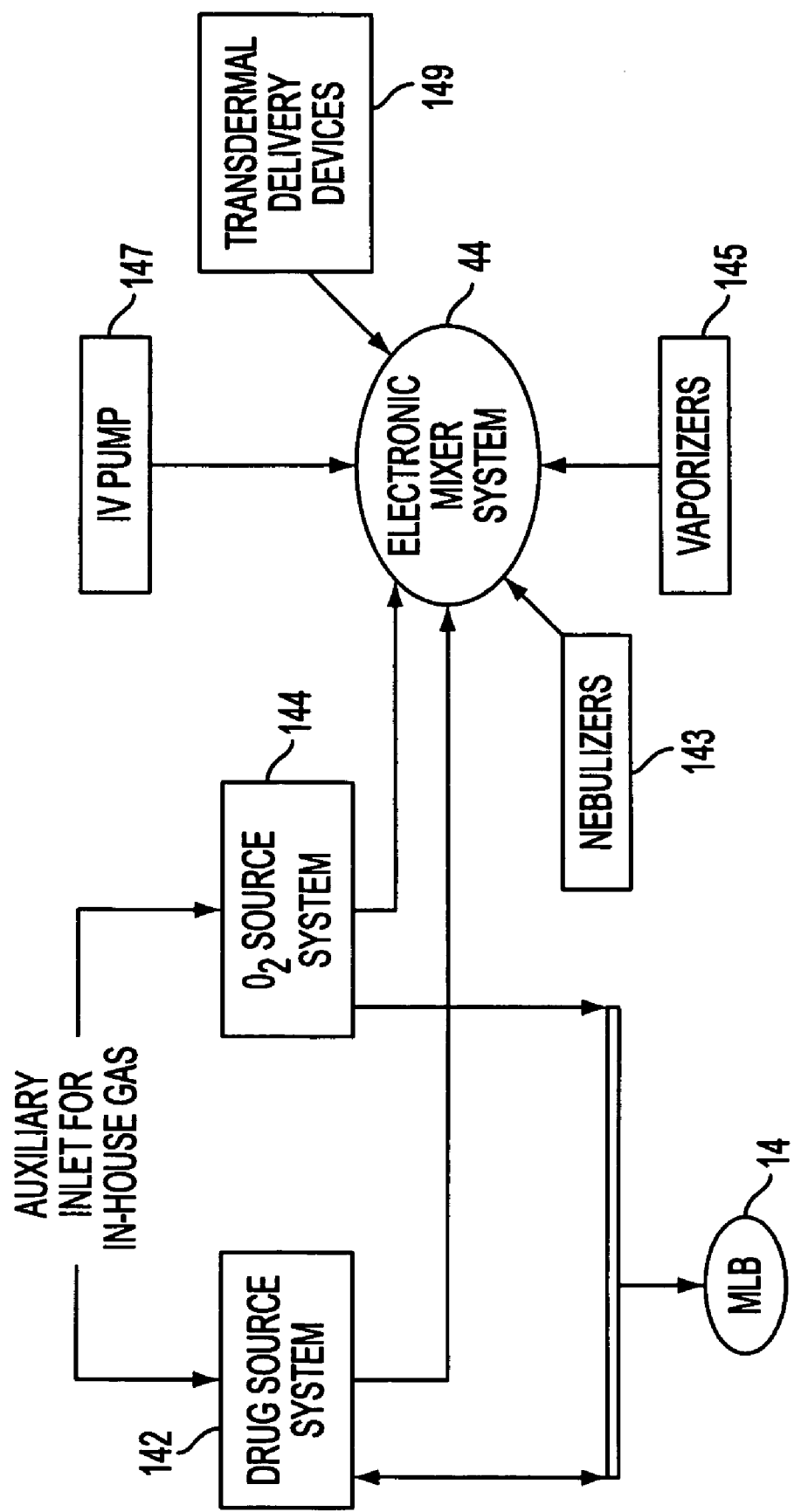
FIGS. 7A–7C depict the details of a preferred embodiment of the drug source system in accordance with the invention.
Figure 7B:
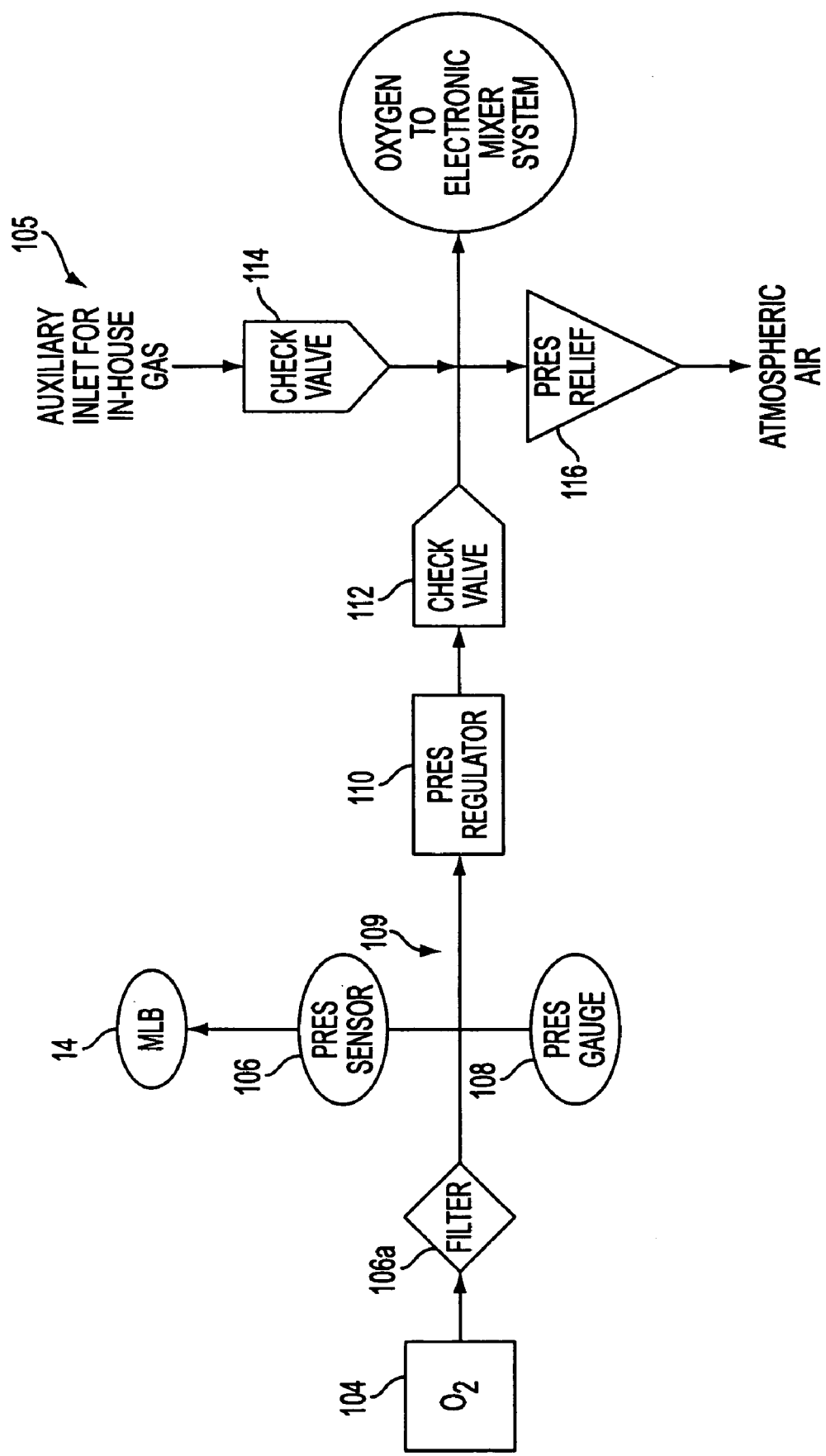
Figure 7C:
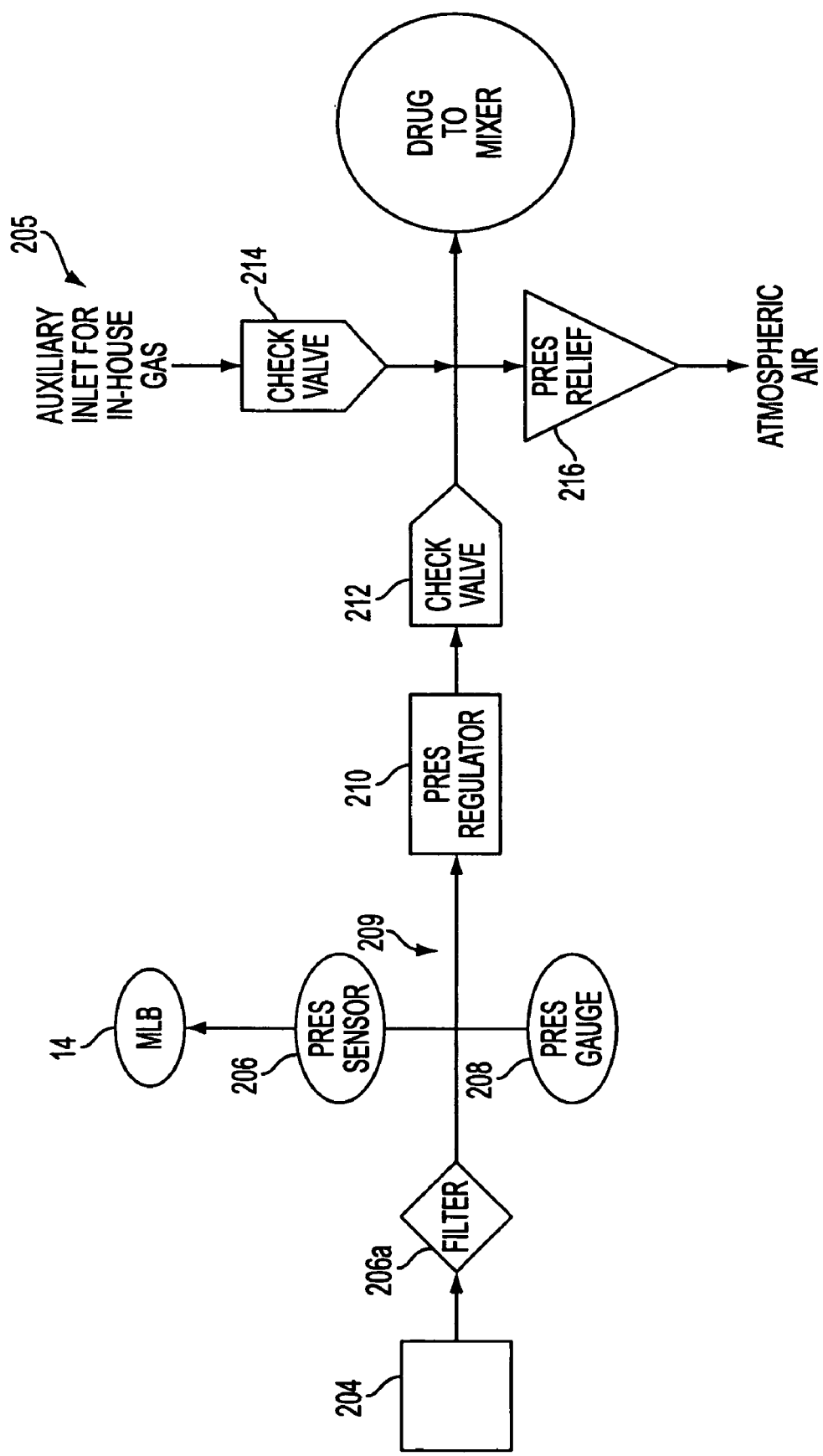

Drug source system 42 is shown in further detail in FIGS. 7A–7C. Referring to FIG. 7A, analgesic source system includes drug source system 142 which provides a source of one or more sedative, analgesic and/or amnestic drugs; and an oxygen source system 144 which provides a source of oxygen. In aspects of this invention where the drugs are in gaseous form, the sources of drugs and oxygen provide the gases at low pressure, and can be tanks contained within housing 15 (FIG. 1) such as those shown at numeral 54 in FIG. 2 or an in-house source. The ability to use alternative sources increases the useability of the care system of the invention because the system can function as a source-dependent unit within rooms with access to in-house gas supplies or as a self-contained unit within rooms that do not have in-house gas connections.

In additional aspects of the invention, drug source system 42 can include one or more of the following: known nebulizers 143 which enable the delivery of aerosolized drugs, such as morphine, meperidine, fentanyl and others; known vaporizers 145 which enable the delivery of halogenated agents, such as sevoflurane; known infusion pump-type drug delivery devices 147 or known transdermal-type drug delivery devices 149 (including ion transfer based devices) to enable the delivery of drugs such as propofol, remifentanil, and other infusible drugs by continuous or bolus administration.

FIG. 7B details the oxygen source system and shows an oxygen tank or other source of oxygen 104 and a pneumatic oxygen line 109 for delivering oxygen gas to electronic mixer system 44 (FIG. 7A). Filter 106a in oxygen line 109 removes contaminants within the oxygen stream from oxygen source 104. Pressure sensor 106 (which may be of a type known and currently available) in oxygen line 109 monitors the pressure in oxygen source 104 generating a signal reflecting same and thereby indirectly measuring the amount of oxygen remaining. Pressure sensor 106 is electronically coupled to electronic controller 14 and forwards signals reflecting the measure of pressure in the oxygen source to controller 14. In a preferred embodiment, electronic controller 14 receives the signal from pressure sensor 106 and through software accesses data parameters stored in a memory device. The parameters reflect one or more setpoints establishing safe and undesirable operating conditions of O2 operating pressure. Controller 14 compares the actual O2 pressure to the stored parameter set point data. If the comparison reveals that the O2 pressure is outside of an established safe range as established by the stored data, an alarm or other attention-commanding device activates and if same is not manually deactivated, electronic controller 14 instructs the flow of drug delivery to reduce to a pre-set safe amount (or cease). The operation of the software control vis-a-vis system state monitors is described in more detail in connection with FIGS. 21A and 23A.

The signal obtained from oxygen source pressure sensor 106 can be related to the user via display devices (e.g., 35, FIG. 2) in terms of the time remaining under present use so that the user can ascertain if the procedure can be completed. The user is immediately notified if the pressure falls out of the normal operating conditions by an alarm, display device or other suitable attention-commanding device. Pressure gauges 108 visually display to the user the oxygen source pressure obtained by sensor 106. Pressure regulator 110, which may be of a known solenoid type currently available or other suitable regulator, enables the reduction of pressure in oxygen source 104 to a reasonable operating pressure to provide flow of $O_2$ to the patient. Check valve 112 (check valves may be of a standard one-way type), in oxygen line 109 downstream of regulator 110 prohibits backward flow of the patient's exhalations and ensures that such back-flow does not damage or contaminate regulator 110 and oxygen source 104. In systems where an in-house oxygen source 105 is used, remote check valve 114 ensures that back-flow from the patient's exhalations does not damage or contaminate in-house oxygen source 105. Pressure relief valve 116 exhausts oxygen to the atmosphere if the pressure in oxygen line 109 exceeds safe operating values pre-programmed into electronic controller 14.

FIG. 7C details the drug source system and in a preferred embodiment includes a tank or other source of drug 204 and a pneumatic line 209 for delivering gaseous drugs to electronic mixer 44. Filter 206a in drug line 209 removes contaminants within the drug stream from drug source 204. Pressure sensor 206 (which may be of a type known and currently available) in drug line 209 monitors the pressure in drug source 204 generating a signal reflecting same and thereby indirectly measuring the amount of drug. Pressure sensor 206 is electronically coupled to electronic controller 14 and forwards signals reflecting the measure of pressure in the drug source to controller 14. As is described above in connection with oxygen source pressure sensor 106 and in FIGS. 21A and 23A, in a preferred embodiment controller 14 receives the signal from sensor 206 and through software accesses stored data parameters reflecting safe and undesirable operating conditions of drug source pressure and conservatively controls drug delivery in accord with said stored parameters.

The signal obtained from the drug source pressure sensor 206 can be related to the user via display devices (e.g., 35, FIG. 2) in terms of the time remaining under present use so that the user can ascertain if the procedure can be completed. The user is immediately notified via an alarm, display device or other suitable attention-commanding device if the pressure falls out of the normal operating conditions. Pressure gauges 208 visually display to the user the drug source pressure obtained by sensor 206. Pressure regulator 210, which may be of a known solenoid type currently available, enables the reduction of pressure in drug source 204 to a reasonable operating pressure to provide flow of drug to the patient. Check valve 212 in drug line 209 downstream of regulator 210 prohibits backward flow of the patient's exhalations and ensures that back-flow from the patient's exhalations does not damage or contaminate regulator 210 and drug source 204. In systems where an in-house drug source 205 is used, remote check valve 214 ensures that back-flow from the patient's exhalations does not damage or contaminate in-house drug source 205. Pressure relief valve 216 exhausts the drug to the atmosphere if the pressure in drug line 209 exceeds safe operating values pre-programmed into electronic controller 14.

To increase safety, the known pin indexed safety system (P.I.S.S.) and/or diameter indexed safety system (D.I.S.S.) may be used for all $O_2$ source and line fittings where appropriate for tank and/or in-house sources. This ensures, for example, that oxygen source 104 is not mistakenly attached to the drug line 209 and vice versa.

Figure 8:
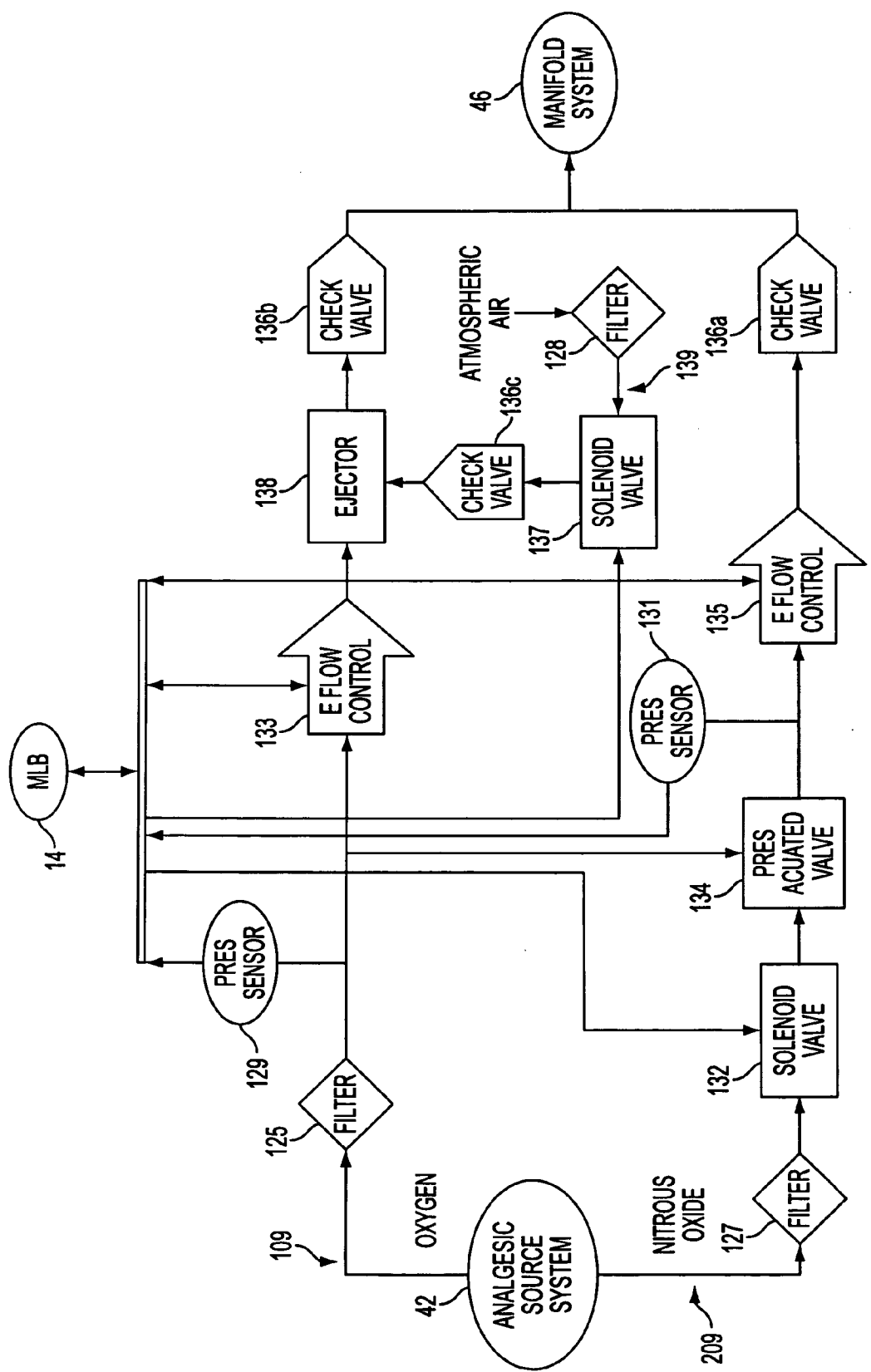
FIG. 8 depicts a preferred embodiment of an electronic mixer system in accordance with the invention.

FIG. 8 details a preferred electronic gas mixer system which electronically mixes gaseous drugs and oxygen so that the precise flow rate of gaseous drug and oxygen is delivered to the patient. The use of the electronic mixer system of this invention increases the operational safety of the apparatus of the invention because, as described below, the volume of drug delivery can be electronically controlled in closed-loop fashion by currently available electronic flow controllers which include solenoid type valves which, in response to command signals from electronic controller 14, halt or reduce the flow of drugs to the patient in the event of an occurrence of unsafe patient or system conditions. Specifically, pneumatic oxygen line 109 and drug line 209 from analgesic source system 42 deliver gaseous drugs and oxygen to filters 125 and 127 in lines 109 and 209, respectively, which filter contaminants from lines 109 and 209. System state monitors, namely, pressure sensors 129, 131, monitor the oxygen and gaseous drug line pressures, respectively, and transmit signals reflecting said pressures to electronic controller 14, which conservatively controls drug delivery in accord with a stored data set containing parameters reflecting one or more safe and undesirable system operation states as described above and in FIGS. 21A. and 23A. Also, if any of the pressures fall out of the norm, electronic controller 14 immediately alerts the user, for example, by means of signaling an alarm device.

Electronic flow controllers 133, 135, which may be of a known type currently available including solenoid valves, are electronically coupled to and receive instruction signals from electronic controller 14 which has been programmed with and/or calculates a desired flow rate of oxygen and drug. Programmed flow rates may be those input by the physician user employing traditional choices regarding drug administration amounts and rates, including in IV embodiments, target controlled infusion principles, among others. Calculated flow rates may be arrived at through conservative decision-making software protocols including comparison of actual patient physiological condition feedback values with stored data representing safe and undesirable patient physiological conditions. Drug delivery is effected at the rates calculated in a closed, control-loop fashion (described in more detail below) by flow controllers 133, 135. Drug administration may be a combination of one or more physician inputs and/or electronic flow rate calculations based on patient and system state parameters; flow controllers may respond to instruction signals initiated by electronic controller 14 or by the physician.

Flow controllers 133, 135 receive instruction signals from controller 14 reflecting the electronic output of both system state monitors (such as pressure sensors 106, 206 described above) and patient state monitors. Flow controllers 133, 135, in response to instruction signals from controller 14, may curtail or cease flow of drug delivery when system state and/or patient health monitors indicate to controller 14 that failures in the operation of care system 10 have occurred, that system 10 is otherwise operating outside of an established safe state, or that a patient's physiological state (e.g., vital signs or consciousness level) has deteriorated to an unsafe condition.

As the invention includes both intravenous and gaseous, among other forms of drug delivery, such embodiments may also include known electronic flow controllers coupled to electronic controller 14 and responsive to instruction signals from controller 14 reflecting both patient and system states.

Referring again to FIG. 8, solenoid valve 132 is electronically coupled to electronic controller 14 and must be activated by same before drug will flow through line 209. In the event of system power failure, drug delivery will be halted due to the fail-closed nature of solenoid valve 132. This is described, for example, in FIG. 21A which shows that if a system state monitor indicates power failure, alarm type "2" sounds to alert the nonanesthetist and drug delivery is halted (i.e., reduced to 0%).

Moreover, pressure actuated valve 134 in drug line 209 responds to the amount of pressure in $O_2$ line 109 and permits flow of gaseous drug only if sufficient oxygen flows through oxygen line 109. Check valve 136a in drug line 209 ensures that the flow of gaseous drug to manifold system 46 is one-way and that there is no back-flow. Check valve 136b in oxygen line 109 ensures one-way flow of $O_2$ to manifold system 46 with no back-flow.

In atmospheric air line 139, air inlet solenoid valve 137 is electronically coupled to and activated by electronic controller 14 and if activated permits atmospheric air to be mixed with the oxygen gas by means of air ejector 138. Air ejector 138 injects a fixed ratio of atmospheric air into oxygen line 109. Filter 128 removes contaminants from air line 139 and check valve 136c ensures one-way flow of air from solenoid valve 137 to ejector 138 with no back-flow.

Figure 9A:
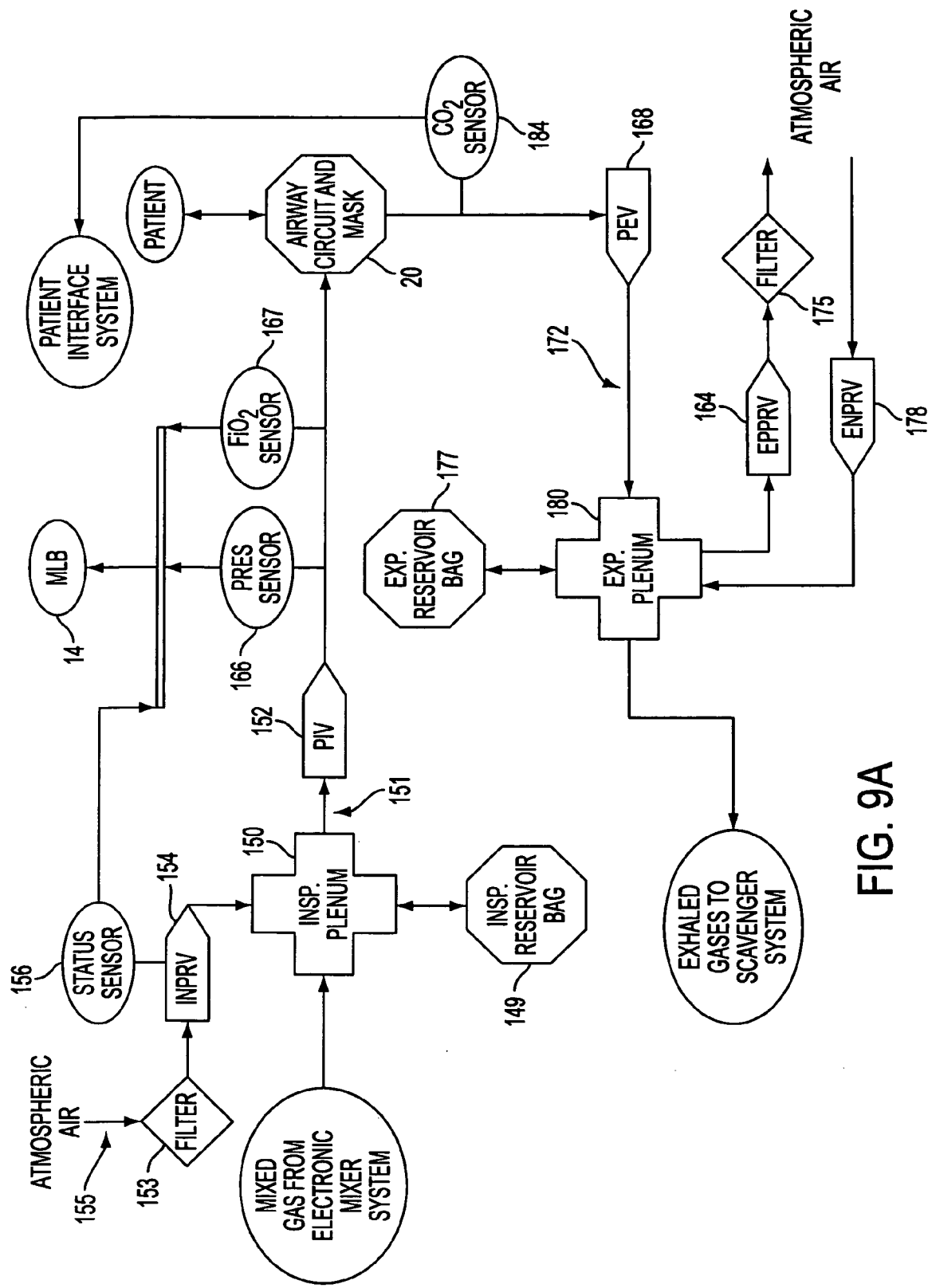
FIG. 9A depicts one embodiment of a manifold system in accordance with the invention.

Referring to FIG. 9A which details one embodiment of manifold system 46 (FIG. 6), the drug/$O_2$ gas mixture from electronic mixer system 44 (FIG. 6) enters manifold system 46 and flows into inspiratory plenum 150 from which it proceeds through inspiratory line 151 to primary inspiratory valve (PIV) 152 and eventually to airway circuit 20 and mask 30 (FIG. 1). Primary inspiratory valve 152 permits one-way flow of said gas mixture and ensures that exhaled gases from the patient do not enter the inspiratory side of manifold system 46 (FIG. 6), thereby guarding against possible contamination. Atmospheric air may be permitted to enter inspiratory line 151 through an inspiratory negative pressure relief valve (INPRV) 154 which allows one-way flow of atmospheric air to reach the patient if a significant negative vacuum is drawn on the inspiratory side of manifold system 46 (e.g., the patient inhales and receives no or insufficient oxygen). INPRV 154 thereby essentially permits air on demand by the patient. INPRV filter 153 removes particulates which may be in air line 155 or present in the atmosphere. INPRV status sensor 156 (which may be of a known pressure, temperature, infra-red or other suitable type) monitors the extent of open/close status of INPRV 154 and generates a signal which is converted to an appropriate electronic (digital) signal and communicates the status of INPRV 154 to electronic controller 14. During the exhalation phase of the patient's breathing cycle, inspiratory reservoir bag 149 collects the drug/$O_2$/air mixture which the patient will draw on the next inhalation phase.

Still referring to FIG. 9A, pressure sensor 166 measures pressure in airway circuit 20 (FIG. 1) and is used to indicate airway flow, i.e., if the primary inspiratory valve (PIV) 152 or the primary expiratory valve (PEV) 168 is occluded. For example, if sensor 166 reads a high pressure that indicates that PEV 168 is blocked, whereas a low pressure indicates PIV 152 is blocked. Airway circuit 20 (FIG. 1) also contains a fraction of inspired oxygen ($FIO_2$) sensor 167 (which may be of a known type currently available) which measures the oxygen percentage of gas contained in the mixture delivered to the patient, and thus guards against the possibility of delivering a hypoxic mixture to the patient (i.e., a drug/$O_2$ mixture that does not provide enough $O_2$ to the patient). INPRV status sensor 156, pressure/airway flow sensor 166, and $FIO_2$ sensor 167 are electronically coupled to and provide electronic feedback signals reflecting system state parameters to electronic controller 14. As described in FIGS. 21A and 23A, controller 14, through software and/or logic, effects a comparison of the signals generated by these system monitors with a stored data set of system parameters established by setpoints and/or logic-type data reflecting safe and undesirable system operating states, and conservatively controls (e.g., reduces or halts) drug delivery if the comparison determines that care system 10 is operating outside of a safe range.

Airway circuit and mask (20, FIG. 9) interface with the patient to provide a closed circuit for the delivery of drug/$O_2$ gas mixture to the patient. It should be recognized that embodiments of the subject invention in which the drugs are delivered in a form other than compressed gas, such as intravenously or transdermally, may not include face masks, airway circuit features and other aspects associated with delivery of drugs in gaseous form. Where the drug is delivered in gaseous form and an airway circuit and face mask are employed, such face mask and attendant airway circuitry and other features such as the scavenging system may be in the form of that described in U.S. Pat. No. 5,676,133 issued to Hickle et al. and entitled Expiratory Scavenging Method and Apparatus and Oxygen Control System for Post-Anesthesia Care Patients. (With respect to such embodiments, the specification of Hickle et al. is incorporated herein by reference.)

In preferred embodiments the mask is disposable and contains means for sampling the $CO_2$ content of the patient's respiratory airstream and, optionally, means for also measuring the flow of the patient's airstream and/or means for acoustical monitoring. The sampling of the $CO_2$ in the patient's airstream may be done by means of a capnometer or a lumen mounted within the mask through a port in the mask, and placed close to the patient's airway. A second lumen similarly mounted within the mask could be used to measure the airflow in the patient's airstream. This airflow measurement could be accomplished by a variety of currently available devices, including for example, devices that measure the pressure drop in the airstream over a known resistance element and thereby calculate the airflow by known formula. The means for acoustical monitoring may be a lumen placed within the mask with a microphone affixed within that lumen. The microphone would permit recording, transducing and playing out through an amplifier the audible sound of the patient's breathing. It is noted that the lumen for acoustical monitoring could be a separate lumen or could be combined with the lumen for calculating the flow of the patient's airstream. It is further noted that it is important to place the lumens, especially the $CO_2$ sampling lumen, close to the patient's open airway and to ensure such lumens remain close to the patient's airway.

Referring again to FIG. 9A, primary expiratory valve (PEV) 168 in expiratory line 172 ensures one-way flow of a patient's exhaled gases to scavenger pump system 48, thus, prohibiting any back-flow from gases exhaled to the scavenger system from reaching the patient. Importantly, PEV 168 guards against the re-breathing of exhaled carbon dioxide. As is easily seen, the manifold 46 and airway circuit 20 of a preferred embodiment of this invention permit one-way airway flow only. That is, unlike prior devices that employ circular airway circuits (which require $CO_2$ absorbent material to permit re-breathing of exhaled air), there is no re-breathing of exhaled gases in this embodiment of the invention.

In the embodiment of the invention shown in FIG. 9A, expiratory positive pressure relief valve (EPPRV) 164 in expiratory line 172 allows exhaled gases to escape to the atmosphere if sufficient positive pressure develops on the expiratory side of the manifold system. This could happen, for example, if the patient is exhaling, but scavenger system 48 (FIG. 6) is occluded or otherwise not working properly. EPPRV filter 175 downstream of EPPRV 164 filters contaminants from the expiratory stream flowing through EPPRV 164 prior to the stream entering the atmosphere. Expiratory negative pressure relief valve (ENPRV) 178 is a one-way valve that allows atmospheric air to be drawn into expiratory plenum 180 and then on to scavenger system 48 if sufficient vacuum pressure is drawn on the expiratory side of manifold system 46. This could happen, for example, if the vacuum pump of scavenger system 48 is set too high or PEV 168 is blocked. Expiratory reservoir bag 177 collects exhaled gases from the patient during exhalation via expiratory plenum 180. These gases will be exhausted by scavenger system 48 during the next patient inhalation phase. As is described in detail below, patient vital sign monitor, such as a capnometer 184, monitors the amount of $CO_2$ in the patient's exhaled gases and provides electronic feedback signals reflecting the level of $CO_2$ in the patient's exhalations to controller 14. Other types of ventilatory monitors such as an airflow measure, IPG device or an acoustical monitor could also be used to provide electronic feedback signals reflecting patient health parameters to controller 14.

Figure 9B:
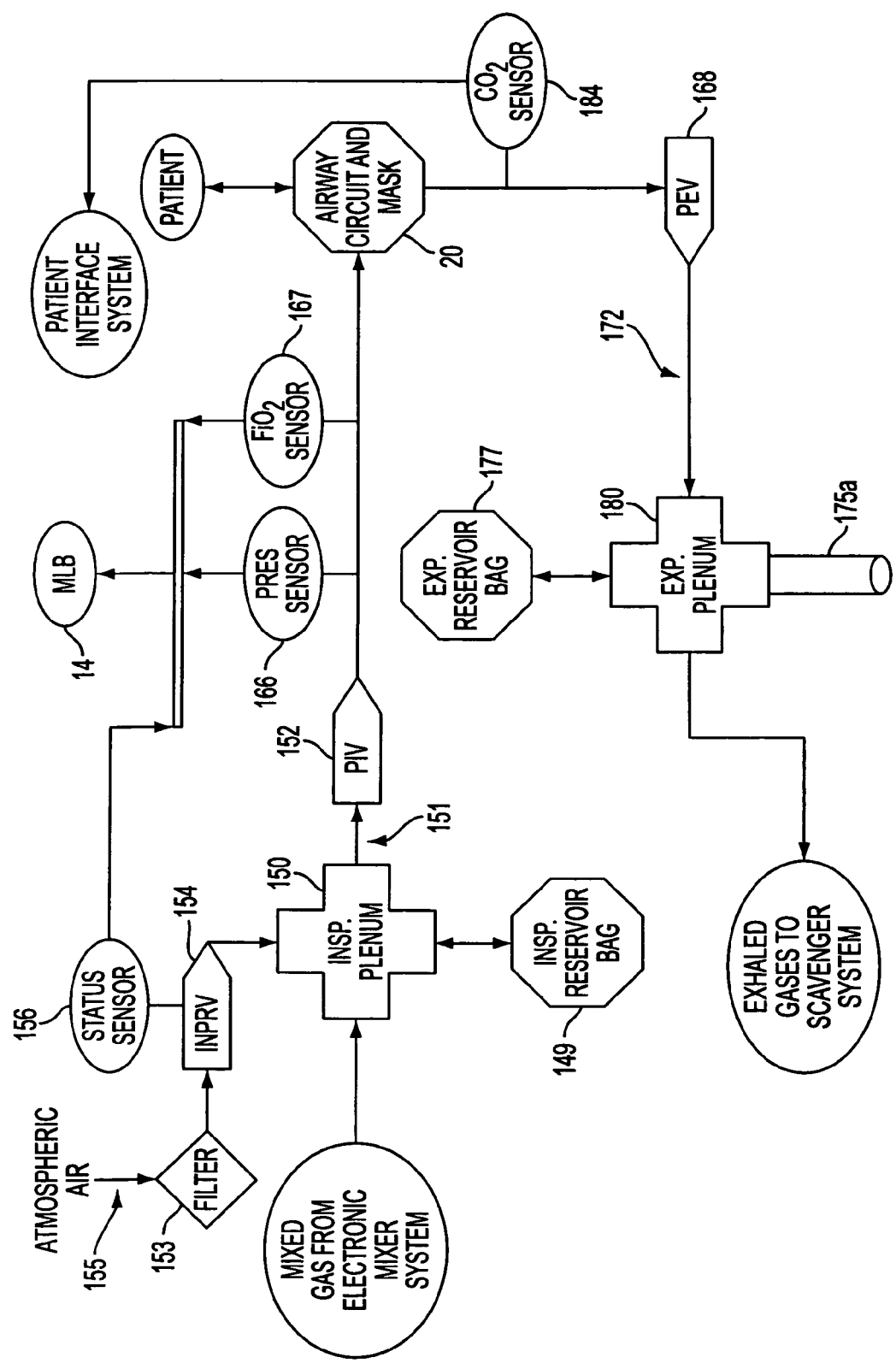
FIG. 9B depicts a second embodiment of a manifold system in accordance with the invention.

In an alternative preferred embodiment shown in FIG. 9B, ENPRV 164, filter 175 and ENPRV 178 are eliminated. A long pipe or similar conduit 175a, interconnected with reservoir bag 177 and opening to atmospheric air, is substituted therefor. The elimination of the valves 164 and 175 provides for a more cost efficient and simple system, while the substituting of the pipe 175a still ensures that if the scavenger system 48 is occluded, is set too high, is otherwise not working or if PEV 168 is blocked, that there is still access to atmospheric air, and the patient may breath into the room or air may come into the system. A highly compliant reservoir bag 179 also assists in catching excess flow of exhaled air. In this simplified embodiment, there are essentially only three valves, PIV 152, PEV 168 and INPRV 154.

As is described above, system valves PIV 152 and PEV 168 ensure one-way flow of inspired and expired gases. The patient cannot re-breathe exhaled gases and no contaminants are allowed to enter the source system. The valve system INPRV 154, EPPRV 164, and ENPRV 178 (or the alternate INPRV 154 and pipe) provides a system fail-safe. If analgesic source system 42 (FIG. 6) or scavenging system 48 (FIG. 6) is functioning improperly, the valves will open and allow the patient to breath without significant effort. The system state sensors 156, 166 and 167 monitor system operation such as INPRV valve status, gas pressure and fraction of inspired oxygen, and electronically feed back signals reflecting the operating status of those operations to microprocessor controller 14 to ensure safe operation of the apparatus.

It is noted that the valves and sensors between INPRV 154 and ENPRV 178 in a preferred embodiment of manifold system 46 can be considered a system state monitoring system because there are no valves controlled by the software of electronic controller 14. At this point in the care system 10, the gas has already been mixed and the volume determined by the flow controllers 133, 135 (FIG. 8). Manifold system 46 (FIG. 6) provides at least two basic services, sensor inputs for $FiO_2$ and $CO_2$ (167, 184 of FIG. 9) and flow status derived from flow sensor 166 (FIG. 9).

The determination of appropriate drug delivery/flow percentages by controller 14 can be accomplished through a variety of methods. Initial drug administration amounts and rates may be selected and input by the physician employing traditional methods. Physicians may also employ pharmacokinetic/pharmacodynamic modeling to predict resulting drug concentrations and their effect based on physician choices, but not permit automatic changes to drug concentrations without instructions from the physician. In intravenous embodiments known target-controlled infusion techniques may be employed where the physician selects a desired (targeted) blood serum or brain effective site concentration based on such patient parameters as height, weight, gender and/or age.

During operation of the system when an internal or external event occurs, such as the activation of a system or patient health monitor alarm or a physician or patient request for increased drug, electronic controller 14 determines the desired amount of intravenous drug (or fractional amount of $O_2$, gaseous drug and air in the total gas flow) as the function of such event. The actual IV drug concentrations (or gaseous drug/$O_2$/air fractions) are then calculated. These actual calculated amounts will not always be the same as those requested (e.g., by the user, patient or system) because of the often complex relationship between drug or drug and gas mixtures. In sum, drug mix fractions are typically calculated when, for example, an alarm levels change, alarm time-outs occur (e.g., there is no silencing of an initial alarm by the user), a user requests a change, the patient requests a change, when a procedure begins (system resorts to default values) and when a controller clock triggers.

In a preferred embodiment of the invention delivering gaseous drugs, flow controllers in mixer 44 (detailed in FIG. 8) determine the total fresh gas flow (FGF) which is the sum of the volumes of each gas being controlled, namely, the gaseous drug, oxygen and atmospheric air. Solenoid valves are opened proportionally to achieve the desired FGF and fractional amount of each gas. Flow controllers 133, 135 close the feedback loop on the gas fractions by measuring the $FiO_2$ and fraction of inspired gaseous drug in the manifold system 46 and adjusting the mixer solenoid valves accordingly.

In one aspect of the invention, the flow controllers 133, 135 match the FGF with patient minute ventilation rates. The minute ventilation rate is the volume of breath one inhales and then exhales (e.g., in cubic centimeters or milliliters) in one minute. A patient's respiratory physiology is balanced at this minute ventilation. The care system optimizes FGF rates by matching gas delivery to patient minute ventilation rates. This conserves gas supplies, minimizes the release of anesthesia gases into the operating environment, and helps balance respiratory function. For example, if the FGF is less than the minute ventilation, INPRV 154 will open to supplement the air flow (INPRV 154 being a mechanical system not under electronic control).

In an additional aspect of the invention, the care system will not only measure and monitor minute ventilation as described above, but also "effective minute ventilation" and thereby improve the quantitative information about patient physiology considered by the system. "Effective minute ventilation" is a term used herein to mean the amount of gas that is actually involved in respiratory gas exchange between the alveolar sacs of the lungs and the capillary blood surrounding those sacs (as opposed to simply the volume of gas one inhales and then exhales, "tidal volume"). This measure may be arrived at by subtracting the volume of anatomical space imposed between the air source (e.g., mouth) and the transfer of gas at the alveolar sacs (estimated from the patient's height and weight), from the tidal volume of gas to arrive at "effective tidal volume." The effective tidal volume is then multiplied by respiratory rate to arrive at "effective minute ventilation."

FIG. 10A details manual bypass system 4 (FIG. 5) which is coupled to manifold system 46. The bypass system 4 includes a self-inflating resuscitation bag (SIRB) 19a (also shown in FIG. 3B) which is a manual pump with which the user can provide air intermittently to the patient through a bypass air line 90. A quick disconnect type fitting 91 (such as that disclosed in Hickle above) couples SIRB 19a with manifold system 46 and provides rapid attachment thereto. A manual flow control valve 92 opens or closes bypass air line 90. When line 90 is open, manual flow control valve 92 can be adjusted to provide the necessary air flow. A flow meter 94 placed in bypass air line 90 provides a visual display to the user of the status of air flowing through the bypass air line 90. The above-described manual bypass system 4 provides the patient with manually-controlled flow of air and thus enables air delivery in the case of an oxygen source system 144 (FIG. 7A) failure.

FIG. 10B details scavenger pump system 48 (FIG. 6) which is integrated into the care system and vacuums exhaled gases from manifold system 46 through a scavenging line 85. A filter 86 in scavenging line 85 removes contaminants from the gases which have been exhaled from the patient and which are flowing through the scavenger line 85. Pressure regulator 87 receives the filtered gases and ensures that the vacuum pressure is maintained in vacuum pump 95 downstream at a reasonable working level. Flow restrictor 88 sets the flow rate through the vacuum 95 for a given vacuum pressure. Check valve 89 downstream of flow restrictor 88 provides one-way flow of scavenged gases, and thus ensures that back-flow does not inadvertently flow into scavenger system 48 from the vacuum pump 95 downstream. Vacuum pump 95 provides the vacuum pressure necessary for scavenging of exhaled gases from the patient. The pump may be of an electrical type that can be powered by office standard AC current. As the vacuum pump is integrated into the care system, a wall vacuum source (such as that typically in an OR) is not required. Once the gases are vacuumed off, they are exhausted via exhaust hose 32 (FIG. 3B) to an appropriate area. The benefit of scavenging system 48 is at least two-fold in that the system helps assist the patient in the work of breathing and work environment safety is increased.

In a preferred embodiment, an emesis aspirator 19 (FIG. 3B) is integrated into system 10 and may be stored within housing 15. Emesis aspirator 19 is a manually operated device used to suction a patient's airway in the event of vomiting. Emesis aspirator 19 does not require an external vacuum source (e.g., wall suctioning) or electrical power for operation.

To enhance the safety of the invention, housing 15 may include structure integrated adjacent or otherwise near where emesis aspirator 19 is stored within housing 15 (FIG. 3B) to hold and prominently display containers of drugs capable of reversing the effects of various sedatives/analgesics. These "reversal drugs," such as naloxone, remazicon and others may be immediately administered to the patient in the event of an overdose of sedative, analgesic and/or amnestic.

Figure 11:
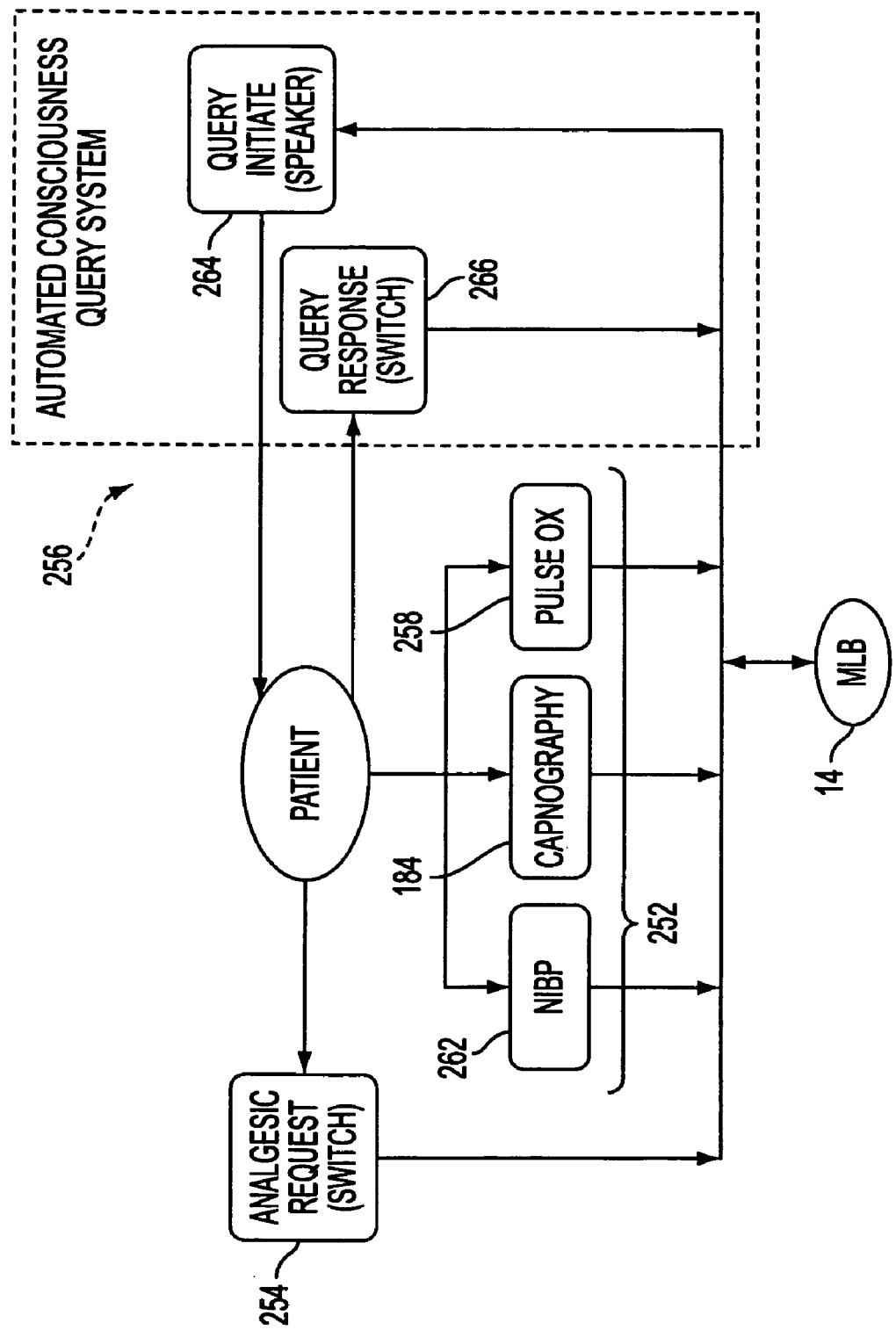
FIG. 11 depicts a preferred embodiment of a patient interface system in accordance with the invention.

Referring to FIG. 11, a preferred embodiment of the invention includes an integrated patient interface system which combines one or more patient health monitors 252 (additional health monitors to those shown are also contemplated by the invention) with additional automated patient feedback devices including a patient drug dosage increase or decrease request device 254 and an automated consciousness query system 256 for monitoring a patient's level of consciousness. These health monitors 252 and automated patient feedback devices 254, 256 are electronically coupled to electronic controller 14 via leads (e.g., 50, FIG. 2) and provide electronic feedback values (signals) representing the patient's physiological condition to controller 14. Generally, if any monitored patient parameter falls outside a normal range (which may be preset by the user or otherwise preprogrammed and stored in memory device as described above), the nonanesthetist is immediately alerted, for example, by an alarm, display or other attention-commanding device. The information obtained from patient health monitors 252 is displayed on a display device 35 (FIG. 2), in, for example, continuous wave form or numerics on LEDs, thus allowing the procedural physician to immediately gain useful information by reviewing the display device. Preferred embodiments of displays contemplated by the invention are described in more detail below.

A preferred embodiment of one aspect of the invention integrates drug delivery with one or more basic patient monitoring systems. These systems interface with the patient and obtain electronic feedback information regarding the patient's physiological condition. Referring to FIG. 11, a first patient monitoring system includes one or more patient health monitors 252 which monitor a patient's physiological conditions. Such monitors can include a known pulse oximeter 258 (e.g., an Ohmeda 724) which measures a patient's arterial oxygen saturation and heart rate via an infra-red diffusion sensor; a known capnometer 184 (e.g., a Nihon Kohden Sj5i2) which measures the carbon dioxide levels in a patient's inhalation/exhalation stream via a carbon dioxide sensor and also measures respiration rate; and a known non-invasive blood pressure monitor 262 (e.g., a Criticon First BP) which measures a patient's systolic, diastolic and mean arterial blood pressure and heart rate by means of an inflatable cuff and air pump. A care system constructed in accordance with this invention may include one or more of such patient health monitors. Additional integrated patient health monitors may also be included, such as, for example, a measure of the flow in a patient's airstream, IPG ventilatory monitoring, a standard electrocardiogram (EKG) which monitors the electrical activity in a patient's cardiac cycle, an electroencephalograph (EEG) which measures the electrical activity of a patient's brain, and an acoustical monitor whose audio signals may be processed and provided to controller 14 and amplified and played audibly.

A second patient monitoring system monitors a patient's level of consciousness by means of an automated consciousness query (ACQ) system 256 in accordance with the invention. ACQ system 256 comprises a query initiate device 264 and a query response device 266. ACQ system 256 operates by obtaining the patient's attention with query initiate device 264 and commanding the patient to activate query response device 266. Query initiate device 264 may be any type of a stimulus such as a speaker which provides an auditory command to the patient to activate query response device 266 and/or a vibrating mechanism which cues the patient to activate query response device 266. The automated pressurization of the blood pressure cuff employed in the patient health monitoring system may also be used as a stimulus. Query response device 266 can take the form of, for example, a toggle or rocker switch or a depressible button or other moveable member hand held or otherwise accessible to the patient so that the member can be moved or depressed by the patient upon the patient's receiving the auditory or other instruction to respond. In a preferred embodiment, the query system has multiple levels of auditory stimulation and/or vibratory or other sensory stimulation to command the patient to respond to the query. For example, an auditory stimulus would increase in loudness or urgency if a patient does not respond immediately or a vibratory stimulus may be increased in intensity.

After the query is initiated, ACQ system 256 generates signals to reflect the amount of time it took for the patient to activate response device 266 in response to query initiate device 264 (i.e., this amount of time is sometimes referred to as the "latency period"). ACQ system 256 is electronically coupled to electronic controller 14 and the signals generated by ACQ system 256 are suitably converted (e.g., employing an A-D converter) and thereby provided to controller 14. If the latency period is determined by controller 14, which employs software to compare the actual latency period with stored safety data set parameters reflecting safe and undesirable latency period parameters, to be outside of a safe range, the physician is notified, for example, by means of an alarm or other attention-commanding device. If no action is taken by the physician within a pre-set time period, controller 14 commands the decrease in level of sedation/analgesia/amnesia by control and operation on electronic flow controllers 133, 135 of FIG. 8. The values of the signals reflecting the latency period are displayed on display device 35 (or on LED devices located on housing 15 or on remote control device 45, FIG. 1) and the physician may thus increase or decrease drug delivery based on the latency period.

The patient interface system of FIG. 11 also includes a drug dosage request device 254 which allows the patient direct control of drug dosage. This is accomplished by the patient activating a switch or button to request electronic controller 14 to command the increase or decrease in the amount of drug he or she is receiving. For example, if a patient experiences increased pain he or she may activate the increase portion of the switch of device 254, whereas, if a patient begins to feel nauseous, disoriented or otherwise uncomfortable, he or she may request a decrease in drug dosage. In embodiments where drug delivery is intravenous, such delivery can be by continuous infusion or bolus. A feedback signal from device 254 representing the patient's increase or decrease in drug dosage request is electronically communicated to controller 14 which employs conservative, decision-making software, including comparison of monitored patient conditions with stored safety parameters reflecting patient physiological conditions, to effect safe, optimized drug delivery in response to patient requests. The amount of increase or decrease administered by controller 14 can be pre-set by the physician through user access devices such as keyboard 230, FIG. 2. For example, where the drug being delivered is nitrous oxide, the approved increase or decrease may be in increments of +10%. When not activated by the patient, drug request device 254 remains in a neutral position. The invention thus integrates and correlates patient-controlled drug delivery with electronic monitoring of patient physiological conditions.

In an alternative embodiment, the physician is notified via user interface system 16 (display device 30 or LEDs remote control device 45), FIG. 1 of the patient request to increase or decrease drug dosage and can approve the requested increase or decrease taking into account the patient's present vital signs and other monitored physiological conditions, including consciousness level status as obtained from-the various patient interface system monitors 252, 256 (FIG. 11).

In a preferred embodiment of the invention, the patient controlled drug dosage request system 254 has lock-out capabilities that prevent patient self-administration of drugs under certain circumstances. For example, access to self-administration will be prevented by electronic controller 14 under circumstances where patient physiology parameters or machine state parameters are or are predicted to be outside of the stored safety data set parameters. Access to self-administration of drugs could also be inhibited at certain target levels or predicted target levels of drugs or combined levels of drugs. For example, if it were predicted that the combined effect of requested drugs would be too great, drug delivery in response to patient requests would be prohibited. It is noted that such predictive effects of drugs could be determined through the use of various mathematical modeling, expert system type analysis or neural networks, among other applications. In short, the invention is designed to dynamically change drug administration and amount variables as a function of patient physiology, care system state and predictive elements of patient physiology.

Additionally, it is contemplated that patient self-administration of drugs could be prohibited at times when drug levels are changing rapidly. For example, if a patient is experiencing pain and that is apparent to the physician, the physician may increase the target level of drug while at the same time the patient requests additional drug. The subject invention will sequentially address the physician and patient requests for drug increases and will lock out any patient-requested increases that are beyond programmed parameters.

In an additional aspect of the invention, a patient may be stimulated or reminded to administer drugs based on electronic feedback from the patient physiology monitoring systems. For example, if there is an underdosing of analgesics and the patient is suffering pain evidenced by a high respiratory rate or high blood pressure reflected in electronic feedbacks to the electronic controller, the controller can prompt the patient to self-administer an increase in drugs. This could be accomplished by, for example, an audio suggestion in the patient's ear. Thus, it is contemplated that the invention will have an anticipatory function where it will anticipate the patient's needs for increased drugs.

In a preferred embodiment of the invention, one or more patient vital sign monitoring devices 252, ACQ system devices 256, and a drug dosage request device 254 are mechanically integrated in a cradle or gauntlet device 55 (FIG. 2) constructed to accommodate and otherwise fit around a patient's hand and wrist. FIG. 2 shows generally hand cradle device 55 electronically coupled by lead 50 to care system 10. One embodiment of a hand cradle device in accordance with this invention is shown in more detail in FIGS. 12A and 12B.

Figure 12A:
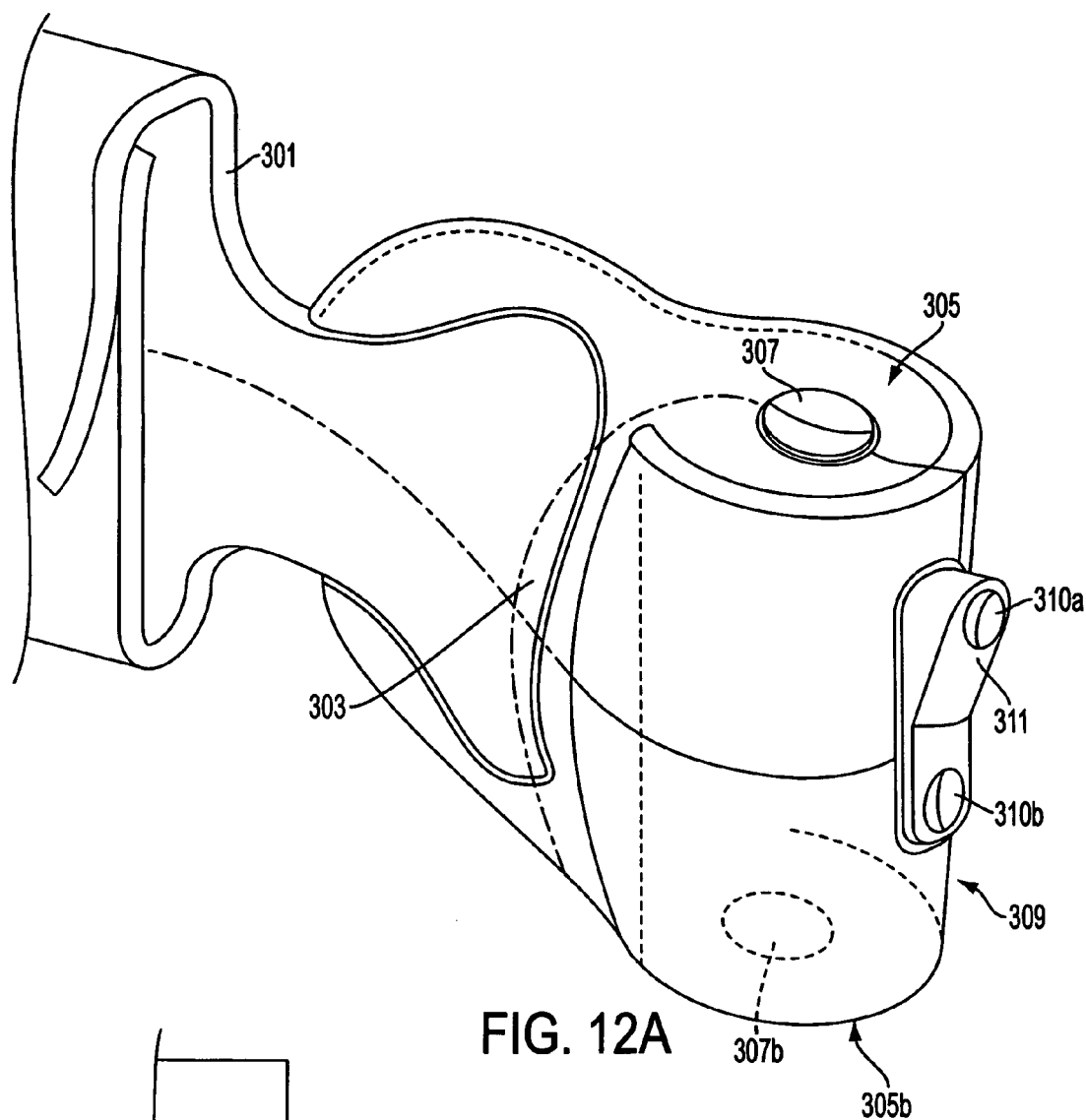
FIGS. 12A and 12B are a front perspective view and a side-elevational view, respectively, of a preferred embodiment of hand cradle device constructed in accordance with the invention.
Figure 12B:
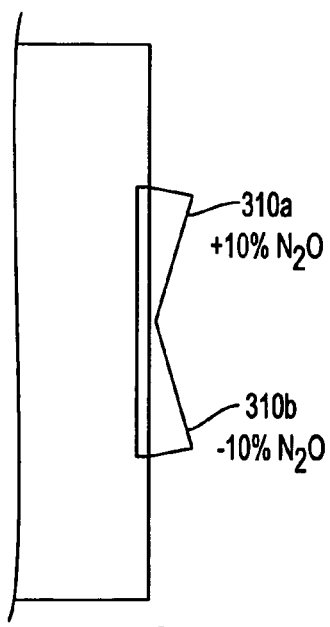

FIG. 12A shows blood pressure cuff 301 capable of being wrapped around a patient's wrist and affixed to itself such that it can be held in place. Cuff 301 is affixed to palm support portion 303. Alternatively, the cuff may be separated from palm support portion 303 and placed on the upper arm at the physician's discretion. A recessed, generally elliptical or rounded portion 305 is supported by the top edge of palm support portion 303 and is capable of receiving and supporting the bottom surface of a patient's thumb. Depressible query response switch 307 is located within thumb support portion 305 such that switch 307 is capable of being depressed by the patient's thumb. The thumb support portion 305 may be constructed so as to have a housing, frame, raised walls or other guide so that a patient's thumb may more easily be guided to depress or move buttons or switches within portion 305 (here, switch 307), or so that any significant patient thumb movement toward the switch will activate same. Supporting thumb support portion 305 and abutting palm portion 303 is finger support portion 309 for receiving in a wrapable fashion the patient's fingers. Drug dosage request switch 311 is integrated into finger support portion 309 and is in the form of a rocker switch whereby depressing the top portion 310a of said switch will effect an increase in the delivery of sedative, analgesic and/or amnestic whereas depressing the bottom portion 310b of said rocker switch will effect a decrease in drug delivery at an appropriate set percentage (e.g., ±10%, FIG. 12B). Rocker switch 311 is constructed so as to remain in a neutral position when not being actuated by the patient.

Figure 13B:
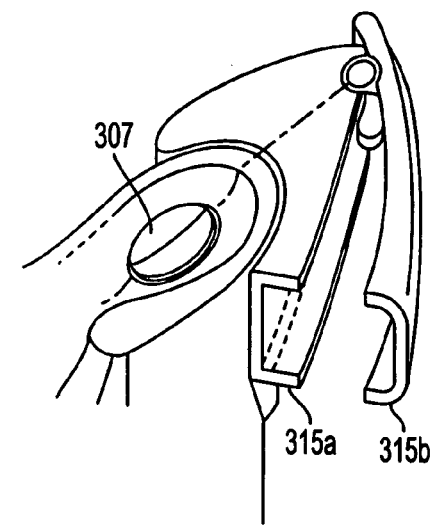
FIGS. 13A and 13B are rear perspective views of a preferred embodiment of hand cradle device constructed in accordance with the invention.
Figure 13A:
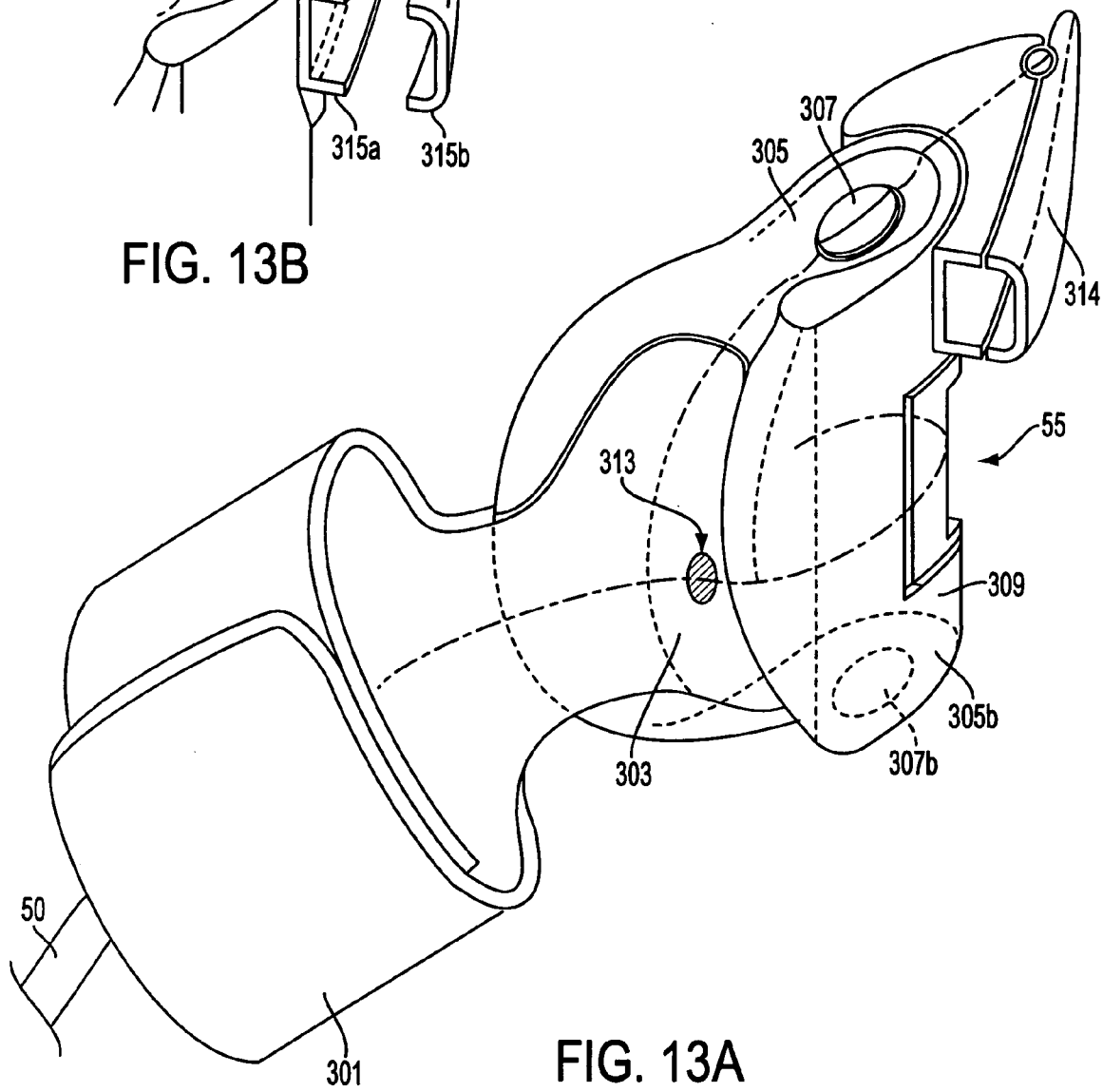

FIGS. 13A and 13B show an additional embodiment of the hand cradle device of this invention. Specifically, a pulse oximetry sensor 314 is mechanically affixed to and electronically coupled to hand cradle device 55 abutting the upper end of finger support portion 309, and being generally planar vis-a-vis the outer edge of thumb support portion 305. Pulse oximeter 314 is constructed as a clip which can be placed on a patient's finger. The transmitter and receiver portions of sensor 314 are contained in the opposite sides 315a, 315b (FIG. 13B) of the finger clip 314 such that when placed on a finger, infra-red radiation travels through the finger; through spectral analysis the percentage of oxygenated hemoglobin molecules is determined. In this embodiment of hand cradle device 55 the query initiate device 313 is in the form of a small vibrator located in palm support portion 303. Alternatively, to enhance patient attentiveness to the query initiate device and to increase patient accuracy in depressing the response switch, the vibrator may be located adjacent the query response switch 307 or, in the embodiment of FIG. 14A, adjacent response switch 407.

Figures 14A, 14B:
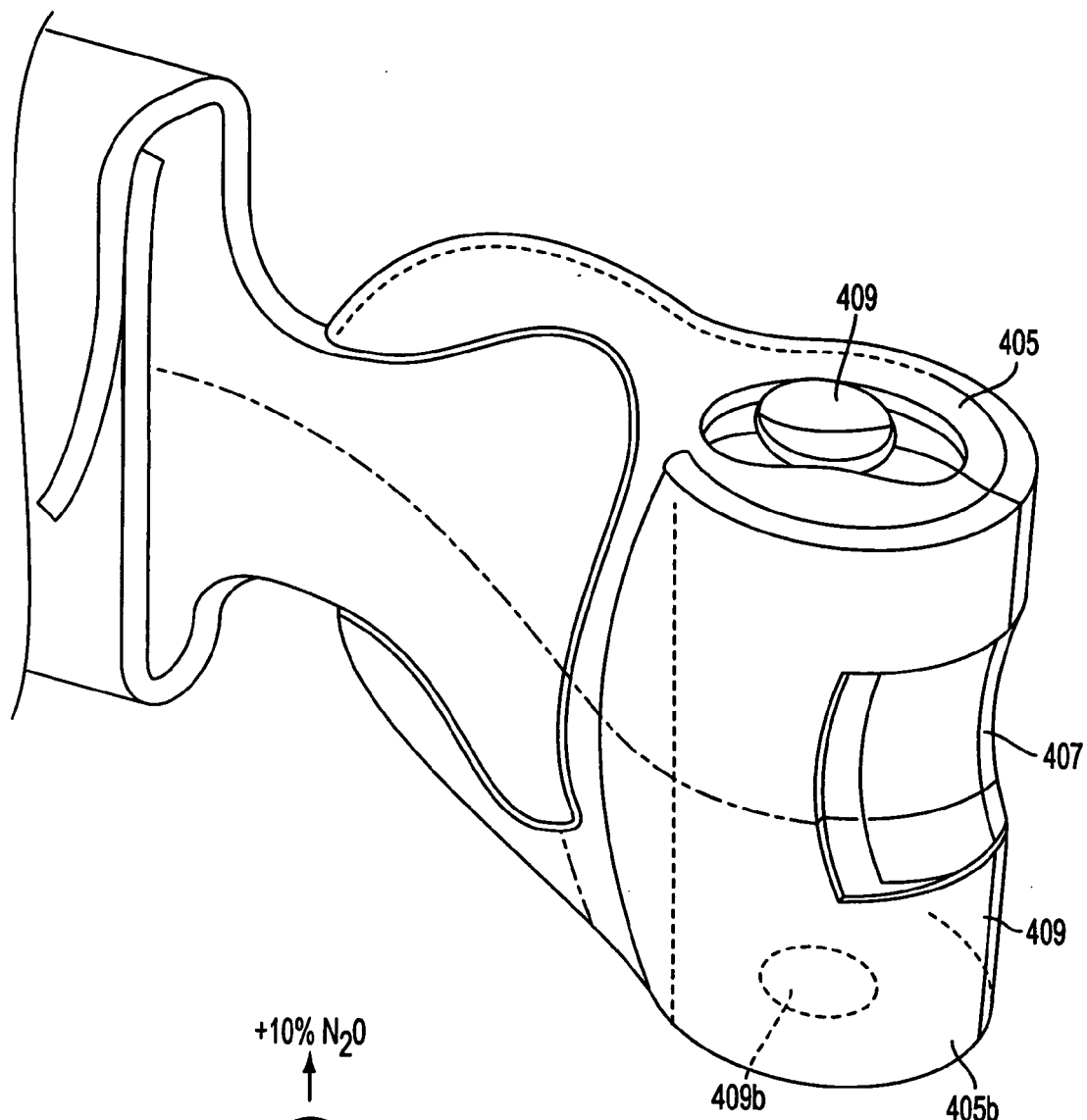
FIGS. 14A and 14B are, respectively, a front perspective view of an alternative embodiment of a hand cradle device constructed in accordance with this invention and a top plan view of a patient drug dosage request device in accordance with the invention.

In an alternative embodiment of hand cradle device 55, now referring to FIGS. 14A and 14B, drug dosage request device 409 is located within thumb portion 405 and is in the form of a slidable member 409 wherein sliding member 409 forward effects an increase in analgesic dosage and sliding portion 409 backward effects a decrease in analgesic dosage (FIG. 14B). In this embodiment of the invention, query response device 407 is a depressible portion integrated within finger support portion 409.

All embodiments of hand cradle device 55 are constructed so as to be ambidextrous in nature, namely, they accommodate and are workable by a patient's right or left hand. For example, in FIGS. 12A and 13A, a second query response switch 307b is located within a symmetrically opposed thumb portion 305b affixed to the opposite end of finger portion 309. Similarly the device of FIG. 14A is also constructed with a symmetrically opposed thumb portion 405b and drug dosage request device 409b. The pulse oximeter clip 314 is affixed to finger support portion 309 so as to be mechanically and electronically quick releasable to permit reversibility when used on the opposite hand. It should also be recognized that the pulse oximeter clip 314 may be tethered to hand cradle device 55 rather than mechanically affixed thereto, or blood pressure cuff 301 and oximeter clip 314 may be mechanically separate from cradle device 55 and electronically coupled to controller 14 with flexible leads.

Figure 15:
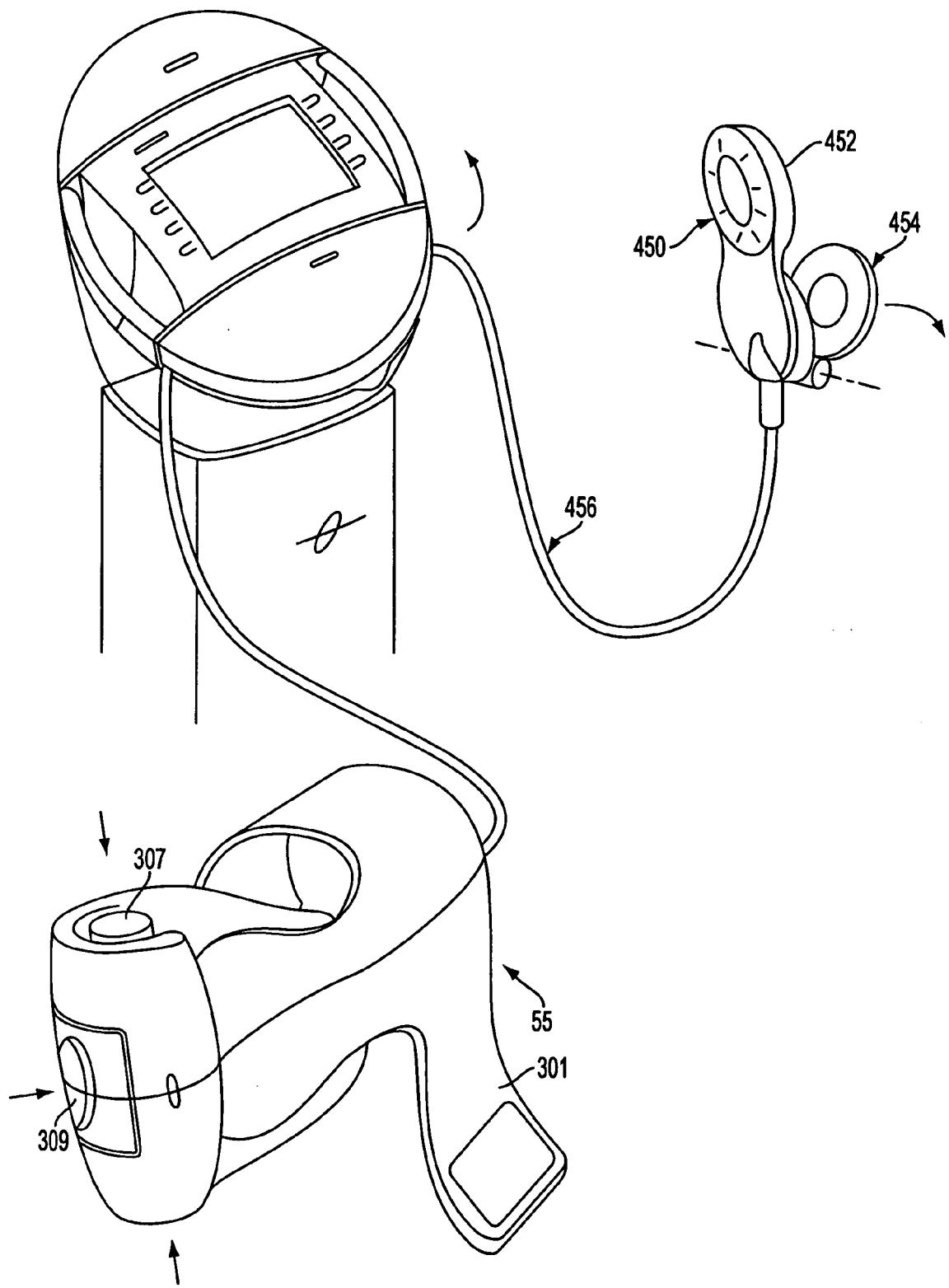
FIG. 15 shows a perspective view of a preferred embodiment of the invention, including a hand cradle device and an ear piece combination oximeter/auditory query device.
Figure 16:
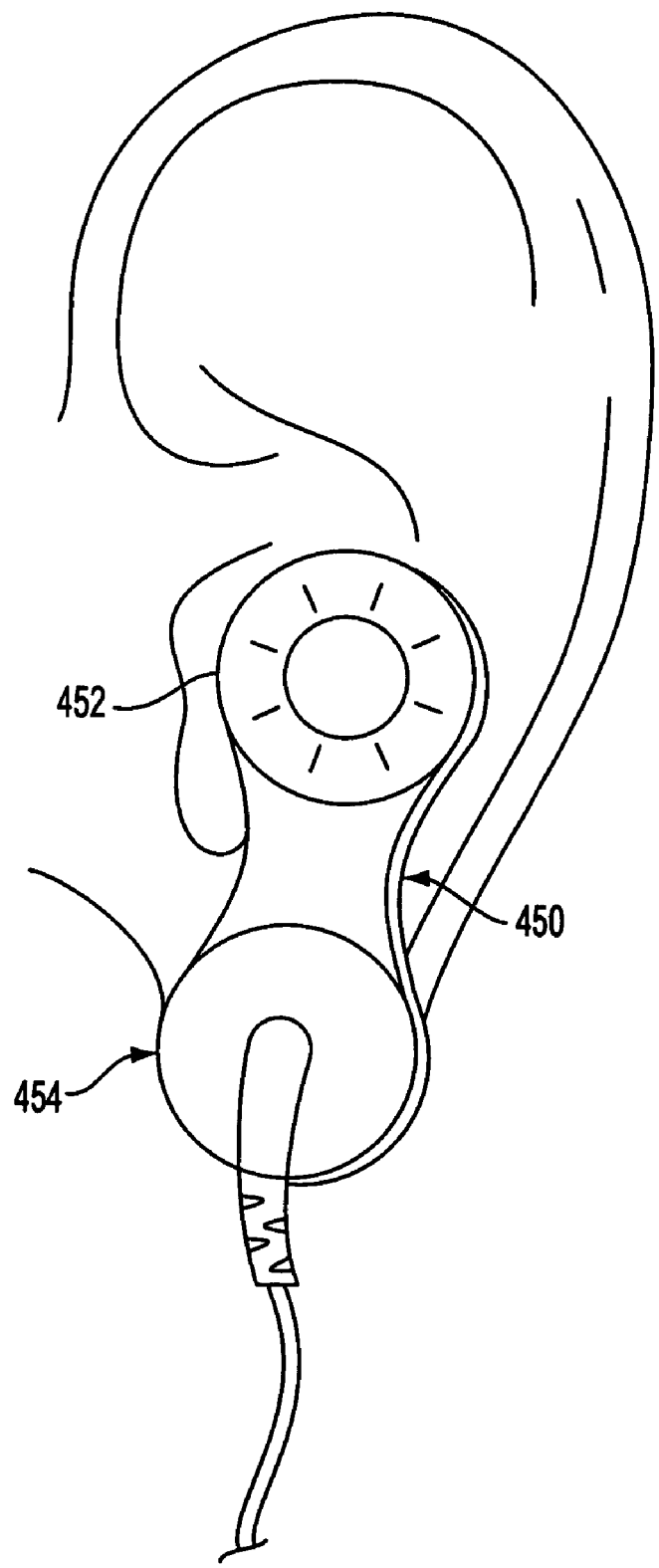
FIG. 16 is a side-elevational view of an ear piece placed within a patient's ear containing a pulse oximetry sensor and an auditory query in accordance with the present invention.

Referring to FIG. 15, an additional alternative embodiment of the invention is shown in which hand cradle device 55 includes mechanically integrated blood pressure cuff 301, query response device 307 and analgesic request device 309 similar to that described above. This embodiment, however, includes an ear clip device 450 capable of being clipped to the lobe of a patient's ear and being electronically coupled to electronic controller 14 via lead 456. Referring additionally to FIG. 16, ear clip 450 comprises a query initiate device 452 in the form of a speaker which provides an audible command to patient to activate the response switch. Such speaker may also command a patient to self-administer drugs or play music to a patient during a procedure. Pulse oximeter 454 is a clip capable of being affixed to a patient's ear lobe. One side of the clip being a transmitter and the other side of the clip being a receiver to effect the infra-red spectral analysis of the level of oxygen saturation in the patient's blood.

In an additional aspect of the invention, it is contemplated that the care system's automated monitoring of one patient health conditions is synchronized with the monitoring of one or more other patient health conditions. For example, in a preferred embodiment, if the controller 14, receives low $O_2$ saturation, low heart rate or a low perfusion index feedback information from the pulse oximeter (e.g., the actual parameter received is in the undesirable range of the stored safety data set for those parameters), such feedback will trigger controller 14 to automatically inflate the blood pressure cuff and check the patient's blood pressure. (This is because low $O_2$ saturation can be caused by low blood pressure; and low heart rate can cause low blood pressure and vice versa, etc.) Therefore, under normal operating conditions the preferred embodiment of the invention will automatically check the patient blood pressure every 3 to 5 minutes, and whenever there is a change in other patient parameters such as blood $O_2$ saturation or heart rate. In another example, the electronic checking of blood pressure is synchronized with the automated consciousness query because the activation of the cuff may arouse a patient and affect query response times. Thus the invention contemplates an "orthogonal redundancy" among patient health monitors to ensure maximum safety and effectiveness.

As described above, one aspect of a preferred embodiment of the invention includes the electronic management of drug delivery via software/logic controlled electronic controller 14 to integrate and correlate drug delivery with electronic feedback signals from system monitors, one or more patient monitor/interface devices and/or user interface devices. Specifically, electronic signal values are obtained from care system state monitors; from patient monitor/interface devices (which can include one or more vital sign or other patient health monitors 252, ACQ system 256, and/or patient drug dosage request device 254, FIG. 11); and in some instances from one or more user interface devices. All are electronically coupled to, through standard A-D converters where appropriate, electronic controller 14. The controller 14 receives the feedback signal values and, via software and programmed logic, effects a comparison of these values representing the patient's monitored physiological conditions with known stored data parameters representing safe and undesirable patient physiological conditions (a safety data set). Controller 14 then generates an instruction in response thereto to maintain or decrease the level of sedation, analgesia, and/or amnesia being provided to the conscious patient thereby managing and correlating drug delivery to safe, cost-effective and optimized values (FIG. 2B. Controller 14 is operatively, electronically coupled to electronic flow controllers 133, 135 (FIG. 8) of electronic mixer 44 which (via solenoid valves) adjust flow of gaseous drug and $O_2$ in a closed-loop fashion as described above. In intravenous embodiments such flow controllers would adjust the flow of one or more combination of IV drugs. It should be recognized that the electronic values provided to microprocessor controller 14 to effect management and correlation of drug delivery, could include one or more signals representing patient vital signs and other health conditions such as pulse oximetry, without necessarily including signal(s) representing level of patient consciousness, and vice versa.

As also indicated above, the software effecting electronic management of drug delivery by controller 14 employs "conservative decision-making" or "negative feedback" principles. This means, for example, that the electronic management of drug delivery essentially only effects an overall maintenance or decrease in drug delivery (and does not increase drugs to achieve overall increased sedation/analgesia). For example, if ACQ system 256 (FIG. 11) indicates a latency period outside of an acceptable range, controller 14 may instruct electronic flow controller 133 (FIG. 8) to increase the flow of oxygen and/or instruct flow controller 135 to decrease the flow of gaseous drug to manifold system 48.

In another example of such electronic management of drug delivery by conservative decision-making principles, if ACQ system 256 (FIG. 11) indicates a latency period in response to a patient query given every 3 minutes outside of an acceptable range, electronic controller 14 may immediately cease drug delivery, but at the same time, increase the frequency of times that the patient is queried, e.g., to every 15 seconds. When the patient does respond to the query, the drug delivery is reinitiated, but at a lower overall dose such as 20% less than the original concentration of drug that had been provided.

A further example of the invention's electronic management of drug delivery through conservative, decision-making software instruction employs known target-controlled infusion software routines to calculate an appropriate dosage of IV drug based on patient physical parameters such as age, gender, body weight, height, etc. Here, a practitioner provides the patient physiological parameters through the user interface system, the electronic controller 14 calculates the appropriate drug dosage based on those parameters, and drug delivery begins, for example, as a bolus and is then brought to the pre-calculated target level of infusion. If later there is a significant change in a patient monitored parameter, e.g., pulse oximetry or latency period falls outside of a desired range, controller 14 effects a decrease in overall drug delivery as described above.

One concern that the invention addresses with respect to the target controlled infusion of IV drugs is the nature and speed at which the care system reaches the steady state target level of drug. For example, an important consideration for the physician is, once drug administration begins, when is the patient sufficiently medicated (e.g., sedated or anesthetized), so that the physician can begin the procedure. It is frequently desirable that the patient reach the steady state target level of drug as rapidly as possible so that the procedure can begin as soon as possible. It has been determined that one way of reaching a suitable level of drug effectiveness quickly is to initially overshoot the ultimate steady state target drug level. This shortens the time between the beginning of drug delivery and the onset of clinical drug effectiveness so that the procedure may begin. Typically, predicted target levels have an error of plus or minus 20%, therefore, one approach of reaching the clinical effectiveness state quickly is to attempt to reach at least 80% of the ultimate target level, but initially overshoot that 80% level by giving a 15% additional increase of drug infusion beyond the 80% target. One method of accomplishing this is to use currently available PDI controllers which employ an error state (here the difference between predicted drug levels in the blood stream and the target level) to arrive at an infusion rate. Other control systems, however, that allow some initial overshoot of the target blood level of the drug to get to a clinical effectiveness level quicker would also be appropriate.

Figure 17:
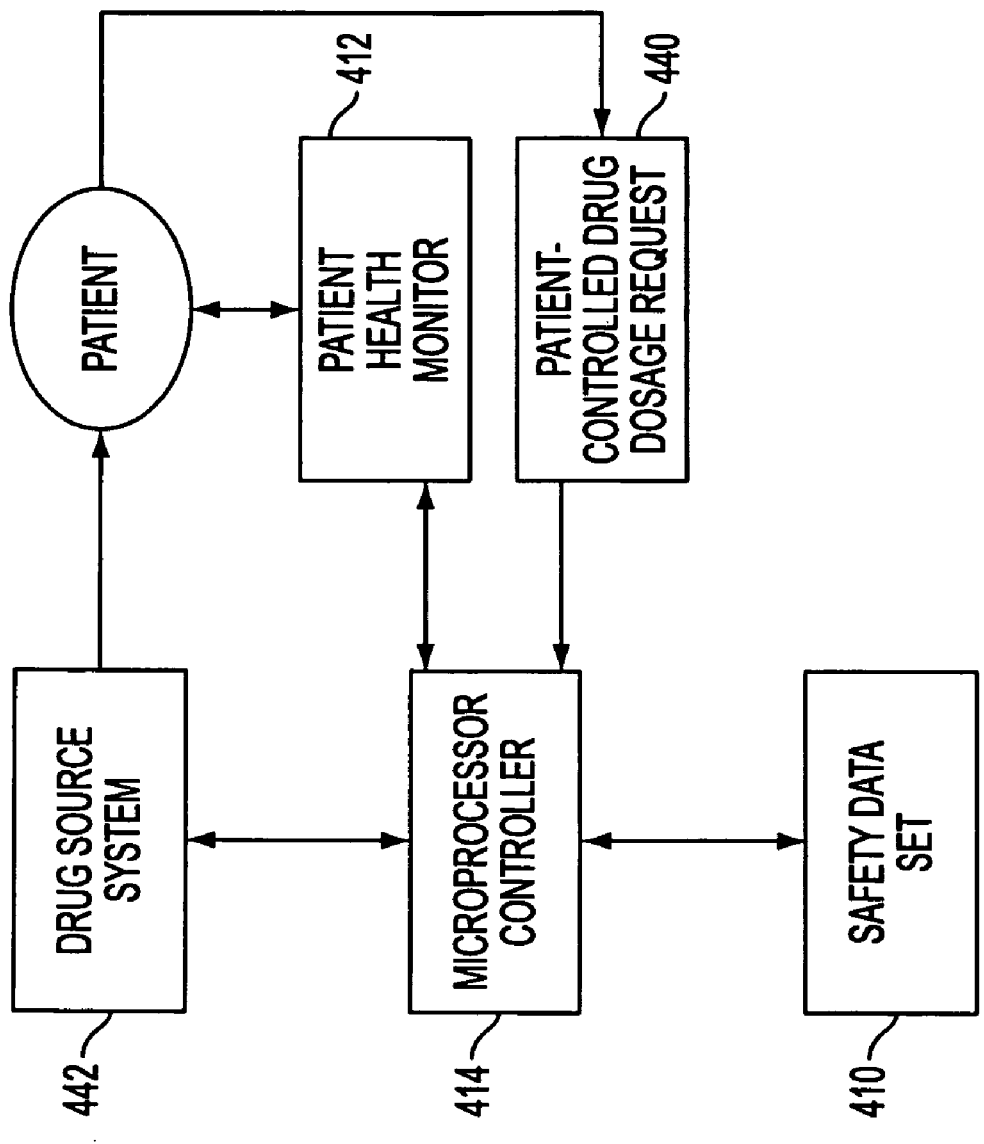
FIG. 17 depicts an alternative preferred embodiment of a care system apparatus constructed in accordance with the invention.

FIG. 17 is a schematic of an alternative embodiment of an apparatus constructed in accordance with the invention which is particularly suitable for remote medical care locations and home care-type settings for indications such as post-operative or other post-procedural pain and/or discomfort, including, for example, nausea secondary to oncology chemotherapy. In this embodiment, drug source system 442 delivers drugs to the patient (which may be drugs such as propofol, morphine, remifentanil and others) intravenously by, for example, use of a known syringe pump-type device capable of being worn or otherwise affixed to the patient, or delivers such drugs transdermally by, for example, use of known ion transfer-type devices, among others. The drug delivery may be continuous or by drug bolus and without an integrated supply of $O_2$. If necessary, oxygen may be supplied to the patient from separate tanks or an in-house, on-site oxygen source. The resulting apparatus is simplified—there is no requirement for an integrated $O_2$ source, electronic mixer, manifold, or the airway circuit and face mask devices described above.

One or more patient health monitors 412 such as known pulse oximeters, blood pressure cuffs, $CO_2$ end tidal monitors, EKG, and/or consciousness monitors, or other monitors such as those indicated herein, monitor the patient's physiological condition. Drug dosage may be pre-set by a physician prior to or during application of drug delivery and/or also patient controlled thereafter by means of a patient drug dosage increase or decrease request devices generally of the type of that described above. It should also be understood that the intravenous delivery of drugs may be by continuous infusion, target-controlled infusion, pure bolus, patient-elected bolus or combinations thereof.

Still referring to FIG. 17, electronic management of drug delivery in this embodiment of the invention is provided by electronic controller 414 which may be of a type described above. Controller 414 employs conservative decision-making software and/or logic devices to integrate and correlate drug delivery by drug source system 442 (which may include known solenoid type or other electronic flow controllers) with electronic feedback values from one or more patient health monitors 412. The values (signals) from patient health monitors 412 represent one or more actual patient monitored physiological conditions. Controller 414, through software employing comparison protocols such as those described herein, accesses stored safety data set 410 which contains data reflecting safe and undesirable patient physiological conditions, and compares the signals reflecting actual patient monitored conditions with same. As described above, safety data set 410 may be stored in a memory device such as an EPROM. Based on the result of the comparison, controller 414 either instructs no change in drug delivery or generates a signal instructing the drug flow controllers of drug source system 442 to manage application of the drug to safe, optimized levels.

In certain aspects of the invention, controller 414 may also access, through software, pre-set parameters stored in a memory device representing initial or target drug dosages and lock-outs of patient drug administration requests as described above. In these circumstances, instruction signals generated by controller 414 would also account for and control drug delivery in accord with these pre-set parameters.

This embodiment of the invention would also typically include system state monitors, such as electronic sensors which indicate whether power is being supplied to the system or which measure the flow of drugs being delivered. Such system state monitors are electronically coupled to controller 414 and provide feedback signals to same—the control of drug delivery by controller 414 electronically coupled to drug source system 442 in response to said feedback signals is similar to that as described herein with respect to other embodiments.

In another aspect of the invention, electronic controller 414 is located on a remote computer system and electronically manages on-site drug delivery integrating and correlating same with on-site monitoring of patient physiological conditions and care system states as described above, but here with instructions signals generated from a remote location. It is contemplated that controller 414 may, in some embodiments, effect transmission via modem or electronic pager or cellular-type or other wired or wireless technologies of electronic alarm alerts to remote locations if a monitored patient parameter such as the percentage of oxygen absorbed into the blood ($S_pO_2$) falls outside of a safe established value or range of values as established by the stored safety data set. Such remote locations could thereby summon an ambulance or other trained caregiver to respond to the alarm alert.

Figure 18:
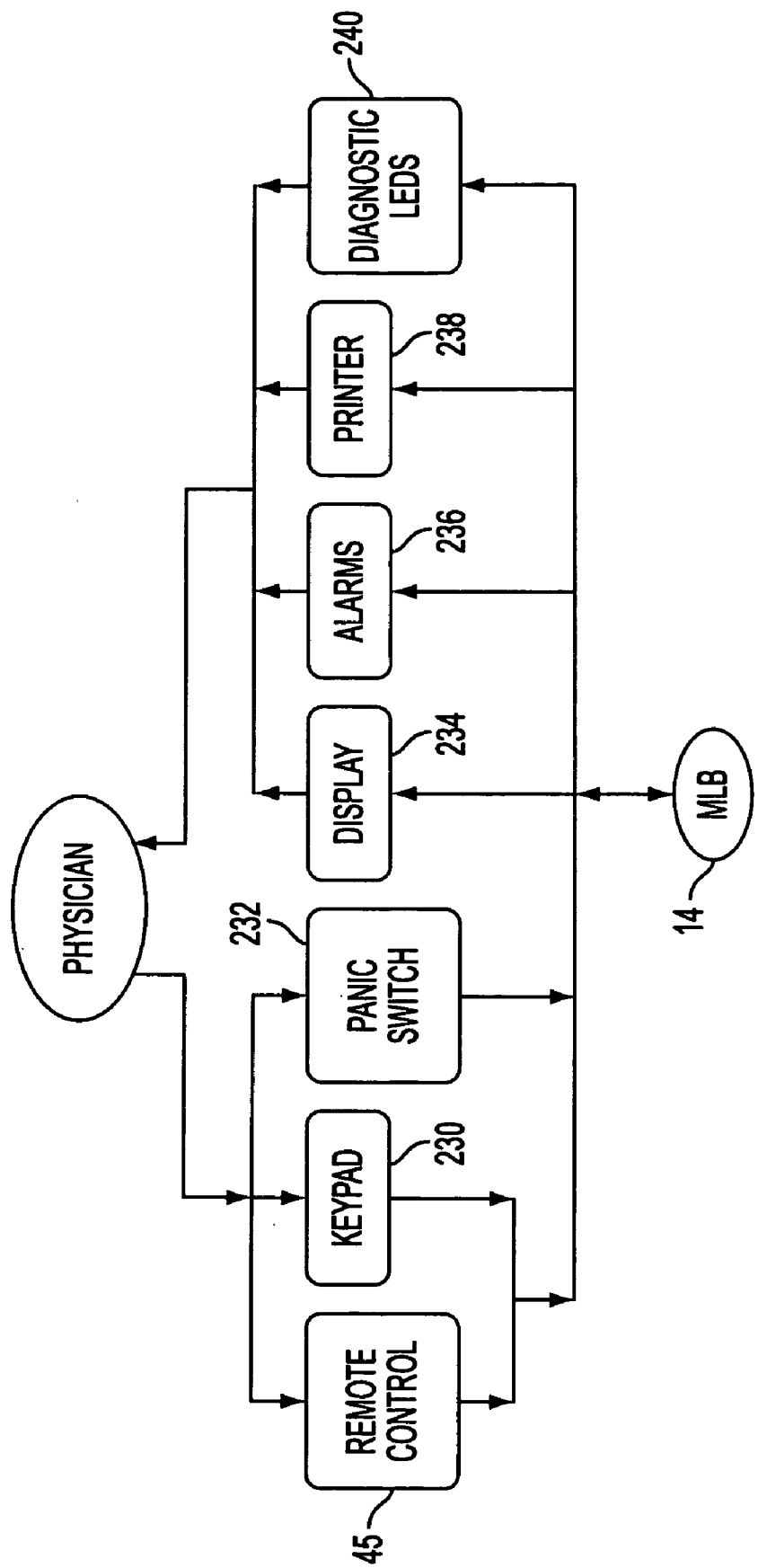
FIG. 18 depicts a user interface system in accordance with a preferred embodiment of the invention.

FIG. 18 details the user interface system of a preferred embodiment of the invention. This system enables the physician to safely and efficaciously deliver one or more of sedation, analgesia or amnesia to a patient while concurrently performing multiple tasks. The user interface permits the physician to interact with the care system and informs the user of the patient's and system's status in passive display devices and a variety of active audio/visual alarms thereby enhancing the safety and enabling immediate response time (including the "conservative" responses, e.g., detailed drug delivery discussed above) to abnormal situations.

Specifically, a keypad and/or touch screen 230 (FIGS. 2 and 18) allows the physician to interact with electronic controller 14, inputting patient background and setting drug delivery and oxygen levels. A remote control device 45 (FIGS. 1 and 18) provides the physician with remote interaction with the care system 10 allowing him or her to remotely control the functions of the system. Remote control device 45 may be removably integrated into the top surface of housing 15 and capable of being clipped onto material close to the physician and/or patient. In one aspect of the invention, the remote control device 45 itself contains display devices such as LEDs to advise the physician of patient and system parameters. A panic switch 232 (FIG. 18), which may be on-board housing 15 (FIG. 1) or contained in remote control device 45 and electronically coupled to controller 14 allows the physician to shut down care system 10 and maintains it in a safe state pre-programmed into controller 14.

Visual display devices 234 (FIG. 2, 35) display actual and predictive or target patient and system parameters and the overall operation status of the care system.

Figure 22A:
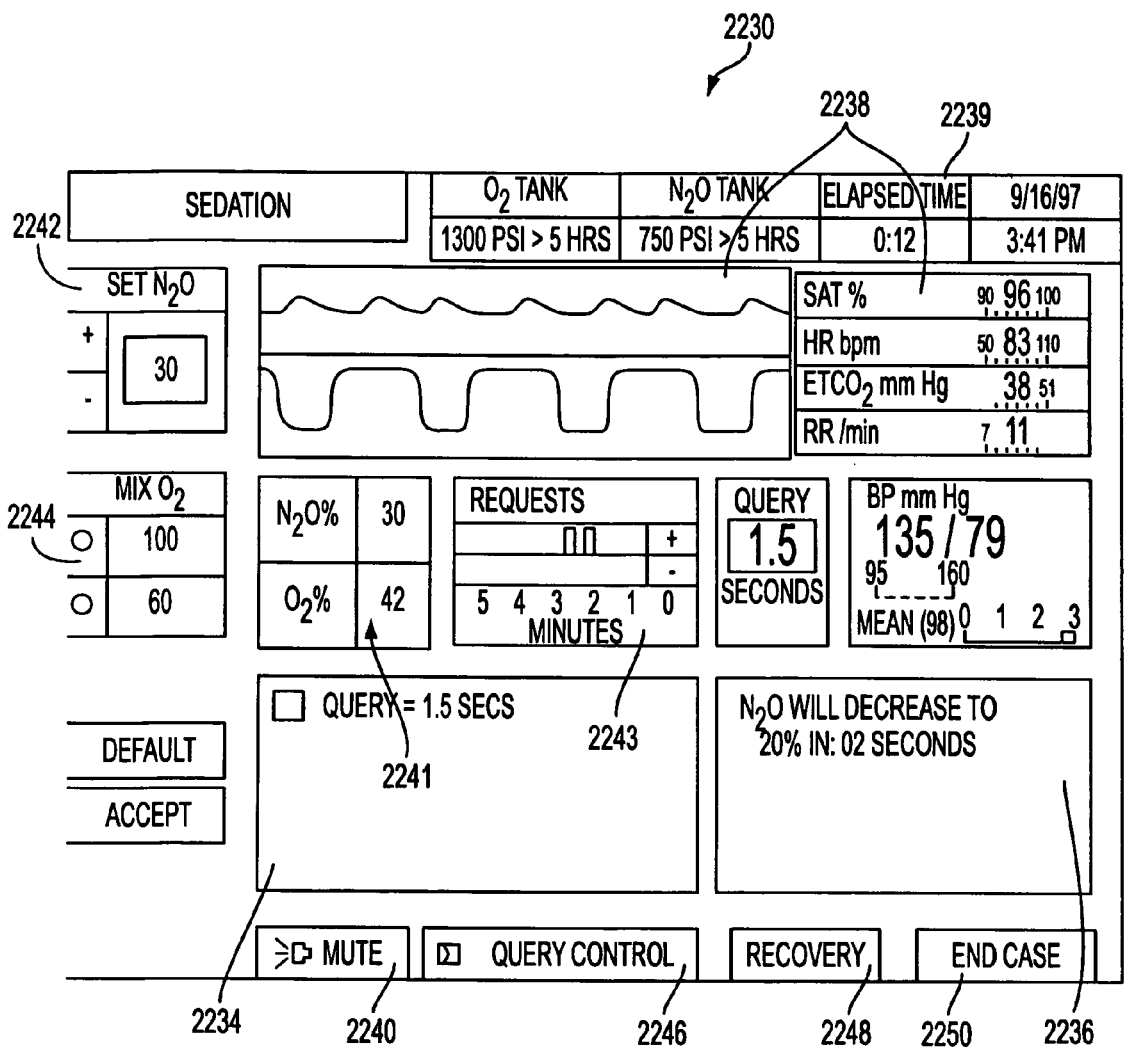
FIG. 22A depicts a first embodiment of a user interface screen display in accordance with the invention.
Figure 22B:
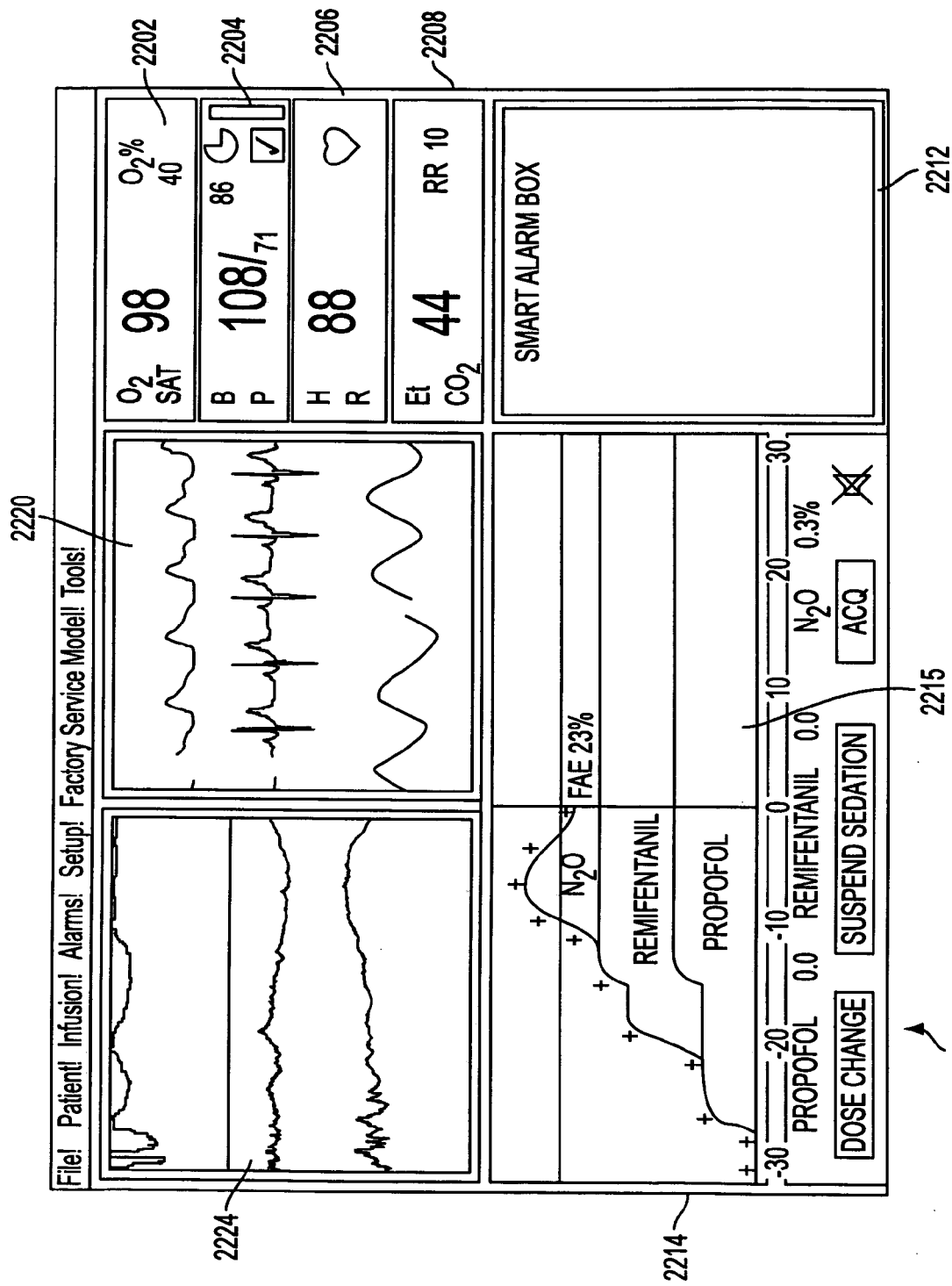
FIG. 22B depicts a second embodiment of a user interface screen display in accordance with the invention.

One version of a preferred embodiment of visual display 234 is shown in FIG. 22. The display 2230 includes a first portion of the display 2234 which is devoted to displaying to the user the current status of the system operation and monitored patient conditions, including the status of any alarm caused by a change in monitored system or patient condition. For example, if a patient's timed response to a consciousness query (latency period) is outside an established range and an alarm is thus activated, that query latency period is displayed in this first portion 2234 of the visual display, thereby enabling the physician to immediately understand the cause of the alarm.

The visual display device 2230 of this embodiment also includes a second portion of the display 2236 which is devoted to displaying the actions taken or soon to be taken by the care system. For example, if in response to an alarm indicating a latency period outside of an established safe range the apparatus will decrease the flow of drug to the patient, this second portion 2236 displays the percentage decrease in drug dosage to be effected.

Visual display 2230 facilitates the physician's interaction with the apparatus by walking the physician through various system operation software subprograms. Such subprograms may include system start-up where a variety of system self-checks are run to ensure that the system is fully functional; and a patient set-up. To begin the procedure, the care system monitors are placed on the patient and the physician activates the system by turning it on and entering a user ID (it is contemplated that such user ID would only be issued to physicians who are trained and credentialed). Next, the visual display would prompt the physician to begin a pre-op assessment, including inputting patient ID information and taking a patient history and/or physical. In the pre-op assessment, the physician poses to the patient a series of questions aimed at determining appropriate drug dosage amounts (such as age, weight, height and gender), including factors indicative of illness or high sensitivity to drugs. The responses to such questions would be inputted into the care system and employed by the system to assist the physician in selecting the appropriate dose amount. For example, the care system may make available to the physician one range of dosage units for a healthy person and a narrower range of dosage units for a sick or older person. The physician would have to make an explicit decision to go above the recommended range.

In addition to the pre-op assessment performed by the physician described above, it is also contemplated that the care system is capable of performing an automated pre-op assessment of the patient's physiology. For example, with the monitors in place, the care system will assess such parameters as the oxygenation function of the patient's lungs and/or the ventilatory function of the patient's lungs. The oxygenation function could be determined, for example, by considering the A-a gradient, namely, the alveolar or lung level of oxygen compared to the arteriolar or blood level of oxygen. The ventilatory function of the lungs could be determined from pulmonary function tests (PFTs), among other things, which are measurements of the amount of air and the pressure at which that air is moved in and out of the lungs with each breath or on a minute basis. (It is contemplated that these assessments are performed before the procedure begins and during the procedure as a dynamic intra-operative assessment as well.) Also during the pre-op (or as a continuous intra-operative) assessment, heart function may be assessed by viewing the output of an EKG to determine whether there is evidence of ischemia or arrhythmias. Alternatively, automated algorhythms could be applied to the EKG signals to diagnose ischemia or arrhythmias. Additional automated patient health assessments could also be made.

During patient set-up, current patient and system parameters may also be assessed and displayed, and the consciousness-query system and patient drug increase/decrease system tested and baselined. A set drug subprogram allow for the selection of drugs and/or mixture of drugs (or drug, oxygen and air), allows for picking target levels of drugs, and/or permits enabling of the patient's self-administration of drugs within certain ranges. The invention also contemplates during the pre-op assessment determining a sedation threshold limit for the given patient in the unstimulated state. This could be done as a manual check, i.e., by simply turning up the drug levels and watching the patient manually or the procedure could be automated where the drugs are increased and the safety set parameters such as those for latency (consciousness queries) are tested as the concentration at the drug effect site is increased.

The system and patient status and system action may be displayed during, for example, a sedation subprogram. Visual display device 2230 may include graphical and numeric representations of patient monitored conditions such as patient respiratory and ventilatory status, consciousness, blood $O_2$ saturation, heart rate and blood pressure (2238); an indication of elapsed time from the start of drug delivery (2239); drug and/or $O_2$ concentrations (2241); and indications of patient requests for increases or decreases in drug (2243). The actual fraction of inspired oxygen calculated may also be displayed. Command "buttons" are included to mute alarms (2240), change concentration of drug delivered (2242), turn on or off the mixing of an oxygen stream with atmospheric air (2244), and to turn on or off or make other changes to the automated consciousness query system (2246). Command buttons may also be included to place the apparatus in a "recovery" mode once the procedure is completed (patient parameters are monitored, but drug delivery is disabled) (2248), and to end the case and start a new case (2250) or shut-down the system.

An alternate version of a preferred embodiment of the visual display portion of the invention is shown in FIG. 22A. Portions 2202, 2204, 2206 and 2208 of display device 2200 show current patient $O_2$ saturation, blood pressure, heart rate, and end tidal $CO_2$ levels, respectively. These portions displaying patient physiological state are uniquely color coded. Smart alarm box portion 2212 which may be coded in an attention getting color such as red, displays to the physician the particular alarm that has sounded. For example, if the patient $O_2$ blood saturation level falls below safe levels, the $O_2$ saturation alarm will sound and the $O_2$ saturation level will appear in smart alarm box portion 2212 where it can be easily seen by the physician. In short, whatever parameter has alarmed is moved to the smart alarm box portion; the specific alarm indicator is moved to the same place every time an alarm sounds. Also, the level of criticality of the alarm which, as described below, in a preferred embodiment may be indicated by either yellow or red color, is displayed in the patient physiological parameter portion of the display. For example, if a red level $O_2$ saturation alarm sounds, the background portion of the $O_2$ saturation portion 2202 will appear in red.

Portion 2214 of display 2200 shows the past, present and predicted levels (2215) of drug administration (the drug levels shown in FIG. 22A are the levels of nitrous oxide remifentanil and propofol). In a preferred embodiment target controlled infusion past, present and predicted levels are shown graphically beginning with the past thirty minutes and going thirty minutes into the future. The invention also contemplates bracketing a range of accuracy of target controlled infusion levels (not shown).

Display portions 2220 and 2224 depict graphical representations of patient health parameters such as the A-a gradient (oxygenation function) for the lungs, the results of pulmonary function tests, electrocardiogram, blood $O_2$ saturation, among others.

In another aspect of the invention, visual display 35 (FIG. 1) may be removably integrated into the top surface of housing 15 and capable of being removed from housing 15 and affixed to a frame near the patient, such as a gurney rail or examination table. Alternatively, or in addition thereto, a heads-up type visual display device is provided to facilitate a nonanesthetist's involvement in the medical or surgical procedure while simultaneously being able to view the status of system and patient monitored values and the details of alarm states. In this case, the display device is miniaturized and mounted onto a wearable headset or eyeglass-type mount or mounted on an easily viewed wall display.

Referring again to FIG. 18, in a preferred embodiment, audible alarms 236 alert the physician when patient or system parameters are outside of the normal range. In preferred embodiments, the alarms may be two or three stages with different tones to indicate different levels of concern or criticality. As is described above, when an alarm sounds, the user is able to immediately view the cause of the alarm because the smart alarm box portion 2212 of the visual display 2200 shows the value of the monitored system or patient parameter that caused the alarm to activate.

Figure 23A:
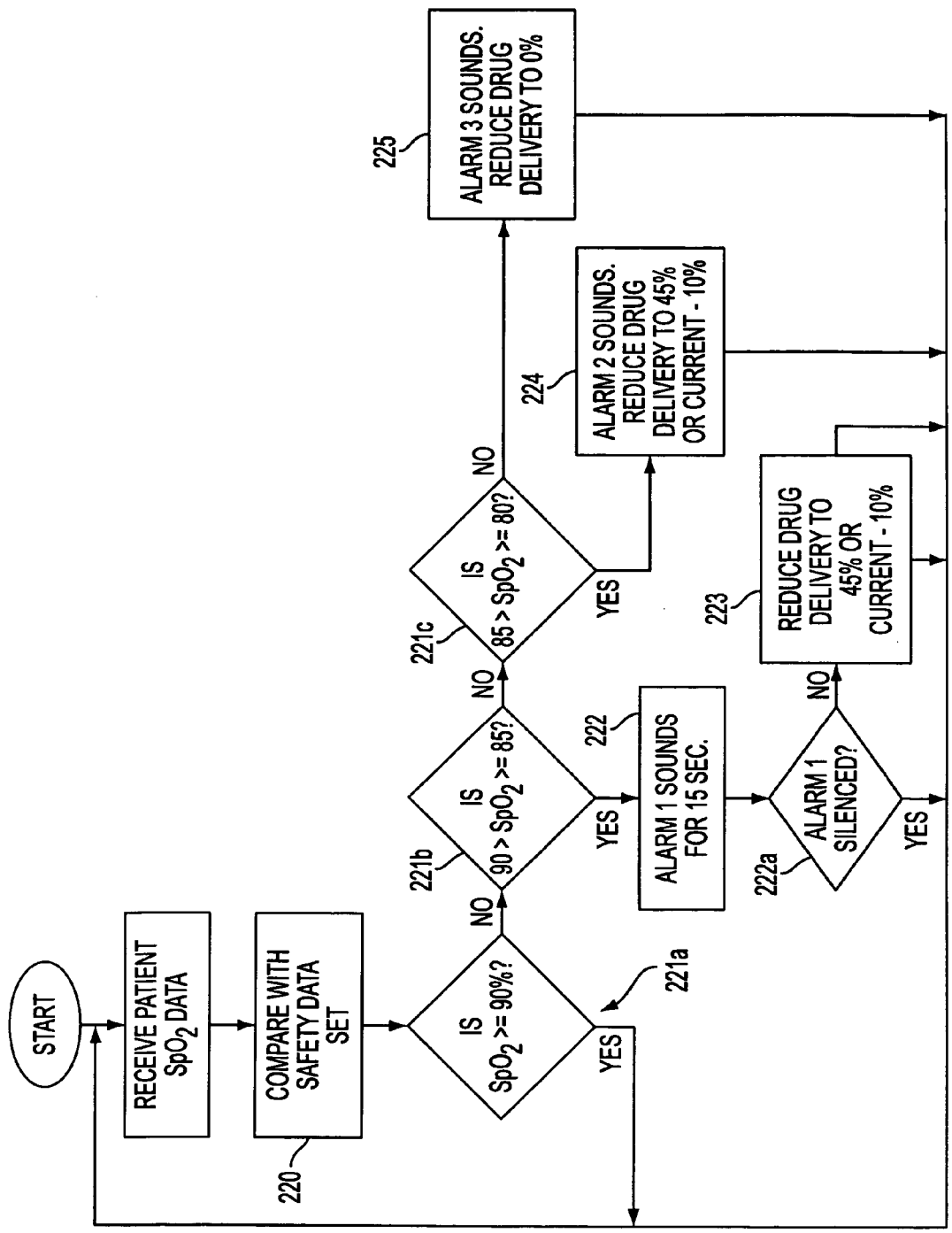
FIG. 23A is a data-flow diagram depicting an example of the steps performed by the drug delivery management software or logic responsive to patient health monitors in accordance with the invention.
Figure 23B:
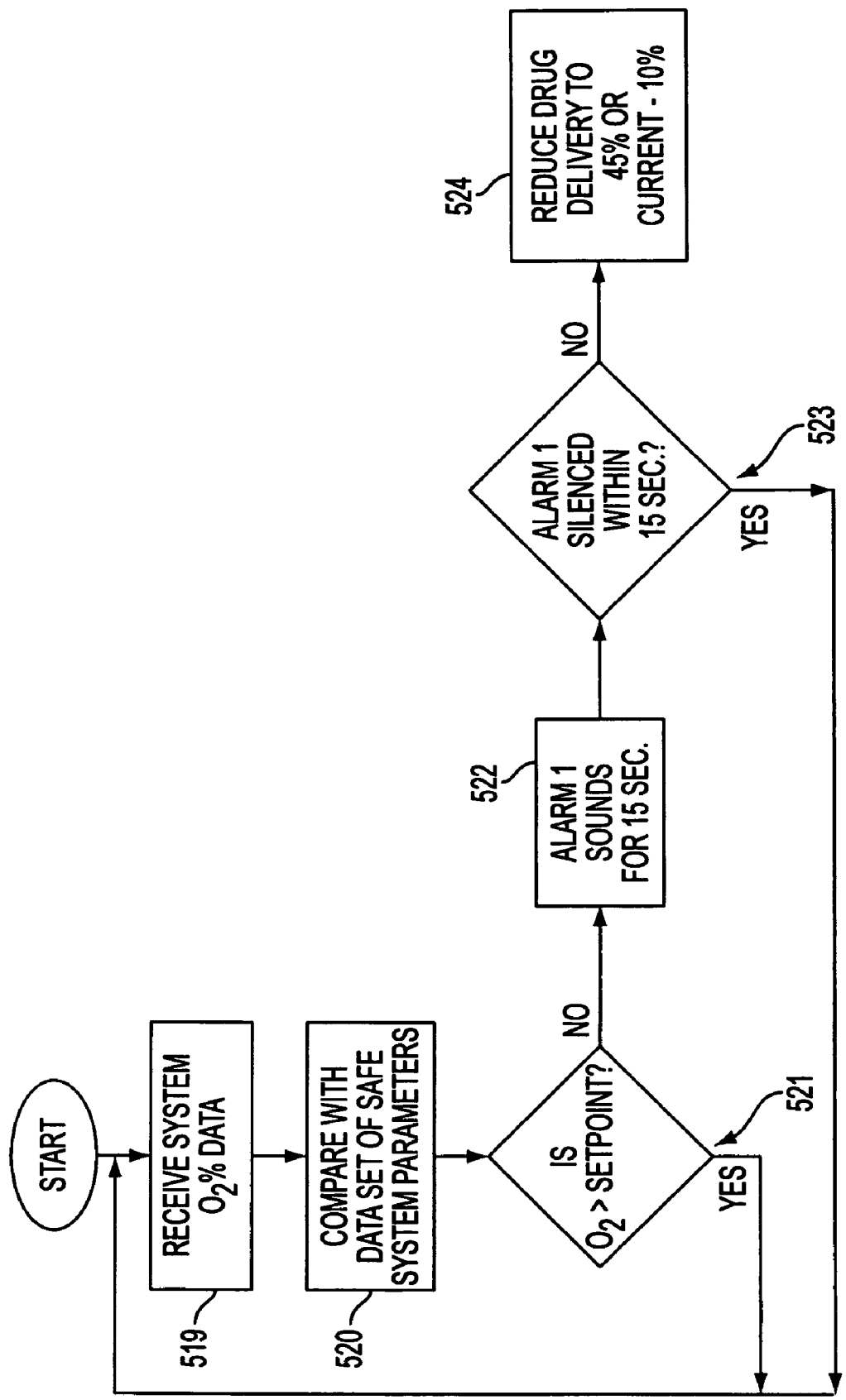
FIG. 23B is a data-flow diagram depicting an example of the steps performed by the drug delivery management software or logic responsive to system state monitors in accordance with the invention.

FIG. 21 shows examples of drug delivery management protocols for three-stage alarms responsive to patient monitors, namely, alarms "1," "2" and "3," in accordance with a preferred embodiment of one aspect of the invention. These alarms may have different tones or other indicators to denote different levels of concern or criticality. The dataflow diagram of FIG. 23 depicts one example of the steps performed by the drug delivery managing software or logic for one such protocol, namely, one where electronic controller 14 described above receives an electronic feedback signal from a pulse oximeter monitoring the actual amount of oxygen saturation in a patient's blood (the value indicated by "SpO$_2$"). As is shown, the SpO$_2$ value is compared with stored safety data set 220 containing a parameter value or range of parameters values reflecting safe and undesirable patient blood oxygen saturation conditions. If the SpO$_2$ value is greater than or equal to stored parameter 90%, no alarm sounds and no adjustment to drug delivery is effected (221*a*). If the SpO$_2$ value is less than 90%, but greater than 85% (221*b*), alarm 1 sounds for 15 seconds (222). If alarm 1 is silenced manually (222*a*), no further action is taken by the system. If alarm 1 is not silenced, the amount of drug being delivered (in this example gaseous N$_2$O) is reduced to the lesser of a concentration of 45% or the current concentration minus 10% (223). The software/logic procedure would operate in a similar fashion for intravenous and nebulized forms of drugs and the instructions provided (e.g., as in 223) would be specified for safe dosages of such drugs.

Further, if the value of oxygen saturation (SpO$_2$) is less than 85%, but greater than or equal to 80% (221*c*), alarm 2 sounds and the amount of N$_2$O being delivered is immediately reduced to the lesser of a concentration of 45% or the current concentration minus 10% (224). If the feedback value SpO$_2$ from the pulse oximeter indicates that the oxygen saturation in the blood is less than 80%, alarm 3 sounds and the amount of N$_2$O being delivered would be immediately reduced to 0% (225).

Similar protocols are described in FIG. 21 for electronic feedback signals from patient health monitors indicating pulse rate, amount of carbon dioxide in a patient's end tidal exhalations, respiration rate, systolic blood pressure, and feedback from the automated consciousness monitoring system constructed in accordance with the invention. These protocols are effected with software (and/or logic) operating in similar fashion to that described in the dataflow diagram of FIG. 23. That is, the protocol shown in FIG. 23 is one example employing one patient monitored parameter, but the operation of the invention would be similar to effect the remaining protocols of FIG. 21.

It should be understood that the system responses to alarms (described above in terms of decreases or cessation of drug concentration) could also include institution and/or increases in administration of oxygen in accord with patient and system state parameters as described above. In circumstances where drugs are halted and pure oxygen (or an O$_2$ atmospheric mix) is provided, e.g., where feedback signals indicate the patient has a low blood O$_2$ saturation, a preferred system is designed to operate in a LIFO ("last-in-first-out") manner. This means that when controller 14 receives feedback signaling an adverse patient or machine state and instructs flow controllers to turn on the oxygen, the very next breath the patient takes will be of pure O$_2$ (and/or atmospheric air) rather than of a drug/air mixture. This may be accomplished, for example, by supplying O$_2$ for air directly to PIV 152 (FIG. 9A) and bypassing reservoir bag 149.

FIG. 21A shows examples of drug delivery management protocols for two-stage alarms responsive to system state monitors, namely, alarms "1" and "2," in accordance with a preferred embodiment of one aspect of the invention. The alarms may have different tones or other indicators to note different levels of concern or criticality. The dataflow diagram of FIG. 23A depicts one example of the steps performed by the drug delivery managing software and/or logic for one such protocol, namely, one where electronic controller 14 (e.g., FIG. 2A) receives an electronic feedback value from an O$_2$ tank pressure sensor (519) indirectly measuring the amount of oxygen remaining in an on-board oxygen tank (the value indicated by "O$_2$ remaining"). As is shown, the O$_2$ remaining value is compared with an established data set of safe system parameters stored in a memory device as described above, said data set containing a "setpoint" reflecting known safe and undesirable oxygen tank pressure conditions (520). If the oxygen pressure is greater than the setpoint, no alarm sounds and no adjustment to drug delivery is effected (521). If the O$_2$% value is less than the setpoint, alarm "1" sounds (522). If alarm "1" is silenced manually within 15 seconds, no further action is taken by the system (523). If alarm "1" is not silenced within 15 seconds, the amount of drug being delivered (in this example gaseous N$_2$O) is reduced to the lesser of the concentration of 45% or the current concentration minus 10% (524). The software or logic procedure would operate in a similar fashion for intravenous and nebulized forms of drugs and the instructions provided (e.g., as in 524), would be specified for safe dosages of such drugs.

In another example of FIG. 21A involving a system state monitor which indicates whether power is being supplied to apparatus 10, a logic operation determines whether power has been interrupted. If the system state monitor for power signals that power has been interrupted, alarm "2" sounds and the delivery of drug is reduced to 0%.

Similar protocols are described in FIG. 21A for system state monitors indicating O$_2$ interruption fail safe, total gas flow, drug tank pressure, fraction of inspired oxygen (FIO$_2$), and operation of the vacuum pump for scavenging system 48 (FIG. 6). These protocols are effected with software (and/or logic) operating in similar fashion to that described in the dataflow diagram of FIG. 23A. That is, the protocol shown in FIG. 23A is one example employing one system state monitor stored parameters, but the operation would be similar to effect the remaining protocols of FIG. 21A.

In the above examples, involving response to patient physiological state, there is a time lapse between the alarm's sounding and any decrease in drug delivery to the patient. In alternate protocols contemplated by the invention, electronic controller 14 will immediately cease or curtail drug administration upon the sounding of an alarm. For less critical ("yellow") alarms, drug delivery may be decreased to 80% levels upon the sounding of the alarm; for more critical ("red") alarms, drug delivery would cease upon the sounding of the alarm. In either case, the physician will then be given time, for example, thirty seconds, to instruct controller 14 to restart the drug delivery (e.g., the physician will need to override the curtailing of drug delivery). If the physician does override controller 14, drugs are reinitiated, for example, by a bolus amount. This method prevents against a patient's deteriorating while a physician waits to respond to an alarm at current drug levels, and also avoids underdosing by permitting the physician sufficient time to reinitiate drug delivery.

Referring again to FIGS. 2 and 18, a printer 238 (FIG. 2, 37) provides an on-site hard copy of monitored patient health parameters (e.g., the feedback values from the one or more patient health monitors), as well as alarm states with time stamps indicating which type of alarms sounded, why and when. Diagnostic LEDs 240 affixed to the exterior of apparatus 10 (e.g., FIG. 1) and electronically coupled to controller 14 permit the physician typically involved in the procedure to ascertain system states at a glance; LEDs coupled to microprocessor controller 14 also permit service technicians to assess fault states.

Figure 19A:
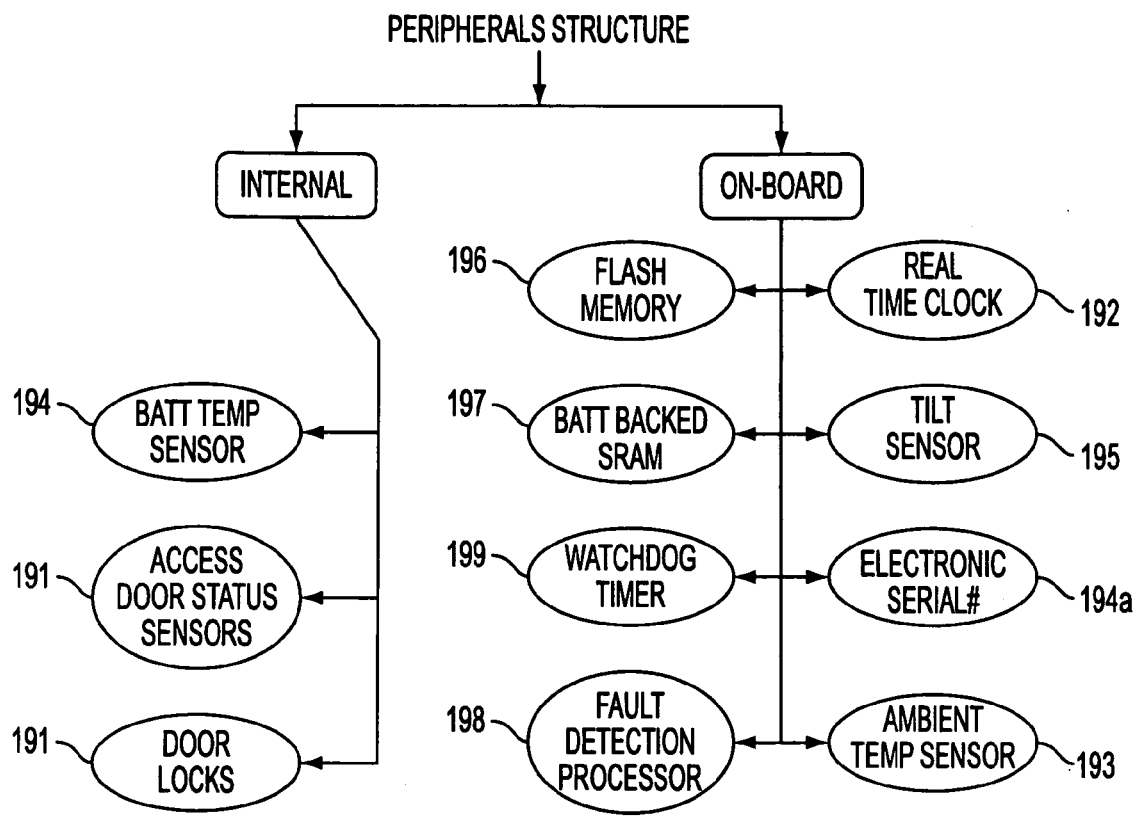
FIGS. 19A and 19B depict the various peripheral devices included in a preferred embodiment of the invention.
Figure 19B:
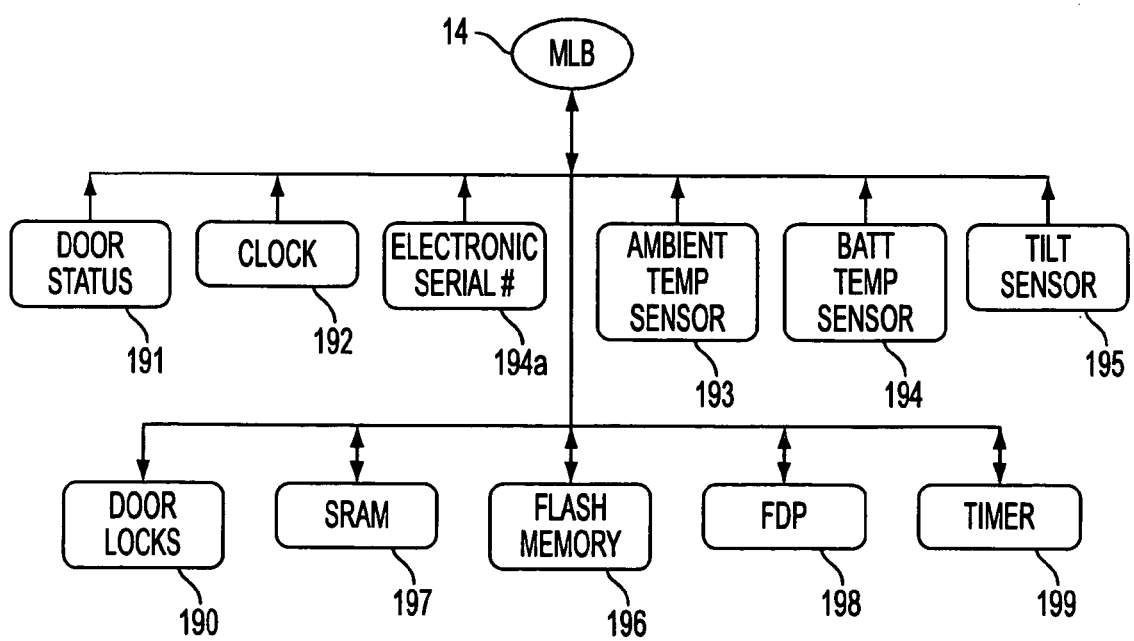

A preferred embodiment of the invention includes a variety of peripheral electronic devices, one group internal to or integrated within housing 15 of apparatus 10 (e.g., FIG. 1) and a second group on-board electronic controller 14. These electronic devices ensure proper operation of various aspects of system 10, including providing hardware status feedback through sensors to ensure that the apparatus is operating within its desired parameters. FIGS. 19A and 19B describe various peripheral devices in accordance with the invention, such devices may be of a known, off-the-shelf types currently available. Specifically, internal solenoid-type activated door locks 190 restrict access to the interior of apparatus 10. Door locks 190 are located within housing 15 (FIG. 1) and are electronically coupled to and controlled by controller 14 by means of software that includes protocols for password protection. Access to the interior of apparatus 10 is thus restricted to authorized personnel with passwords. This is intended to, among other things, minimize chances of "recreational" abuse of the pharmaceuticals (e.g., $N_2O$) contained therein. Internal door status sensors 191 located within housing 15 and electronically coupled to controller 14 generate signals indicating if an access door to the interior of apparatus 10 is open or closed. Real-time clock 192 on-board controller 14 enables said controller 14 to provide time stamps for overall system and patient activities and thereby enables creation of an accurate log of the operation of care system 10. On-board ambient temperature sensor 193 monitors the exterior temperature signaling same to controller 14 which through software comparison type protocols confirms that apparatus 10 is being operated under desired conditions with respect to surrounding temperature. Internal battery temperature sensor 194 located within housing 15 and electronically coupled to controller 14 generates signals to same indicating whether the back-up battery power system is functioning correctly and not overcharging. Tilt sensor 195 located on-board controller 14 signals same if the apparatus 10 is being operated at an angle beyond its designed conditions.

In a preferred embodiment, the software control processes of electronic controller 14 are stored in a standard flash memory 196 and SRAM type battery-backed memory 197 stores system, patient and other status information in the event of an AC power loss. On-board fault detection processor (FDP) 198 signals failures to controller 14 and is a secondary microprocessor based computing system which relieves controller 14 of its control duties if a fault is detected in operation. On-board watch dog timer 199 indicates to controller 14 that the apparatus 10 is functioning and resets controller 14 if system 10 fails to respond.

A preferred embodiment of the invention also includes a standard serial port interface, such as an RS-232C serial port, for data transfer to and from electronic controller 14. The port enables, for example, downloading software upgrades to and transfer of system and patient log data from controller 14. An interface such as a PC Type III slot is also provided to enable the addition of computer support devices to system 10, such as modems or a LAN, to be used, for example, to transfer billing information to a remote site; or to permit diagnosis of problems remotely thereby minimizing the time required for trouble-shooting and accounting.

It should be understood that the care system of the invention may be modular in nature with its functions divided into separable, portable, plug-in type units. For example, electronic controller 14, display devices (FIG. 2, 35) and one or more patient health monitors would be contained in one module, the pneumatic systems (flow controllers, pressure regulators, manifold) in a second module, and the base (FIG. 3B, 17), oxygen and drug tanks (FIG. 2, 54), scavenger system and vacuum pump (FIG. 3B, 32) in a third module. Additionally, the patient health monitors or drug delivery aspects of the system may each be their own plug-in type modules. The system, for example, may provide for a pluggable ventilator type module. This modularity enables the system not only to be more easily portable, but also enables use of certain features of the system (such as certain patient health monitors), while not requiring use of others.

Figure 20:
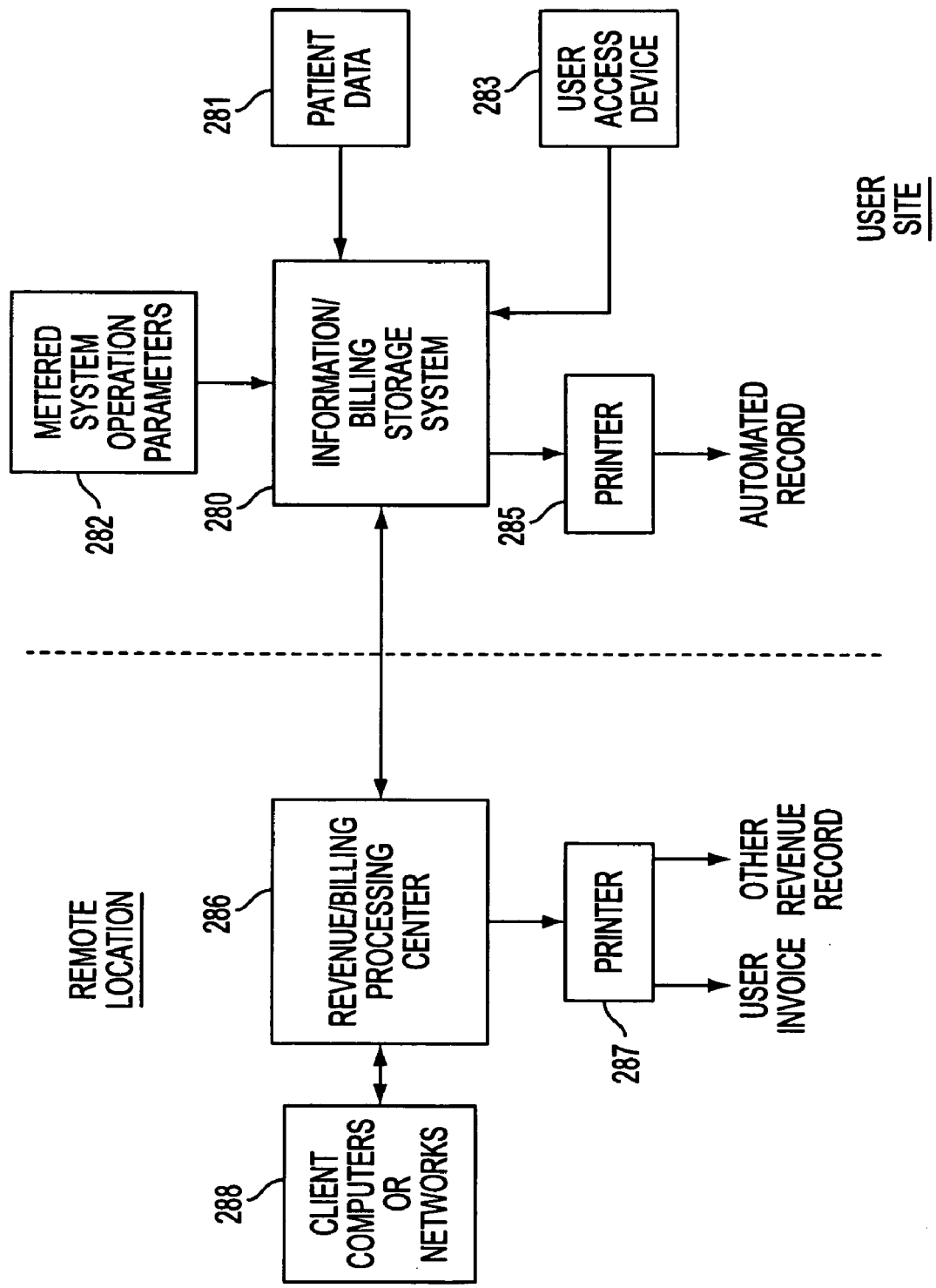
FIG. 20 depicts a preferred embodiment of a patient information/billing system in accordance with the invention.

FIG. 20 depicts a preferred embodiment of a patient information and billing system capable of being interfaced with care system 10 (FIG. 1) to allow billing or other gathering of patient information to take place locally at the place of use or remotely at a billing office. Specifically, information/billing storage system 280, which may be of a known type microprocessor-based computing system controlled by software, collects and stores patient data 281 such as the patient's name, address and other account information, as well as metered system operation data 282 generated during operation of apparatus 10 and stored in controller 14 such as start time, time of use, frequency of use, duration of patient monitoring, amount of gases expended, and other such parameters. User access device 283 which may be of a standard keyboard type permits the physician to interact with information/billing storage system 280 to input additional data such as pre-determined treatment or billing parameters or to read the status of same (e.g., to read the status of metered system operation parameters 282). Preferably, a password is provided to permit access to information/billing system 280.

At the termination of a medical or surgical procedure or at some other desired period, information/billing storage system 280 processes the received data and transmits same to revenue/billing processing center 286 at a remote location. Revenue/billing processing center 286 may be of a known, mainframe-type computing system such as that manufactured by International Business Machines (IBM) or a known client-server type computer network system. At the remote location a patient invoice is generated by printer 287 as may be other revenue records used for payment to vendors, etc.

The invention also contemplates that an automated record of the system operation details will be printed at the user site on printer 285 which is preferably located on-board apparatus 10 (FIG. 1). Such system operation details may include, for example, all alarm and actual system operation states, drug flow rates and/or monitored actual patient physiological conditions as supplied by electronic controller 14. A modem or LAN may be used to send and receive billing and other information remotely and to communicate with remote client/server or other networks 288 as described above.

I claim:

1. A device to provide sedation to a patient, said device comprising:
   a drug delivery mechanism for delivering a drug dosage rate of sedative to said patient during a procedure;
   a patient health monitor adapted so as to be coupled to a patient during said procedure, said monitor generating a signal reflecting measurements of at least one monitored physiological condition of the patient; and
   a processor operably connected to said patient health monitor and said drug delivery device; said processor having accessible parameters that indicate values for said measurements of said monitored physiological condition, said values correlating to a range of patient conditions associated with said procedure; and wherein said processor operates according to software to receive said signal during said procedure, analyze said measurements reflected in said signal using said parameters to identify onset or possible onset of a patient condition outside of a normal range, and generate a signal indicating possible modifications of said drug dosage rate to remedy said onset or possible onset of said patient condition, wherein said processor signal indicates an action dependent upon an extent by which said current measurements are outside said normal range.

2. The device as recited in claim 1, further comprising a fail safe system adapted to ensure proper operation of said device.

3. The device as recited in claim 1, wherein said processor employs an algorithm conforming to target-controlled infusion rates for controlling said drug delivery mechanism.

4. The device as recited in claim 1, wherein said patient health monitor is adapted to generate measurements reflecting effective spontaneous ventilation of the patient.

5. The device as recited in claim 1, wherein said patient health monitor comprises a brain activity monitor.

6. The device as recited in claim 1, wherein said patient health monitor is adapted to monitor a patient's end tidal carbon dioxide levels in an exhaled air stream of the patient.

7. The device as recited in claim 1, wherein said patient health monitor device comprises a capnometer.

8. The device as recited in claim 1, wherein said processor receives said signal during said procedure and identifies any onsets or possible onsets of patient condition episodes outside of a desired range through said comparison, and wherein said processor modifies said supply rate if necessary to remedy said episode.

9. The device as recited in claim 1, wherein said drug delivery mechanism includes means for delivering said sedative intravenously.

10. The device as recited in claim 1, wherein said parameters indicate values for said measurements of said monitored physiological condition that reflect the onset of potentially undesirable patient conditions during said procedure.

11. The device as recited in claim 10, wherein said parameters indicate values for said measurements of said monitored physiological condition that reflect the onset of potentially unsafe patient conditions during said procedure.

12. The device as recited in claim 1, further comprising a second health monitor adapted to be coupled to a patient and generate a second signal reflecting second measurements of a second physiological condition of the patient; and wherein said processor further contains second parameters indicating second values for said second measurements of said second physiological condition where said processor operates to receive said second signal, compare said second measurements reflected in said received second signal with said second parameters, and modify said dosage rate in response to said signal and said second signal as necessary to maintain safe and effective sedation during said procedure.

13. The device as recited in claim 1, wherein said drug delivery mechanism is electronically controllable to provide drug delivery according to infusion types selected from the group consisting of continuous infusion, target controlled intravenous infusion, bolus infusion, and combinations thereof.

14. The device as recited in claim 1, further comprising a recording means that creates records regarding patient conditions during said procedure.

15. The device as recited in claim 14, wherein said records created by said recording means further include drug usage data during said procedure.

16. The device as recited in claim 1, further comprising a manual input mechanism for permitting personnel performing the procedure to manually alter delivery of the sedative.

17. The device as recited in claim 16, wherein said input mechanism permits said personnel performing the procedure to increase a current dosage rate of drug delivery.

18. The device as recited in claim 17, wherein said values define a preset normal range of measurements of said monitored physiological condition for a patient undergoing said procedure, and wherein said processor controls said drug delivery mechanism by changing a drug dosage rate as necessary to maintain safe and effective sedation during said procedure.

19. The device as recited in claim 18, wherein said preset normal range is identified by at least one threshold for said measurements.

20. The device as recited in claim 19, wherein said values define at least two thresholds concerning said physiological condition, wherein said thresholds designate different levels of concern for said patient when said measurements move outside of said preset normal range.

21. The device as recited in claim 1, wherein said values define a preset normal range of measurements of said monitored physiological condition for a patient undergoing said procedure, said preset normal range of measurements corresponding to potential physiological conditions of a patient that is receiving propofol by continuous intravenous infusion.

22. The device as recited in claim 1, further including at least one alarm that is raised when said signal is determined to fall outside of said values correlating to safe and effective patient sedation during said procedure.

23. The device as recited in claim 22, wherein said processor curtails drug delivery upon the raising of said alarm if an unsafe patient condition is identified.

24. The device as recited in claim 22, wherein said processor increases the delivery of oxygen to the patient upon the raising of said alarm.

25. The device as recited in claim 22, wherein said alarm is adapted to produce alarms of multiple urgency levels as defined by said parameters.

26. The device as recited in claim 22, wherein said system also includes a display with an alarm box portion which displays a representation of the patient physiological condition associated with the raised alarm.

27. The device as recited in claim 26, wherein said monitored physiological condition is selected from the group consisting of a brain activity, heart rate, blood saturation, expired carbon dioxide, ventilation, and patient consciousness level.

28. The device as recited in claim 1, further comprising at least one system state monitor which generates a signal reflecting the state of at least one operating condition of the device and which is coupled to the processor; and wherein said processor has access to parameters indicating one or more operating conditions of the device.

29. The device as recited in claim 28, wherein said system state monitor is an oxygen source pressure sensor that measures the flow of oxygen to the patient.

30. The device as recited in claim 28, wherein said system state monitor indicates whether there has been a power failure in the device.

31. The device as recited in claim 28, wherein said processor activates an attention-commanding device in response to said signal reflecting the state of at least one operating condition of the device.

32. The device as recited in claim 28, wherein said system state monitor is a drug source flow sensor that measures flow of drug to the patient.

33. The device as recited in claim 1, wherein said signal causes a communication device to raise an alarm regarding the condition of said patient, said alarm suggesting said possible modifications.

34. The device as recited in claim 33, wherein said possible modifications include a default action to be taken by said drug delivery mechanism, wherein said default action is performed by said drug delivery mechanism in the absence of contrary instructions from medical personnel within a time period after said alarm is raised.

35. The device as recited in claim 34, wherein said default action comprises said drug delivery mechanism device decreasing said drug dosage rate.

36. A device for providing sedation to a patient during a medical and/or surgical procedure, said device comprising:
    an electronic drug delivery device adapted to be coupled to said patient and deliver to said patient one or more drugs at a drug delivery rate to provide sedation;
    a monitor adapted to be coupled to the patient and provide feedback indicative of at least one monitored physiological condition of the patient;
    a processor connected to said monitor, said processor receiving said feedback from said monitor and comparing said feedback to parameters that define whether a given patient is experiencing or in danger of experiencing an undesirable patient condition while receiving said drug at said drug delivery rate, and said processor thereby generating a signal reflecting the monitored physiological condition of the patient and indicating modifications of said drug delivery to avoid said undesirable patient condition during said medical procedure.

37. The device as recited in claim 36, wherein said processor is further adapted to communicate an alarm to said medical personnel in response to said signal, said alarm indicating that a possible modification of said drug delivery may need to occur to avoid said undesirable patient condition.

38. The device as recited in claim 37, wherein said electronic drug delivery device allows manual altering of delivery of drug by medical personnel in response to said feedbacks.

39. The device as recited in claim 37, wherein said processor is further adapted to communicate an alarm to said medical personnel in response to said signal, said alarm indicating that a possible modification of said drug delivery may need to occur to remedy an undesirable patient condition.

40. The device as recited in claim 37, wherein said alarm alerts a medical personnel of possible therapeutic options; said therapeutic options being identified by said comparison.

41. The device as recited in claim 36, wherein said monitor is selected from the group consisting of an electrocardiograph, a pulse oximeter, a brain activity monitor, a capnometer, a blood pressure monitor and a patient consciousness monitor.

42. The device as recited in claim 36, wherein said parameters define a preset normal range of said feedback for a patient undergoing said procedure, and wherein said modifications of drug delivery comprises decreasing a current drug delivery rate or raising an alarm if said monitored physiological condition of the patient moves outside of said preset normal range.

43. The device as recited in claim 42, wherein said preset normal range is identified by at least one threshold for said feedback.

44. The device as recited in claim 43, wherein said parameters define at least two thresholds concerning said feedback, and wherein said thresholds designate different levels of concern for said patient when said feedback is outside of said preset normal range.

45. The device as recited in claim 36, wherein delivering of the drugs is accomplished by target-controlled infusion.

46. The device as recited in claim 36, wherein said monitor is a brain activity monitor and said controlling of said drug delivery device comprises causing said drug delivery device to modify a supply rate of drug automatedly in response to said signal.

47. The device as recited in claim 36, wherein said monitor is a pulse oximeter and said controlling of said drug delivery device comprises causing said drug delivery device to modify a supply rate of drug in response to changes in a monitored blood oxygen level of the patient.

48. The device as recited in claim 36, wherein said monitored physiological condition is effective spontaneous ventilation of the patient.

49. The device as recited in claim 36, wherein said monitor is a blood pressure monitor.

50. The device as recited in claim 36, further comprising means for creating a record detailing control of said drug delivery during said procedure.

51. The device as recited in claim 50, wherein said record further details information regarding said monitored physiological condition.

52. The device as recited in claim 50, wherein said record further details alarms generated in response to said signal.

53. The device as recited in claim 36, wherein said drug delivery device is adapted to perform a delivery mechanism selected from the group consisting of continuous infusion, target controlled infusion, bolus infusion, and combinations thereof.

54. The device as recited in claim 36, wherein said processor further receives a second signal reflecting a state of at least one operating condition of said drug delivery device or said monitor, said signal being received by said processor, and said processor thereby initiating alarms if said operating condition is unsatisfactory.

55. The device as recited in claim 54, wherein said operating conditions are of types selected from the group consisting of oxygen flow status, power failures, and drug flow status.

56. The device as recited in claim 36, wherein said monitored physiological condition is the patient's level of consciousness.

57. A device for sedating a patient undergoing one or more medical and/or surgical procedures, said device comprising:
    a drug delivery device adapted to be connected to a patient and capable of controllable drug delivery to the patient during a procedure;
    an electronic controller coupled to said drug delivery device, said controller adapted to control the delivery of drugs by said drug delivery device;
    a patient health monitor device to a patient, said health monitor device generating a signal reflecting at least one monitored physiological condition of the patient, said signal being sent from said health monitor device to said electronic controller to communicate a current measurement reflecting said monitored physiological condition of the patient; and wherein said electronic controller accesses parameters for said monitored physiological condition, said parameters including values for said measurements of said monitored physiological condition where said values correlate to safe and effective sedation during said procedure, said electronic controller compares said measurement reflected in said received signal with said parameters, and said electronic controller modifies a supply rate of the drugs according to software to maintain safe and effective sedation of the patient during said procedure, said electronic controller modifying said supply rate to an extent being dependent upon a second extent by which said measurement is outside one or more ranges defined by said parameters.

58. The device as recited in claim 57, wherein said patient health monitor device is selected from the group consisting of an electrocardiograph, a pulse oximeter, a brain activity monitor, a capnometer, a blood pressure monitor and a patient consciousness monitor.

59. The device as recited in claim 57, wherein said one of said ranges is defined by values that establish a preset normal range of said measurements for a patient undergoing said procedure, and wherein said modifying of said drug delivery rate comprises said electronic controller decreasing a current drug delivery rate or raising an alarm if said monitored physiological condition of the patient moves outside of said preset normal range.

60. The device as recited in claim 59, wherein said preset normal range is identified by at least one threshold for said measurements.

61. The device as recited in claim 60, wherein said values establish at least two thresholds concerning said physiological condition, and wherein said thresholds designate different levels of concern for said patient when measurements are outside of said preset normal range.

62. The device as recited in claim 57, wherein said values define measurements of said monitored physiological condition that evidence the onset of potentially undesirable patient conditions during said procedure.

63. The device as recited in claim 57, wherein said electronic controller modifies said supply rate according to a target-controlled infusion algorithm.

64. The device as recited in claim 57, wherein said patient health monitor device is a brain activity monitor and said modifying of said supply rate of drug is in response to a concentration of drug in the patient.

65. The device as recited in claim 57, wherein said patient health monitor device is a pulse oximeter and the modifying of said supply rate of the drug is in response to changes in a monitored blood oxygen level of the patient.

66. The device as recited in claim 57, wherein said monitored physiological condition is effective spontaneous ventilation of the patient.

67. The device as recited in claim 57, wherein said monitor device is a blood pressure monitor.

68. The device as recited in claim 57, further comprising means for creating a record detailing delivering of said drug during said one or more procedures.

69. The device as recited in claim 68, wherein said record further details information regarding said monitored physiological condition.

70. The device as recited in claim 57, wherein said drug delivery device is further adapted to permit manual altering the delivery of drug.

71. The device as recited in claim 70, wherein said manual altering comprises increasing a current rate of drug delivery to the patient.

72. The device as recited in claim 57, wherein said electronic controller receives a signal reflecting a state of at least one operating condition of said drug delivery device or said patient health monitor device, and said controller is adapted to initiate alarms if said operating condition is unsatisfactory.

73. The device as recited in claim 72, wherein said operating conditions are of types selected from the group consisting of oxygen flow status, power failures, and drug flow status.

74. The device as recited in claim 57, wherein said monitored physiological condition is the patient's level of responsiveness.

* * * * *

UNITED STATES PATENT AND TRADEMARK OFFICE
CERTIFICATE OF CORRECTION

PATENT NO. : 7,201,734 B2  Page 1 of 1
APPLICATION NO. : 10/909435
DATED : April 10, 2007
INVENTOR(S) : Randall S. Hickle It is certified that error appears in the above-identified patent and that said Letters Patent is hereby corrected as shown below:

In Column 38, claim 57, line 65, please delete "a patient health monitor device to a patient, said health" and insert -- a patient health monitor device adapted to be coupled to a patient, said health --

Signed and Sealed this
Twenty-fourth Day of January, 2012

David J. Kappos
*Director of the United States Patent and Trademark Office*